United States Patent [19]

Nagata et al.

[11] Patent Number: 4,529,721

[45] Date of Patent: Jul. 16, 1985

[54] VINYLTHIOACETAMIDO OXACEPHALOSPORIN DERIVATIVES

[75] Inventors: Wataru Nagata, Nishinomiya; Mitsuru Yoshioka, Toyonaka; Yasuhiro Nishitani, Izumi; Tsutomu Aoki, Sennan; Toshiro Konoike, Suita; Tadatoshi Kubota, Habikino, all of Japan

[73] Assignee: Shionogi & Co., Ltd., Osaka, Japan

[21] Appl. No.: 534,147

[22] Filed: Sep. 21, 1983

[30] Foreign Application Priority Data

Sep. 30, 1982 [JP] Japan ............................... 57-172907
Jul. 13, 1983 [JP] Japan ............................... 58-128116

[51] Int. Cl.³ ..................... A01N 59/06; A01N 43/90; C07D 498/04

[52] U.S. Cl. .................................... 514/191; 562/426; 562/507; 260/349; 562/556; 562/595; 260/465 D; 562/598; 260/465.4; 514/210; 544/64; 544/90; 544/215; 544/224; 544/236; 544/282; 544/335; 544/385; 546/147; 546/170; 546/341; 548/125; 548/131; 548/204; 548/236; 548/253; 548/342; 548/378; 548/494; 548/562; 549/39; 549/58; 549/79; 549/273; 549/283; 549/420; 549/471; 549/499

[58] Field of Search ............... 544/90, 64; 424/248.51, 424/248.52

[56] References Cited

U.S. PATENT DOCUMENTS 4,371,532 2/1983 Narisada et al. .................. 544/90 X

*Primary Examiner*—Richard L. Raymond
*Attorney, Agent, or Firm*—Wenderoth, Lind & Ponack

[57] ABSTRACT

A compound of the formula:

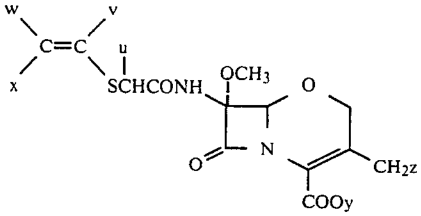

(I)

wherein u represents hydrogen, carboxamido, N-hydroxycarboxamido, carboxy, azido, an aryl, an acylamino, a protected carboxy or an N-alkoxycarboxamido, or, together with v, can represent —S— or —$CH_2S$—; v represents hydrogen, halogen, cyano or an alkylthio, or, together with u, can represent —S— or —$CH_2S$—, or, together with w, can represent —$(CH_2)_3CO$—; w represents hydrogen, carboamoyl, cyano, carboxy, an N-alkylcarbamoyl, an alkyl, an aryl, a protected carboxy or a heterocycle, or, together with v, can represents —$(CH_2)_3CO$—; x represents halogen, trifluoromethyl, an alkylthio or an arylthio; y represents hydrogen, a light metal or a carboxylic acid protecting group; and z represents an acyloxy or a heterocyclethio, each of the above radicals represented by the symbols u, v, w, x, y and z being optionally substituted by halogen or a carbon-, nitrogen-, oxygen- or sulfur-containing functional group, a process for preparing the compound, a pharmaceutical composition containing the compound, and a therapeutic use of the compound.

A compound of the formula:

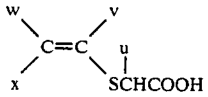

(III)

wherein u, v, w and x are as defined above, useful as a starting compound for preparing the compound (I) is also provided.

12 Claims, No Drawings

VINYLTHIOACETAMIDO OXACEPHALOSPORIN DERIVATIVES

The present invention relates to 7β-substituted vinylthioacetamido-7α-methoxy-3-substituted methyl-1-dethia-1-oxa-3-cephem-4-carboxylic acid derivatives of the formula (I), their use, processes for preparing them and pharmaceutical compositions containing them:

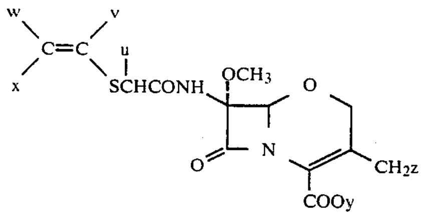

(I)

wherein u represents hydrogen, carboxamido, N-hydroxycarboxamido, carboxy, azido, $C_6$ to $C_{12}$ aryl, $C_1$ to $C_{12}$ acylamino, a protected carboxy or N-$C_1$ to $C_5$-alkoxycarboxamido, or, together with v, can represent —S— or —$CH_2S$—; v represents hydrogen, halogen, cyano or $C_1$ to $C_5$ alkylthio, or, together with u, can represent —S— or —$CH_2S$—, or, together with w, can represent —$(CH_2)_3CO$—; w represents hydrogen, carbamoyl, cyano, carboxy, N-$C_1$ to $C_5$-alkylcarbamoyl, $C_1$ to $C_5$ alkyl, $C_6$ to $C_{12}$ aryl, a protected carboxy or 5 or 6 membered nitrogen-, oxygen- or sulfur-containing heterocycle, or, together with v, can represents —$(CH_2)_3CO$—; x represents halogen, trifluoromethyl, $C_1$ to $C_5$ alkylthio or $C_6$ to $C_{12}$ arylthio; y represents hydrogen, a light metal or a carboxylic acid protecting group; and z represents $C_1$ to $C_{12}$ acyloxy or a heterocycle-thio as above.

Each of the above radicals represented by the symbols u, v, w, x, y and z can be optionally substituted by halogen or a carbon-, nitrogen-, oxygen- or sulfur-containing functional group.

In this specification, preferable ranges of the terms are as follows:

The term "alkyl" refers to a straight chain or branched-chain $C_1$ to $C_5$ alkyl optionally substituted by hydroxy, halogen, cyano, carboxamido, carbamoyl, oxo, $C_1$ to $C_5$ alkyl, $C_1$ to $C_5$ alkoxy, $C_1$ to $C_{12}$ acyloxy, amino, $C_1$ to $C_{12}$ acylamino, di-$C_1$ to $C_5$-alkylamino, formylimidoylamino or a protected carboxy, or $C_4$ to $C_7$ cycloalkyl optionally substituted by any one of the just mentioned substituents. These substituents will be referred to as "common substituents" hereinafter.

The term "acyl" refers to a straight chain or branched-chain $C_1$ to $C_7$ alkanoyl, $C_4$ to $C_7$ cycloalkylcarbonyl, a monocyclic or bicyclic $C_7$ to $C_{13}$ aroyl, $C_8$ to $C_{14}$ aralkanoyl or $C_9$ to $C_{15}$ arylalkenoyl, each optionally containing hetero atom(s) selected from nitrogen, oxygen or sulfur in the ring, $C_1$ to $C_5$ alkylsulfonyl, $C_6$ to $C_{12}$ arylsulfonyl, carbamoyl, a carbo-$C_1$ to $C_5$-alkoxy, a carbo-$C_7$ to $C_{13}$-aralkoxy or sulfo. These acyl groups can optionally bear one or more of the common substituents just mentioned above.

The term "aryl" refers to a 5 or 6 membered, mono- or bicyclic $C_6$ to $C_{12}$ aryl group optionally carrying one or more of the common substituents described above.

The term "heterocycle" refers to a 5 or 6 membered, mono or bicyclic heterocyclic group having one oxygen atom or one sulfur atom and/or one to four nitrogen atoms. Illustrative of the heterocycles are furyl, thienyl, pyronyl, thiopyronyl, pyrrolyl, pyrazolyl, oxazolyl, thiazolyl, imidazolyl, oxadiazolyl, oxatriazolyl, thiadiazolyl, triazolyl, oxatriazolyl, thiatriazolyl, tetrazolyl, pyridyl, pyrimidyl, pyradinyl, pyridazinyl, triazinyl, indolyl, benzopyronyl, benzofuryl, benzothienyl, tetrazolopyridazinyl, purinyl, isoquinolyl, quinolyl, pyrimidopyridyl, etc. These heterocycles can carry one or more of substituents selected from the group consisting of optionally protected hydroxyethyl, carbamoylmethyl, alkylcarbamoylmethyl and the common substituents mentioned in the explanation of the "alkyl" group. The examples of the protecting group for hydroxyethyl are an aralkyl; an acylate-forming group such as carbonic acyl, alkanoyl, aralkanoyl, aroyl; an acetal forming group such as methoxymethyl, tetrahydropyranyl. Of these protecting groups, preferable are those which can be introduced or deprotected from the compound (I) without adversely affecting the other part of the molecule.

The carboxy protecting groups are those commonly employed in the penicillin-cephalosporin art to protect the 3- or 4- carboxyl group without adversely affecting the β-lactam ring. Illustrative of these protecting groups are, for example, $C_7$ to $C_{14}$ aralkyl such as benzyl, methylbenzyl, dimethylbenzyl, methoxybenzyl, ethoxybenzyl, nitrobenzyl, aminobenzyl, diphenylmethyl, phthalidyl or phenacyl; a substituted $C_1$ to $C_5$ alkyl such as trichloroethyl, t-butyl or allyl; $C_6$ to $C_{12}$ aryl such as pentachlorophenyl or indanyl; an ester residue formed with acetone oxime, acetophenone oxime, acetaldoxime or N-hydroxyphthalimide; an acid anhydride residue formed with carbonic acid or $C_1$ to $C_{14}$ carboxylic acid. The protecting groups also include an amide residue, preferably a hydroxyamide or alkoxyamide residue, an imide residue and a hydrazide residue. The protecting groups can bear one or more of the common substituents mentioned in the explanation of the "alkyl" group.

It should be noted that the term "carboxy protecting group" herein used includes a pharmacologically active ester forming group. The term "pharmacologically active ester" is herein employed to denote the ester of the formula (I) which shows an antibacterial activity when orally or parenterally administered.

The pharmacologically active ester forming groups are those known in the penicilliin-cephalosporin art. Typical examples of the groups include substituted alkyl groups such as an alkanoyloxyalkyl, an alkoxyformyloxyalkyl, methoxymethyl, tetrahydropyranyl and 2-oxo-1,3-dioxolenylmethyl; substituted aralkyl groups such as phenacyl and phthalidyl; substituted aryl groups such as phenyl, xylyl and indanyl; and said groups substituted by one or more of the aforementioned common substituents.

The term "light metal" denotes a metal belonging to the second to fourth period of the groups I to III in the periodic table, which provides a physiologically acceptable ion in the body fluid. Lithium, sodium, potassium, magnesium, calcium and aluminium are representative of the light metals.

In the following description, the light metal, and a salt of the light metal or a base will be referred to simply as "metal", "a salt" or "a base" respectively, as long as misunderstanding will not occur from the context.

The compounds (I) of the invention exhibit a strong antibiotic activity to various microorganisms and, also to those resistant to other antibiotics. When administered to mammals, they show excellent pharmacological characteristics with respect to absorption, distribution, metabolism and excretion, without exhibiting remarkable side-effect. In addition, the compounds (I) are chemically stable, and therefore, can be stored for a long time.

Thus, the compounds (I) are valuable antibiotics against various gram positive and negative bacteria, and useful as drugs for human and veterinary uses. They can be used for treating or preventing infections caused by gram positive bacteria (e.g. *Staphylococcus aureus, Streptococcus pyrogenes, Bacillus subtilis, Bacillus cereus, Diplococcus pneumoniae, Corynebacterium diphtheriae*) and gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens*), and some are active even against anaerobic bacteria (e.g. *Bacteroides fragilis, Eubacterium lentum*). The compounds can be used also as disinfectants for preventing decay of perishables, additives to feedstuffs, or preventing bacterial growth of hygenical materials.

The compounds (I) can be used in a wide variety of oral or parenteral dosage forms solely or in admixture with other coacting substances. The pharmaceutical compositions may be a mixture of 0.01 to 99% of compound (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalent, suspensions, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate); emulsifying agents (e.g. lecthin, sorbitan monooleate, acacia); suspensing agents (e.g. sorbitol, methyl cellulose, glucose, or sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds (I) having a carboxylic acid salt group are soluble in water, and conveniently used as solution for intravenus, intramuscular, or subcutaneous injection according to a conventional method. The compounds can be dissolved in aqueous or oily solvents for injection to give a solution in an ampoule, but generally, more prolonged storage are possible by making a vial preparation containing crystals, powder, microcrystals, or lyophilizate of compound (I), and dissolving or suspending the drug before use with the said solvents for injection. The preparation may contain preferably said preservative. The vial preparation or injection can be given to a patient at a daily dose of e.g. 0.2 to 5 g depending on the infected bacteria, condition of the patient, and interval of the administration.

Compounds (I), being a pharmaceutically acceptable ester (e.g. indanyl, acetoxymethyl, pivaloyloxymethyl, ethoxycarbonyloxyethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension, and like oral preparations. They may be pure compounds or a composition comprising compounds (I) and said pharmaceutical carriers. The preparation can be made according to the methods conventional in the art, and can be administered to a patient at a daily dose of e.g. 1 to 2 g depending on the condition of patient and the diseases.

Further, compounds (I) can be used as suppositories, ointments for topical or ocular use, powders for topical use, and like preparations preparable according to methods well known to those skilled in the art. The preparation can contain 0.01 to 99% of the compound (I) together with a necessary amount of pharmaceutical carrier given above. A necessary amount e.g. 1 μg to 1 mg of the preparation can be applied to the affected part.

This invention also provides a method for treating or preventing human or veterinary bacterial infections by administering to the human or animal subject an effective amount of compound (I) at a daily dose of e.g. 0.2 to 5 g for injection or e.g. 1 to 2 g for oral administration, or 1 μg to 1 mg for topical application, at an interval of e.g. 3 to 12 hours.

The method is applicable for treating or preventing some diseases caused by bacteria sensitive to compounds (I) e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections, and pyelonephritis when caused by bacteria sensitive to compound (I).

Preferably the compounds (I) are given to a patient in forms of pharmaceutical preparations e.g. powder, dry syrup, tablets, traches, granules, capsules, pills, suppositories, injections, ointments, dispersions, inhalent, suspensions, solutions, emulsions, syrups, and elixirs. They may be in a unit dosage form e.g. tablets, troches, capsules, injections, vials, granules or powder in a separate container or package.

All of the pharmaceutical preparations listed above can be prepared in a conventional manner.

It will be readily understood to those in the art that the compounds (I) can also be used as germicides or anticeptics. In addition, they are useful as a starting material for preparing some other compounds of the formula (I) and as an antibiotic agent for testing the sensitivity of microorganisms.

Preferred compounds (I) of the invention are those wherein x is trifluoromethyl, halogen or an alkylthio. Among them, the compounds (I) wherein x is halogen, particularly fluorine or chlorine, w is carbamoyl or an alkylcarbamoyl, and z is a substituted tetrazolylthio are particularly preferred.

The compounds of the formula (I) can be prepared by various methods detailed below:

1. Preparation of salts

The reaction of the compound (I) wherein y is hydrogen with a base or a salt of weaker carboxylic acid results in the compound (I) wherein y is a light metal. The reaction may be carried out according to a conventional method known to the art. Preferred methods are the neutralization of the free acid (I) with a metal bicarbonate. Alternative method is the exchange reaction of the free acid (I) with a salt of a lower carboxylic acid in a polar organic solvent followed by the addition of a solvent to which the desired salt (I) is sparingly soluble.

The bove reactions complete after one to ten minutes when carried out at a temperature below 50° C. If necessary, the reaction mixture can be kept for a longer time unless any side reaction occurs.

2. Elimination of carboxylic acid protecting group

The compounds of the formula (I) wherein y is a carboxy protecting group can be converted to the compounds (I) where y is hydrogen according to any of the deprotecting reactions described below.

In the following description, the carboxylic acid protecting group will be sometimes represented by the name corresponding to the group formed by the reaction between the carboxylic acid and the compound for protecting the carboxylic acid, only for the purpose of avoiding the complexity of description. Thus, the protecting group "R" or "NHR" contained in the moiety of the formula:

—COOR or —CONHR will be referred to as "ester" or "amide", respectively.

(a) The compounds (I) having highly reactive protecting groups, such as highly reactive esters, amides and anhydrides, can be deprotected by contact with an acid, a base, a buffer or an ion exchange resin in an aqueous solution. Less reactive protecting group such as trichloroethyl or p-nitrobenzyl can be eliminated by treating it with a combination of a metal and a acid or with dithionate, or by a catalytic reduction.

(b) Aralkyl esters can be eliminated by a hydrogenation using, e.g., platinum, palladium or nickel as a catalyst.

(c) Aralkyl esters, cyclopropylmethyl esters and sulfonylethyl esters can be eliminated through solvolysis using a mineral acid, a Lewis acid such as aluminum chloride, tin chloride and titanium tetrachloride, a sulfonic acid such as methanesulfonic acid and trifluoromethanesulfonic acid, or a strong carboxylic acid such as trifluoroacetic acid, and if necessary, in the presence of a cation scavenger.

(d) Phenacyl esters, alkenyl esters and hydroxyaralkyl esters can be eliminated by the action of a base or a nucleophile. A photochemically active phenacyl ester can be eliminated by light irradiation.

(e) A 2-alkynyl ester can be converted to an alkali metal salt by reaction with an alkali metal alkanoate and palladium triphenylphosphine.

(f) The other conventional processes known for deprotecting carboxy protecting groups can be employed in the present invention.

3. Introduction of group z

By the reaction of the compound (I) wherein z is a leaving group with an optionally substituted heterocycle-thiol or a reactive derivative thereof, the compound (I) wherein z is an optionally substituted heterocyclic-thio radical is obtained. Preferred leaving groups are halogen, sulfonyloxy, alkanoyloxy, dihaloacetoxy, trihaloacetoxy, etc. The preferred reactive derivatives of the heterocyclic-thiol are an alkali metal salt, an ammonium salt and a carboxylate of the thiol.

The reaction is carried out in an anhydrous or aqueous organic solvent at a temperature between 0° and 60° C. A dehydrating agent or phosphoryl chloride accelerates the reaction.

4. Amidation

The compounds of the formula (I) can be prepared by reacting a compound of the formula (II):

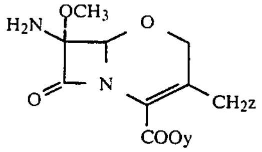

(II)

wherein y and z are as defined above, or a reactive derivative thereof with a substituted vinylthioacetic acid of the formula (III):

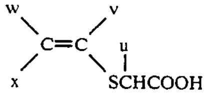

(III)

wherein u, v, w and x are as defined above, or a reactive derivative thereof.

Typical reactive derivatives of the amine (II) are those wherein the amino group at the 7-position has been activated by a silyl radical such as trimethylsilyl, methoxydimethylsilyl or tert-butyldimethylsilyl; a stannyl radical such as trimethylstannyl; an alkylene radical forming enamino of such an enamine-forming compound such as aldehyde, acetone, acetylacetone, acetoacetic ester, acetoacetonitrile, acetoacetanilide, cyclopentadione or acetylbutyrolactone; an alkylidene radical such as 1-haloalkylidene, 1-haloaralkylidene, 1-alkoxyalkylidene, 1-alkoxyaralkylidene, 1-alkoxy-1-phenoxyalkylidene, alkylidene or aralkylidene; an acid such as mineral acid, carboxylic acid or sulfonic acid (the acid forms a salt with the amino group); or an easily leaving acyl radical such as alkanoyl.

The above radicals for activating the amino group at the 7-position of the compounds (II) can carry any of the common substituents mentioned in the explanation of the term "alkyl".

The reactive derivatives of the substituted vinylthioacetic acid (III) are conventional acylating derivatives of the acids, such as anhydrides, halides, activated esters, activated amides and azides.

The reaction between the compound (II) and the compound (III) is conducted in different manners as explained below depending on the nature of the reactants.

(a) Free acids

One mole of the amine (II) is reacted with one to two moles of the acid (III) in an organic solvent, preferably in an aprotic organic solvent such as halogenated hydrocarbon, nitrile, ether, amide or a mixture thereof, in the presence of one to two moles of a condensing agent.

Suitable condensing agents include, for example, carbodiimides such as N,N'-diethylcarbodiimide and N,N'-dicyclohexylcarbodiimide; carbonyl compounds such as carbonyldiimidazole; isoxazolium salts; acylamino compounds such as 2-ethoxy-1-ethoxycarbonyl-1,2-dihydroquinoline; enzymes for amidation, etc.

(b) Acid anhydride derivatives

One to two moles of the acid anhydride derivative of the compound (III) is reacted with one mole of the amine (II), either in an organic solvent, preferably in an aprotic organic solvent such as halogenated hydrocarbon, nitrile, ether, amide or a mixture thereof, in the presence of zero to one mole of an acid scavenger, or in an aqueous medium under Schotten-Baumann reaction conditions.

The acid anhydrides employed in the reaction include symmetric anhydrides of the acids (III); mixed anhydrides of the acid (III) with either a mineral acid such as phosphoric acid, sulfuric acid or semicarbonate, or an organic acid such as alkanoic acid, aralkanoic acid or sulfonic acid; intramolecular anhydrides such as ketenes and isocyanates, etc.

The following compounds are particularly useful as the acid scavenger used in this reaction: inorganic bases such as oxides, hydroxides, carbonates and bicarbonates of an alkali metal or an alkaline earth metal; organic bases such as tertiary amines and aromatic amines; oxiranes such as alkylene oxides and aralkylene oxides; pyridinium salts such as tripiridiniumtriazine trichloride; adsorbents such as cellite, etc.

(c) Acid halide derivatives

One to two moles of the acid halide derivative of the compound (III) is preferably reacted with one mole of the amine (II) or its reactive derivative either in a solvent, such as halogenated hydrocarbon, nitrile, ether, ester, ketone, dialkylamide, aqueous medium, or a mixture thereof, in the presence of one to 10 moles of an acid scavenger selected from those mentioned in the above item (b), or in an aqueous medium under Schotten-Baumann reaction conditions.

(d) Activated ester derivatives

One to two moles of the activated ester derivative on the compound (III) is reacted with the amine (II) or its reactive derivative in an organic solvent, preferably in an aprotic organic solvent such as halogenated hydrocarbon, ether, ketone, nitrile, ester, amide or a mixture thereof at a temperature between $-20°$ C. and $40°$ C. for 1 to 5 hours.

Examples of the activated esters employed in this reaction are enol esters such as vinyl ester and isopropenyl ester; aryl esters such as phenyl ester, halophenyl ester and nitrophenyl ester; heterocyclic esters such as pyridyl ester and benzotriazolyl ester; esters formed with an N-hydroxy compound; esters formed with a diacylhydroxylamine such as N-hydroxysuccinimide and N-hydroxyphthalimide; thiol esters such as aralkyl ester and tetrazolylthiol ester; and other activated esters known per se.

The lower alkyl ester of the compound (III) which is enzymatically active can be reacted with the amine (II) in an aqueous medium in the presence of an amidating enzyme according to a per se conventional method.

(e) Activated amide derivatives

The activated amide derivative of the compound (III) is reacted with the amine (II) or its reactive derivative in the same manner as the activated ester just mentioned above. Examples of the amide derivatives employed in the reaction are those formed with an aromatic compound such as imidazole, triazole, 2-ethoxy-1,2-dihydroquinoline, etc.

Other reactive derivatives of the compound (III), such as formimino compound (e.g. N,N-dimethylformimino ester halide) can be employed in the amidation reaction.

5. Introduction of methoxy group

The compounds (I) can be prepared by reacting a starting compound corresponding to the compound (I) wherein methoxy at the 7-position is replaced by hydrogen, with an N-halogenating agent, and subsequently with a dehydrohalogenating agent and methanol. This reaction yields 7$\beta$-amido-7$\alpha$-methoxy compound (I) irrespective of the configuration of the hydrogen atom at the 7-position of the starting compound. The reaction can be carried out according to any one of the following procedures.

(a) The starting compound is reacted with an alkyl hypochlorite (e.g. tert-butyl hypochlorite) and an alkali metal methoxide (e.g. lithium methoxide, sodium methoxide) in methanol.

(b) The starting compound is reacted in methanol with molecular halogen and a base such as a metal alkoxide (e.g. lithium methoxide, sodium methoxide, magnesium methoxide), 1,5-diazabicyclo[5.4.0]-5-undecene(DBU), triethylamine, picoline, etc.

(c) The starting compound is reacted with an N-halogenating agent (e.g. a salt or an ester of hypohalogenous acid, N-haloamide, N-haloimide) and a dehydrohalogenating agent (e.g. an alkali metal alkoxide, aryl alkali metal), and subsequently with methyl alcohol.

Other conventional methods known per se can be employed for the introduction of methoxy group.

6. Modification of the acyl moiety

Various compounds corresponding to the compound (I) wherein the acyl moiety of the side chain at the 7-position differs from that of the compound (I) of the invention can be converted to the compound (I) by the following modifications of the acyl moiety.

The starting compound which differs from the compound (I) only in the acyl moiety is referred to as "pre-compound (I)" in the following description as a matter of convenience.

(a) Reductive elimination

The pre-compound (I) having an acetamido group substituted by an ethylthio group which bears leaving groups at 1'- and 2'-positions can be treated with a reducing agent (e.g. a metal and an acid, a borohydride complex) to give the compound (I) having a vinylthioacetamido group at the 7-position. As the leaving group, there may be exemplified halogen, alkylthio, sulfinyl, hydroxy, acyloxy, etc. This reaction can be carried out in an inert solvent.

(b) Elimination

The pre-compound (I) having an acetamido group substituted by an ethylthio group which bears a leaving group at either 1'- or 2'-position and hydrogen at the other position can be reacted with a base to provide the compound (I) having a vinylthioacetamido group. The leaving groups can be the same as above. Examples of the base employed in the reaction are DBU, 1,5-diazabicyclo[4.3.0]-5-nonene (DBN), tertiary bases, aromatic bases and the like.

When the leaving group is halogen, conventional dehydrohalogenating agents such as a combination of a lithium halide and dimethylformamide can be conveniently employed. When the leaving group is hydroxy, dehydrating agents such as a combination of thionyl chloride and a base can be employed.

The pre-compound (I) can also be converted to the compound (I) by pyrrolysis. Addition of a heavy metal catalyst often accelerates the conversion.

(c) Addition reaction

The reaction between the pre-compound (I) having a halothioacetamido group at the 7β-position with an ethynyl compound results in the corresponding compound (I) having a halovinylthioacetamide group. Likewise, the pre-compound (I) having mercaptoacetamido group also provides the compound (I) having the halovinylthioacetamido group by the reaction with a haloethynyl compound. By addition of an alkyl mercaptane or a hydrogen halide to the pre-compound (I) having an ethynylthioacetamido group, the corresponding compound of the formula (I) can be obtained.

(d) Substitution and Condensation

The pre-compound (I) having a formylmethylthioacetamido group at the 7β-position can be subjected to an enol-substitution reaction using a phosphorus pentahalogenide, a phosphorus oxyhalogenide, an alkylmercaptane etc. to provide the ultimate product (I) having a vinylthioacetamide group.

The pre-compound (I) having a mercaptoacetamido group can be converted to a halovinylthioacetamide compound of the formula (I) by the reaction with a vinylene dihalide in the presence of an aromatic base such as picoline.

The halovinylthioacetamide compound of the formula (I) can be also obtained by the reaction of the pre-compound (I) having a haloacetamido group at the 7β-position with a halothioacetaldehyde in the presence of a base. In the same manner, trifluoromethylthioacetaldehyde or an alkylthioacetaldehyde can be reacted with the haloacetamido pre-compound (I) to produce the corresponding vinylthioacetamide compound of the formula (I).

Treatment of the pre-compound (I) having a protected carboxymethylenedithiethanecarboxamido or a trialkylsilyl-substituted protected carboxymethylenedithiethanecarboxamido group with a halogenating agent yields the corresponding protected carboxyhalomethylenedithietanecarboxamide of the formula (I).

Each of the starting materials to be employed in the reactions described in 6a to 6d can be obtained by the reaction of the aforementioned amine of the formula (II) with a reactive derivative of the carboxylic acid comprising the corresponding acyl group.

An acyl group which constitutes the acylamino group at the 7β-position of the compound (I) can be prepared from the known compound according to a method known per se, for example, a method selected from the followings:

(i) Elimination Reaction

A 1,2-disubstituted ethylthioacetic acid derivative can be converted to the corresponding vinylthioacetic acid derivative by an elimination reaction. As the substituents, there may be exemplified halogen, alkylthio, acyloxy, hydroxy, phosphonium, etc. The elimination is usually carried out by reacting the disubstituted ethylthioacetic acid derivative with a reducing agent such as a combination of a metal and an acid or a combination of a boronhydride complex and an acid in an inert solvent.

The ethylthioacetic acid derivative which bears a leaving group such as halogen, acyloxy, alkoxy or hydroxy at either 1′- or 2′-position and a hydrogen atom at the remaining position can be converted to the corresponding vinylthioacetic acid derivative by the treatment with a base. The base can be selected from a wide variety of strong bases such as DBU, DBN, tertiary amines, etc. and weak bases such as pyridine, picoline, etc.

In the elimination reaction, a dehydrochlorinating agent such as a combination of lithium chloride and dimethylformamide and a dehydrating agent such as a combination of thionyl chloride and a base can also be employed. In addition, pyrolysis can also be used for the elimination.

(ii) Addition

The reaction of an ethynylthio compound or its derivative with an alkyl mercaptane in the presence of a base, preferably a weak base such as an aromatic base, gives an alkylthiovinylthioacetic acid or its derivative. An ethynyl compound, by the reaction with thioglycolic acid or its reactive derivative, can provide a vinylthioacetic acid or its derivative.

(iii) Substitution

When a thioglycolic acid derivative is allowed to react with a vinyl compound substituted by a leaving group, a vinylthioacetic acid derivative can be obtained. This kind of reaction is often an addition-elimination reaction, thought it is seemingly a substitution reaction when whole reaction is considered.

(iv) If the vinylthioacetic acid or its derivative thus prepared has a functional group or groups in the molecule, it may be converted to the other vinylthioacetic acid or its derivative by modifying the functional group or groups according to a procedure known per se.

(7) Protection of carboxylic acid and other reactive functional groups

In carrying out the foregoing various reactions or in converting the compound (I) to the other compound (I), it may be sometimes necessary to protect reactive functional groups other than the reacting group involving in the reaction.

For this purpose, a variety of conventional techniques for the protection are all applicable to the processes of the invention. Such techniques are, for example, disclosed in the literatures, such as J. F. W. McOmie Ed., "Protective Groups in Organic Chemistry", pp183, PLEUM Press, New York, 1973; S. Patai, Ed., "The Chemistry of Functional Groups", pp505, Interscience Publ., John Wiley & Sons Ltd. London, 1969; and Flynn Ed., "Cephalosporins and Penicillins", Academic Press, New York 1972. Typical examples of the protection of reactive functional groups are acylation and etherfication for a hydroxyl group, acylation, enamination and silylation for an amino group, and esterification, amidation and acid anhydridation for a carboxylic acid.

(8) Reaction Conditions

Most of the reactions listed in the above items (1) to (7) are usually carred out at a temperature between −30 and 100° C., particularly, between −20° and 50° C., for 10 minutes to 10 hours in a proper solvent, and if necessary, under anhydrous conditions.

Examples of the solvent employable in the processes of this invention are the following: hydrocarbons (e.g. pentane, hexane, octane, benzene, toluene, xylene), halogenated hydrocarbons (e.g. dichloromethane, chloroform, carbon tetrachloride, dichloroethane, trichloroethane, chlorobenzene), ethers (e.g. diethylether, methyl isobutyl ether, dioxane, tetrahydrofuran), ketones (e.g. acetone, methyl ethyl ketone, cyclohexanone), esters (e.g. ethyl acetate, isobutyl acetate, methyl benzoate), nitro hydrocarbons (e.g. nitromethane, nitro-benzene), nitriles (e.g. acetonitrile, benzonitrile), amides (e.g. formamide, acetamide, dimethylformamide, dimethylacetamide, hexamethylphosphorotriamide), sulfoxides (e.g. dimethyl sulfoxide), carboxylic acids (e.g. formic acid, acetic acid, propionic acid), organic bases (e.g. diethylamine, triethylamine, pyridine, picoline, collidine, quinoline), alcohols (e.g. methanol, ethanol, propanol, hexanol, octanol, benzyl alcohol), water, other industrially available solvents and a mixture thereof.

(a) Work up procedures

An ultimate product (I) of the invention can be isolated from the reaction mixture by any of, or a combination of, the conventional methods such as absorption, elution, distillation, precipitation, concentration, chromatography and the like, after the removal of impurities such as starting materials, by-products and solvents by conventional techniques such as extraction, evaporation, washing, filtration, drying, etc.

Practical and presently preferred embodiments of the invention are illustratively shown in the following Examples and Preparations, wherein physico-chemical data of the products are all listed in Tables I to III; part(s) and % are by weight unless otherwise indicated; Infra Red (IR) and Nuclea Magnetic Resonance (NMR) data are reported by $\nu(cm^{-1})$ and $\delta$(ppm) values (coupling constant J in Hz) respectively; following abbreviations are employed: Me(=methyl), Et(=ethyl), Ph(=phenyl), Ms(=methanesulfonyl), $STetCH_3$(1-methyl-tetrazole-5-yl), THF(=tetrahydrofuran), DMF(=diemthylformamide), Het(=heterocyclic group).

PREPARATION 1

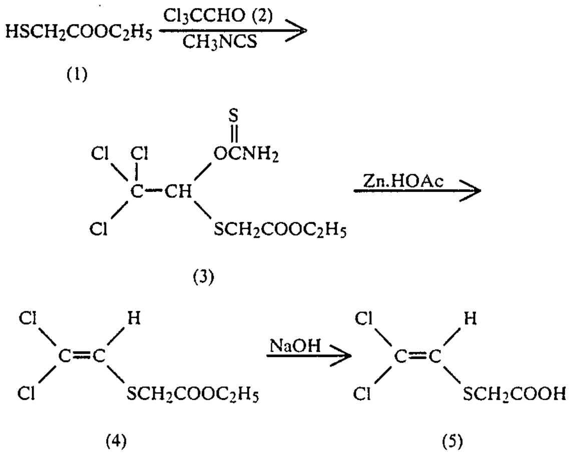

(i) A mixture of chloral (2) (25 g), triethylamine (0.7 ml) and ethyl thioglycolate (1) (18.6 ml) dissolved in benzene (200 ml) is stirred for 1.5 hours. Triethylamine (1.5 ml) and methyl isothiocyanate (10.2 ml) are added thereto and the mixture is stirred for 3 hours. The reaction mixture is poured into water and extracted with ethyl acetate. The extract is washed with water and evaporated to dryness to give ethyl 2-(2,2,2-trichloro-1-thiocarbamoylethyl)thioacetate (3). Yield: 10.4 g.

$NMR(CDCl_3)$: 6.47.

(ii) A mixture of the ethylthioacetate (3) (10.9 g), acetic acid (45 ml) and zinc powder (10 g) is stirred for 20 minutes at room temperature. The reaction mixture is then filtered and the filtrate is vacuum evaporated. The residue is dissolved in dichloromethane, and the resulting solution is washed with water and dried. Evaporation of the solvent gives ethyl chlorovinylthioacetate (4). Yield: 3 g.

$IR(CHCl_3)$: 1725 $cm^{-1}$.

(iii) The thioacetate (4) (1.08 g) dissolved in acetone is hydrolyzed for 30 minutes with addition of a 2N NaOH solution (5 ml). The mixture is then diluted with water, washed with ethyl acetate, acidified and extracted with ethyl acetate to obtain dichlorovinylthioacetic acid (5). Yield: 1.1 g.

$NMR(CDCl_3)$: 3.43 (s,2H), 6.43 (s,1H), 10.17 (s,1H).

PREPARATION 2

$$HOCH_2CH_2SH + ClCH_2COOCH_3 \xrightarrow{K_2CO_3}$$

(1) (2)

$$HOCH_2CH_2SCH_2COOCH_3 \xrightarrow[DBU]{SOCl_2}$$

(3)

$$CH_2{=}CHSCH_2COOCH_3 \xrightarrow[LiCl]{Cl_2}$$

(4)

$$ClCH{=}CHSCH_2COOCH_3 \xrightarrow{NaOH} ClCH{=}CHSCH_2COOH$$

(5) (6)

(i) To a solution of mercaptoethyl alcohol (1) (30.8 g) and $K_2CO_3$ (54.5 g) in water (120 ml) are added ethyl acetate (80 ml) and tetrabutylammonium bromide (0.7 g). Methyl monochloroacetate (2) (38 ml) is dropwise added to the mixture while stirring. After additional stirring for 140 minutes, the organic layer is washed with brine, dried, and vacuum evaporated to give methyl hydroxyethylthioacetate (3) as an oil. Yield: 51.4 g, b.p. 126°-127° C./1 mmHg.

(ii) Thionyl chloride (25 ml) is dropwise added to the ester (3) (47.6 g). After 30 minutes at 30° C., the mixture is distilled in vacuo (b.p. 104°-105° C./7 mmHg, Yield: 43 g). To the distillate are added benzene (82 ml) and DBU (42 ml), and the mixture is heated under reflux for 1.5 hours. The reaction mixture is washed with water and distilled in vacuo to give methyl vinylthioacetate (4). Yield: 24.7 g, b.p. 59°-65.5° C.4-5 mmHg.

(iii) The vinyl ester (4) (11.7 g) is allowed to react with a 1.25N solution of chlorine in $CCl_4$ (75 ml) at −60° C. in methylene chloride. After 15 minutes, the mixture is washed with a sodium sulfite solution and water, and then concentrated. Dimethylformamide (50 ml) and lithium chloride (10 g) are admixed with the residue, and the resulting mixture is warmed at 70° C. for 3 hours. The mixture is diluted with water and extracted with ethyl acetate. The extract is washed with water and distilled in vacuo to give methyl chlorovinylthioacetate (5). Yield: 11.8 g, b.p. 75°-85° C./2 mmHg.

(iv) The chlorovinylthioacetate (5 ) (6.7 g) dissolved in methanol is hydrolyzed by adding of a 3N NaOH aqueous solution. The reaction mixture is acidified and extracted with ethyl acetate to give the corresponding carboxylic acid (6). Yield: 4.2 g, m.p. 65°-66° C. (recrystallized from benzene/hexane).

PREPARATION 3

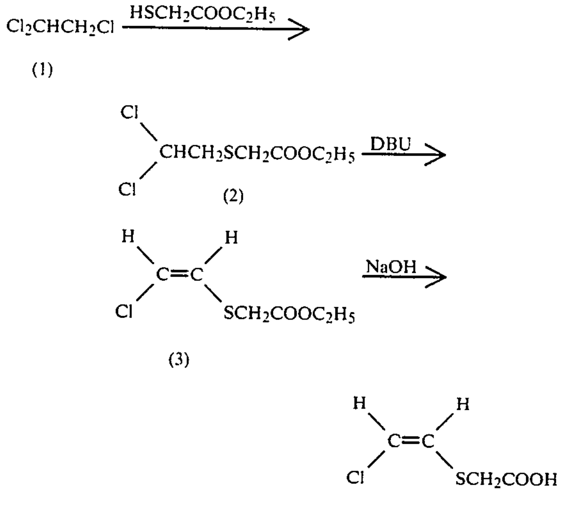

(1) (2) (3) (4)

(i) A mixture of trichloromethane (1) (20 ml), N,N-dimethylformamide (DMF) (20 ml), ethyl thioglycollate (12 ml) and triethylamine (15 ml) is allowed to react at 70° C. for 90 minutes. The reaction mixture is poured into water and extracted with ethyl acetate. The extract is washed with a 5% NaOH solution and water, dried and concentrated. The residue is distilled in vacuo to give ethyl dichloroethylthioacetate (2). Yield: 5.7 g, b.p. 87°-94° C./2 mmHg.

(ii) The ethyl ester (2) (2.17 g) and DBU (1.36 g) are allowed to react in benzene (10 ml) at 80° C. for 30 minutes. The mixture is washed with diluted HCl and brine, concentrated in vacuo and chromatographed over silica gel to give a vinyl compound (3). Yield: 0.45 g.

$IR(CHCl_3)$: 1725 $cm^{-1}$.

(iii) The vinyl compound (3) (1.15 g) dissolved in acetone (10 ml) is hydrolyzed at room temperature for 20 minutes with addition of a 2N NaOH aqueous solution (4.4 ml). The corresponding carboxylic acid is obtained from the reaction mixture in the same manner as Preparation 2.

Yield: 1.2 g.

$IR(CHCl_3)$: 1710 $cm^{-1}$.

PREPARATION 4

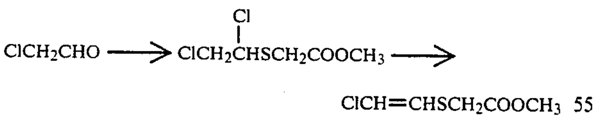

A mixture of a 50% aqueous solution of monochloroacetaldehyde (7.1 ml) and methyl thioglycollate (4.5 ml) is saturated with HCl gas while ice-cooling. After 4 hours, the reaction mixture is extracted with dichloromethane. The extract is washed with water, dried, and concentrated to give methyl (1,2-dichloroethyl)thioacetate (7.19 g), which is dissolved in N,N-dimethylformamide (22 ml). To the solution thus obtained is added lithium chloride (5 g), and the mixture is poured into a mixture of ethyl acetate and water after stirring for one hour at a temperature between 80° and 90° C. The organic layer is separated, washed with water, dried, and vacuum concentrated. After distillation of the residue in vacuo, methyl (2-chlorovinyl)thioacetate is obtained.

Yield: 3.21 g, b.p. 75°-85° C./7 mmHg.

PREPARATION 5

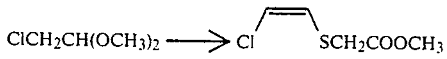

A mixture of chloroacetaldehyde dimethylacetal (14.9 ml), methyl thioglycolate (10.6 g), p-toluenesulfonic acid monohydrate (2 g) and benzene (150 ml) is heated under reflux for 4 hours using a Dean-Stark water separator filled with molecular sieves. After the reaction mixture is poured into water, the organic layer is separated, dried, and concentrated in vacuo. Vacuum distillation of the residue gives methyl 2-chlorovinylthioacetate. Yield: 1.93 g, b.p. 75°-85° C./2 mmHg.

PREPARATION 6

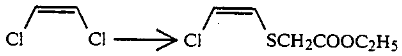

2-Dichloroethylene (21 ml) and DBU (7.5 ml) are added to ethyl thioglycolate (5.5 ml) dissolved in N,N-dimethylformamide (50 ml) under $N_2$ atmosphere. The mixture is allowed to stand at room temperature for 24 hours, poured into water, and extracted with ethyl acetate.

The extract is washed with dil. HCl, a 5% $K_2CO_3$ solution and a saturated NaCl solution, dried, and vacuum evaporated. The residue (7.54 g) is distilled under reduced pressure to give ethyl 2-chlorovinylthioacetate. Yield: 3.67 g (40.8%), b.p. 93° C./3 mmHg.

$NMR(CDCl_3)$: 1.28 (t,3H,J=7 Hz), 3.42 (s,2H), 4.21 (q,2H,J=7 Hz), 6.12 (d,1H,J=6 Hz), 6.50 (d,1H,J=6 Hz).

PREPARATION 7

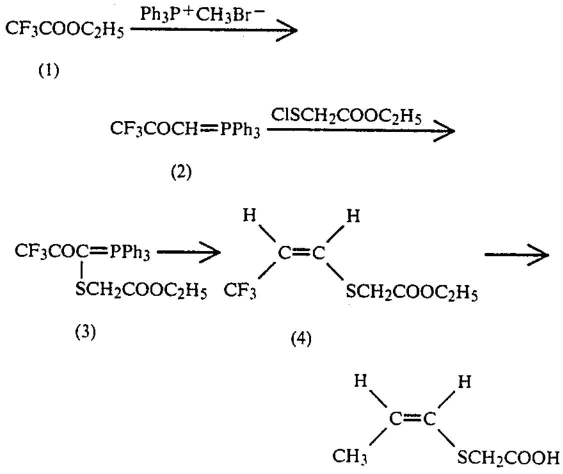

(1) (2) (3) (4) (5)

(i) Methyltriphenylphosphonium bromide (22.4 g) in ethyl ether (300 ml) and 1.4N butyl lithium solution in hexane (44 ml) are admixed at −70° C. and warmed to 0° C. over 30 minutes. Ethyl trifluoroacetate (7.1 ml) is added thereto at $-60°$ C., and the mixture is warmed again to 15° C. over 20 minutes. After the reaction mixture is poured into 2% HCl, precipitated crystals of triphenylphosphoranylidene compound (2) are filtered. Evaporation of the organic layer after washing with water gives the second crop of the product.

Total yield: 8.5 g.

IR($CHCl_3$): 1580 $cm^{-1}$.

(ii) The thus obtained product (2) (3.7 g) is reacted at 0° C. for 10 minutes with ethyl chlorothioacetate which was obtained by reacting di(ethoxycarbonylmethyl)disulfide (1.2 g) with a 1.25N solution of chlorine in $CCl_4$ (4 ml) at $-20°$ C. for 10 minutes in THF as a solvent. The reaction mixture is poured into a $NaHCO_3$ solution and extracted with dichloromethane. The extract is washed with water and the solvent is evaporated off. Recrystallization of the residue from a mixture of dichloromethane and ethyl ether gives ethyl trifluoroacetyltriphenylphosphoranylidenemethylthioacetate (3). Yield: 4 g.

IR($CHCl_3$): 1720, 1555 $cm^{-1}$.

(iii) A mixture of the product (3) (3 g) obtained above and sodium cyanoborohydride (3 g) is stirred in acetic acid (30 ml) at room temperature for 4 hours. After evaporation of the solvent, the residue is poured into a $NaHCO_3$ solution and extracted with ethyl acetate. The extract is washed with water, dried, and evaporated to remove the solvent giving ethyl trifluoromethylvinylthioacetate (4). Yield: 370 mg, IR($CHCl_3$): 1725, 1615 $cm^{-1}$.

(iv) The vinylthioacetate (4) (370 mg) dissolved in methanol (2 ml) is treated with a 1N NaOH solution at room temperature for 20 minutes. The reaction mixture is worked up in a conventional manner to give trifluoromethylvinylthioacetic acid (5). Yield: 278 mg.

NMR($CDCl_3$): 3.47 (s,2H), 5.63 (dg,1H,J=11,9 Hz), 6.77 (d,1H,J=11 Hz), 10.93 (s,1H).

PREPARATION 8

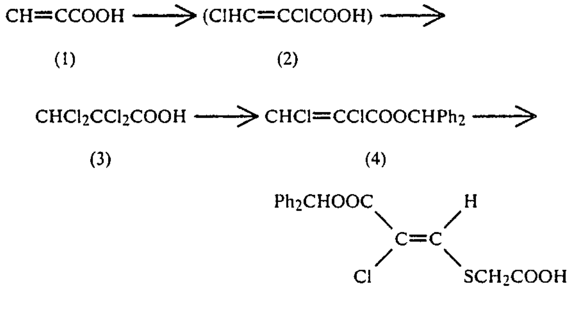
(1) (2) (3) (4) (5)

(i) A mixture of propiolic acid (1) (1.4 g) and 1.48N chlorine in $CCL_4$ (67 ml) is irradiated with a tungsten lamp while ice-cooling. After 30 minutes, the mixture is concentrated under reduced pressure to give tetrachloropropionic acid (3) which has been formed via dichloroacrylic acid (2). Yield: 4.3 g NMR($CCl_4$): 6.27 (s,1H), 10.67 (s,1H).

(ii) The propionic acid (3) (15.3 g), diphenylmethanol (16 g), pyridine (21 ml), methanesulfonyl chloride (9.95 ml) and dichloromethane (100 ml) are admixed together at 0° C. and stirred for 2 hours. The reaction mixture is poured into water and extracted with ethyl acetate. The extract is washed with water and evaporated to remove the solvent. The residue is purified by chromatography over silica gel to give pure diphenylmethyl ester compound (4). Yield: 21 g, m.p. 101°-103° C. (recrystallized from ethyl ether/pentane).

(iii) A mixture of the diphenylmethyl ester (4) (1.53 g), thioglycolic acid (0.7 ml), pyridine (1.6 ml), THF (20 ml) and trimethylsilyl chloride (1.3 ml) is stirred while ice-cooling for 30 minutes and then at room temperature for 20 hours. The reaction mixture is poured into water and extracted with ethyl acetate. The extract is concentrated under reduced pressure, and the residue is dissolved in dichloromethane. The organic solution is washed with water and evaporated to dryness giving diphenylmethoxycarbonyl chlorovinylthioacetic acid (5). Yield: 1.49 g.

IR($CHCl_3$): 3300-3100, 1710 $cm^{-1}$.

PREPARATION 9

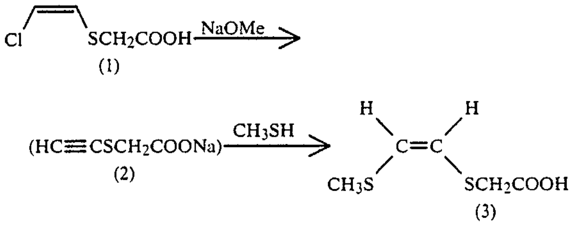

(1) (2) (3)

A mixture of chlorovinylthioacetic acid (1.4 g), a 30% solution of methanethiol in methanol (2.08 ml), a 4.6N sodium methylate solution (5.65 ml) and water (2 ml) is heated under reflux for 40 minutes. The reaction mixture is poured into dil. HCl and extracted with ethyl acetate.

The extract is washed with water and evaporated to remove the solvent giving methylthiovinylthioacetic acid (3).

Yield: 1.3 g.

NMR($CDCl_3$): 2.32 (s,3H), 3.43 (s,2H), 6.15 (s,2H), 11.23 (s,1H).

PREPARATION 10

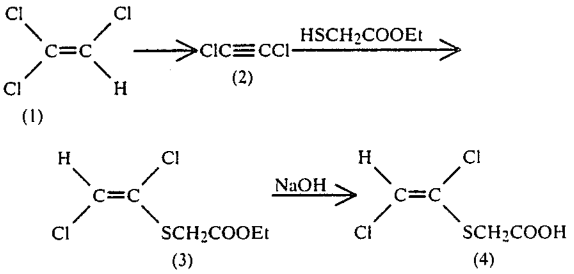

(1) (2) (3) (4)

(i) Trichloroethylene (1) (35 ml), ethyl thioglycolate (9 ml) and sodium ethylate (8 g) are dissolved in ethanol (20 ml). The mixture is heated under reflux for 90 minutes to give ethyl dichlorovinylthioacetate (3) which has been formed via dichloroacetylene (2). Yield: 11.4 g.

IR($CHCl_3$): 1725 $cm^{-1}$.

(ii) To the ethyl ester (3) (0.8 g) dissolved in acetone (8 ml) is added a 2N NaOH solution (2.5 ml). The mixture is stirred at room temperature for 15 minutes, and the neutral portion is removed from the mixture. 1,2-Dichlorovinylthioacetic acid (4) is obtained from the acidic portion. Yield: 0.72 g.

NMR($CDCl_3$): 3.68 (s,2H), 6.40 (s,1H), 10.10 (s,1H).

PREPARATION 11

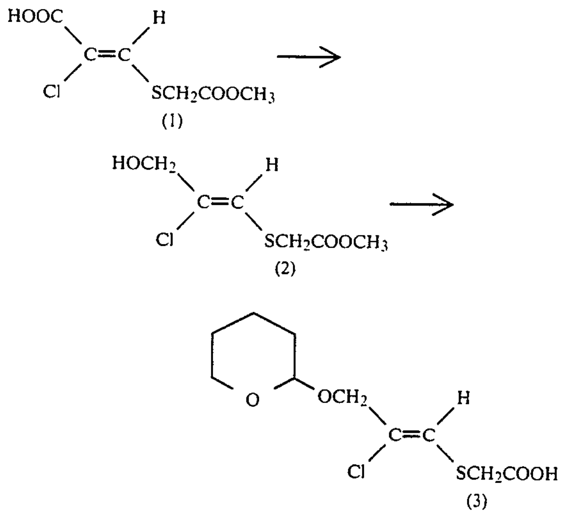

(1) (2) (3)

(i) A mixture of methyl (2-carboxy-2-chlorovinyl)thioacetate (1) (1.48 g), pyridine (0.65 ml), and ethyl chlorocarbonate (0.6 ml) is stirred in THF at −30° C. for 5 minutes and subsequently at 0° C. for 10 minutes. Sodium borohydride (0.8 g) is added thereto, and the mixture is stirred at 0° C. for 2 hours. The reaction mixture is poured into dil. HCl and extracted with ethyl acetate. The ethyl acetate extract is washed with water, concentrated in vacuo, and chromatographed over silica gel to give methyl (2-hydroxymethyl-2-chlorovinyl)thioacetate (2). Yield: 492 mg.

IR($CHCl_3$): 3580, 3460, 1730 $cm^{-1}$.

(ii) The hydroxymethyl compound (2) (490 mg) thus obtained is admixed with dihydropyran (0.25 ml) and p-toluenesulfonic acid monohydrate (5 mg) in dichloromethane (10 ml), and the mixture is stirred at room temperature for 30 minutes. The reaction mixture is poured into a $NaHCO_3$ solution and extracted with ethyl acetate. Concentration of the extract gives a residue which is dissolved in acetone. The acetone solution is stirred at room temperature for 20 minutes with addition of a 1N NaOH solution (2.6 ml). The aqueous solution is diluted with water, acidified with phosphoric acid, and extracted with ethyl acetate. The extract is vacuum evaporated to give the desired tetrahydropyranyloxy compound (3). Yield: 500 mg. Rf(ethyl acetate): 0.15(free acid), Rf(benzene/ethyl acetate=4/1): 0.7(methyl ester)

PREPARATION 12

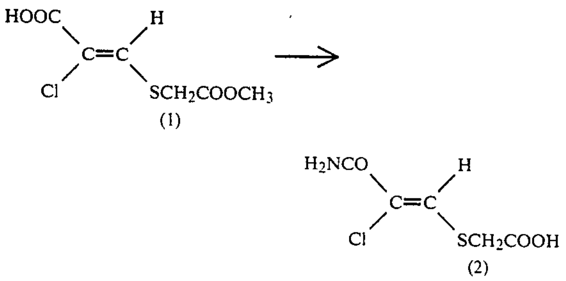

(1) (2)

A mixture of methyl (2-carboxy-2-chlorovinyl)thioacetate (1) (1 g), triethylamine (0.78 ml) and ethyl chlorocarbonate (0.46 ml) is stirred in dichloromethane at −30° C. for 20 minutes. The mixture is added with $NH_3$ (1 g) and stirred at −30° C. to 0° C. The reaction mixture is poured into water and extracted with ethyl acetate. The extract is washed with dil. HCl and concentrated in vacuo. The resulting residue (786 mg) is dissolved in aqueous 70% methanol and hydrolyzed at room temperature for 5 hours with addition of $Na_2CO_3$ (644 mg). The mixture is poured into water and washed with ethyl acetate to remove neutral materials. The aqueous layer is acidified with HCl and extracted with ethyl acetate containing methanol. The extract is vacuum evaporated, and the residue is washed with ethyl ether. Thus, carbamoylchlorovinylthioacetic acid (2) is obtained. Yield: 568 mg, m.p. 205°-206° C.

PREPARATION 13

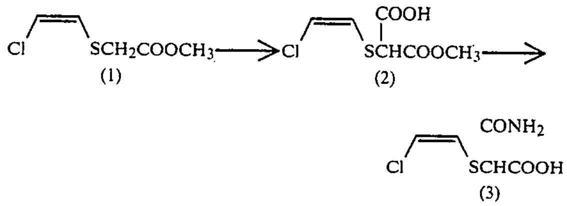

(1) (2) (3)

(i) Methyl (2-chlorovinyl)thioacetate (1) (2 g) and lithium diisopropylamide (1.08 g) are stirred in THF (2 ml) at −60° C. for 15 minutes. After addition of dry ice (5 g), the mixture is stirred for 30 minutes and allowed to warm to room temperature. The reaction mixture is poured into water and washed with ethyl acetate to remove neutral material. The remaining aqueous solution is acidified with HCl and extracted with ethyl acetate. The extract is washed with water and vacuum evaporated to give the desired malonic acid ester (2). Yield: 747 mg.

IR($CHCl_3$): 1725 $cm^{-1}$.

(ii) A mixture of the malonic ester (2) (747 mg), N,N-dimethylformamide (75 mg) and oxalyl chloride (370 μl) is stirred in benzene (10 ml) at room temperature for 20 minutes. The reaction mixture is concentrated in vacuo and the resulting residue is dissolved in dichloromethane (15 ml). The dichloromethane solution is stirred for 15 minutes after addition of liquid ammonia (1 ml). The mixture is vacuum evaporated, and the residue thus obtained is dissolved in ethyl acetate. The ethyl acetate solution is washed with water and dried to give an amide ester (corresponding to the methyl ester of the ultimate compound (3)). Yield: 450 mg.

IR($CHCl_3$): 3480, 3370, 1725, 1690 $cm^{-1}$.

(iii) The amide ester (200 ml) obtained above is dissolved in methanol (3 ml) and hydrolyzed at 35° C. for 1 hour with addition of a 1N NaOH solution (2 ml). The reaction mixture is concentrated in vacuo and the resulting residue is distributed between water and ethyl acetate. The aqueous layer is acidified with HCl and extracted with ethyl acetate. The extract is washed with water and concentrated to give (2-chlorovinyl)thiocarbamoylacetic acid (3). Yield: 100 mg.

PREPARATION 14

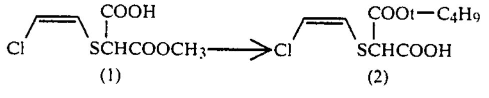

(1) (2)

(i) A mixture of methyl 2-(2-chlorovinyl)thio-2-carboxyacetate (1) (1 mol.), t-butanol (1.2 mol.), pyridine (2.3 mol.) and methanesulfonyl chloride (1.2 mol.) is reacted in dichloromethane (5 part by weight of the starting material (1)) at 0° C. for 3 hours. The acidic portion is separated from the reaction mixture and purified to give t-butyl methyl (2-chlorovinyl)thiomalonate (corresponding to the methyl ester of the desired product (2)). Yield: 73%.

NMR($CDCl_3$): 1.5 (s,9H), 3.81 (s,3H), 4.28 (s,1H), 6.21 (d,1H,J=7 Hz), 6.64 (d,1H,J=7 Hz).

(ii) t-Butyl methyl (2-chlorovinyl)thiomalonate obtained above (1.2 mol.) dissolved in aqueous methanol is hydrolyzed at 0° C. for 4 hours with addition of KOH (1.2 mol.). The neutral portion is removed from the reaction mixture and the acidic material is purified to give 2-(2-chlorovinyl)thio-2-t-butoxycarbonylacetic acid (3). Yield: 94%.

NMR($CDCl_3$): 1.51 (s,9H), 4.30 (s,1H), 6.18 (d,1H,J=7 Hz), 6.63 (d,1H,J=7 Hz), 10.49 (s,1H).

PREPARATION 15

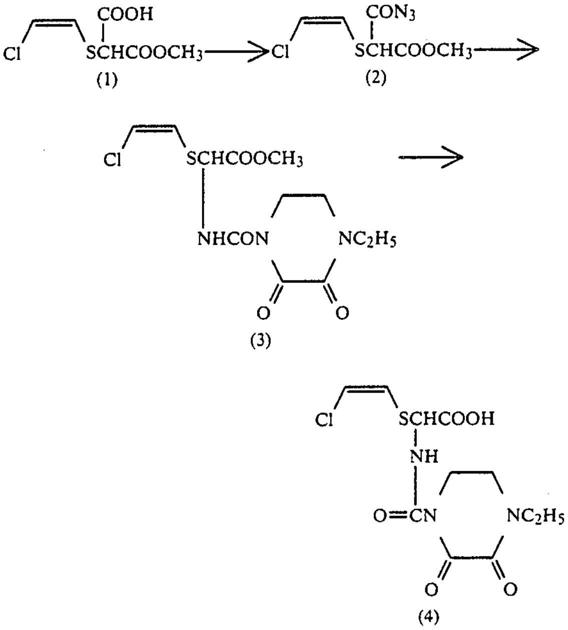

(1) (2) (3) (4)

(i) A mixture of methyl 2-(2-chlorovinyl)thio-2-carboxyacetate (1) (450 mg), oxalyl chloride (325 mg) and dimethylformamide (50 mg) is stirred in dichloromethane (2 ml) at room temperature for 30 minutes. To the mixture is added a solution of sodium azide (550 mg) dissolved in acetone (2 ml) and water (2 ml). The mixture is stirred for 30 minutes, diluted with dichloromethane, washed with water, and cencentrated in vacuo to give azide (2). Yield: 430 mg.

NMR($CDCl_3$): 3.80 (s,3H), 4.40 (s,1H), 6.23 (d,1H,J=7 Hz), 6.63 (d,1H,J=7 Hz).

(ii) The azide (2) (510 mg) thus obtained is admixed with 1-ethyl-2,3-dioxopiperazine (750 mg) and THF (10 ml), and the mixture is heated under reflux for 4 hours. The reaction mixture is vacuum evaporated to give ureido ester (3). Yield: 400 mg.

IR($CHCl_3$): 3250, 1720, 1690 $cm^{-1}$.

(iii) The ureido ester (3) (400 mg) dissolved in acetic acid (2 ml) is hydrolyzed at 50° C. to 60° C. for 3 hours with addition of 6N HCl (2 ml), and subsequently concentrated in vacuo. The residue is dissolved in ethyl acetate, and the ethyl acetate solution is washed with water. The acidic material is separated from the solution and purified in a manner as previously described, then ureido carboxylic acid (4) is obtained. Yield: 136 mg. IR(Nujol): 3250, 1700, 1650 $cm^{-1}$.

PREPARATION 16

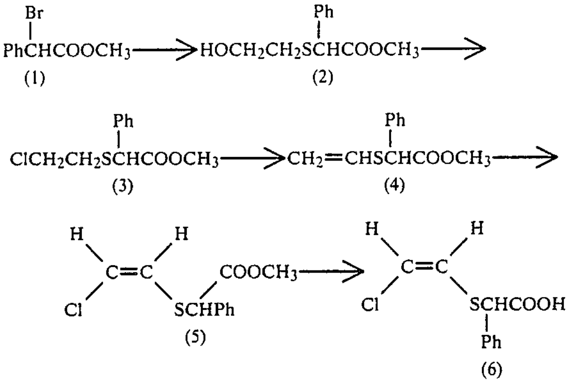

(1) (2) (3) (4) (5) (6)

(i) A mixture of methyl 2-bromoacetate (7.6 g), mercapto ethanol (2.25 ml) and sodium metal (1.5 g) is stirred in methanol (30 ml) at 0° C. for 40 minutes. The reaction mixture is neutralized with HCl/methanol and then vacuum evaporated. Dichloromethane is added to the residue, and precipitated solid is filtered off.

The filtrate is evaporated to dryness under reduced pressure to give a hydroxyethyl compound (2).

Yield: 6 g.

NMR($CDCl_3$): 2.22 (s,1H), 2.73 (t,2H,J=6 Hz), 3.70 (t,2H,J=6 Hz), 3.73 (s,3H), 4.67 (s,1H), 7.23-7.60 (m,5H).

(ii) The hydroxyethyl compound (2) (2.9 g) is combined with thionyl chloride (1.1 ml), and the mixture is stirred at −5° C. to room temperature followed by evaporation under reduced pressure. The resultant residue is purified by chromatography over silica gel to give a chloroethyl compound (3). Yield: 2.6 g.

NMR($CDCl_3$): 2.85 (t,2H,J=7 Hz), 3.53 (t,2H,J=7 Hz), 3.72 (s,3H), 4.65 (s,1H), 7.23-7.60 (m,5H).

(iii) The chloroethyl compound (3) (1.75 g) and DBU (1.25 g) are refluxed in benzene (5 ml) for 2 hours. The reaction mixture is washed with water and vacuum concentrated. The residue is purified by chromatography to give a vinylthio compound (4). Yield: 640 mg.

NMR($CDCl_3$): 3.72 (s,3H), 4.78 (s,1H), 5.12 (d,1H,J=4 Hz), 5.33 (d,1H,J=4 Hz), 6.17, 6.43 (dd,1H,J=10 Hz), 7.17-7.58 (m,5H).

(iv) The vinylthio compound (4) (640 mg) is admixed with a 1.48M solution of chlorine in $CCl_4$ (2.1 ml) and dichloromethane (10 ml), and the mixture is stirred at −40° to −45° C. for 1 hour. The reaction mixture is washed with a sodium thiosulfate solution and water, and concentrated in vacuo. The residue dissolved in dimethylformamide (3 ml) is warmed at 65° C. to 70° C. for 30 minutes with addition of lithium chloride (500 mg). The mixture is diluted with water and extracted with ethyl acetate. By subsequent washing, drying and evaporating of the extract, chlorovinylthio compound (5) is obtained. Yield: 390 mg.

NMR($CDCl_3$): 3.75 (s,3H), 4.82 (s,1H), 6.05 (d,1H,J=6 Hz), 6.32 (d,1H,J=6 Hz), 7.17-7.77 (m,5H).

(v) The chlorovinylthio compound (5) (390 mg) dissolved in methanol is hydrolyzed at 5° to 10° C. for 3.5 hours with addition of a 1N NaOH solution (2 ml) to give the desired carboxylic acid (6). Yield: 260 mg.

MNR($CDCl_3$): 4.82 (s,1H), 6.07 (d,1H,J=6 Hz), 6.35 (d,1H,J=6 Hz), 7.20-7.73 (m,5H), 10.53 (s,1H).

PREPARATION 17

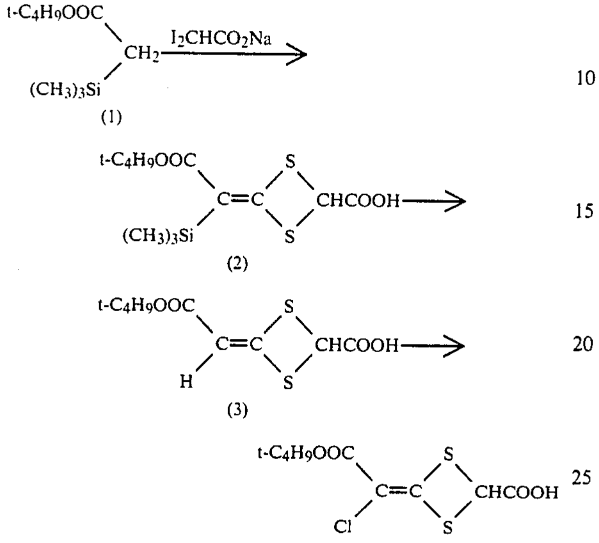

(1) (2) (3) (4)

(i) A mixture of t-butyl trimethylsilylacetate (1) (9.42 g), N-cyclohexyl-N-isopropylamine (10 ml), a 1.68N solution of n-butyl lithium in hexane (33 ml) and dimethoxyethane (400 ml) is stirred at −70° C. for 30 minutes. Carbon disulfide (3.3 ml) is added thereto over 30 minutes while stirring, and the mixture is stirred for additional 20 minutes. The n-butyllithium solution in hexane (33 ml) is dropwise added thereto over 1 hour and stirring is continued for 30 minutes. To the mixture is added sodium iodoacetate which was obtained by the reaction of 50% sodium hydride in petroleum (2.4 g) and iodoacetic acid (15.59 g) in dimethoxyethane (75 ml). After stirring at room temperature for one hour, the reaction mixture is vacuum evaporated and the resulting residue is combined and agitated with ethyl ether (300 ml) and 4N HCl (32 ml). The ether layer is evaporated to dryness giving a trimethylsilyl compound (2).

NMR($CCl_4$): 4.95 (s,1H), 3.87 (s,3H), 1.52 (s,9H), 0.22 (s,9H).

The trimethylsilyl compound (2) is treated with dil. HCl, and the reaction mixture is worked up in a conventional manner to give a methylene carboxylic acid (3).

Yield: 10.13 g.

(ii) The carboxylic acid (3) (5.9 g) is dissolved in dichloromethane (30 ml) and esterified with an excess of diazomethane. The ester thus obtained is dissolved in dichloromethane and combined with pyridine (3.80 ml) and a 1.19M solution of chlorine in $CCl_4$ (27 ml) at −78° C. The reaction mixture is washed with a sodium thiosulfate solution and vacuum concentrated. The resultant residue is purified by chromatography over silica gel to give a chloroethyl compound (corresponding to the methyl ester of the ultimate product (4)). Yield: 4 g.

(iii) Hydrolysis of the chloroethyl compound with a NaOH solution gives the corresponding carboxylic acid (4) in a quantitative yield.

The carboxylic acid (4) is also obtained by methylesterification of the dithietane compound (2) with diazomethane, subsequent treatment of the resulting ester with chlorine in a manner as stated in the above item (ii), and the hydrolysis of the chlorinated compound. Yield: 38%.

NMR($CDCl_3$): 8.17 (s,1H), 4.85 (s,1H), 1.50 (s,9H).

PREPARATION 18

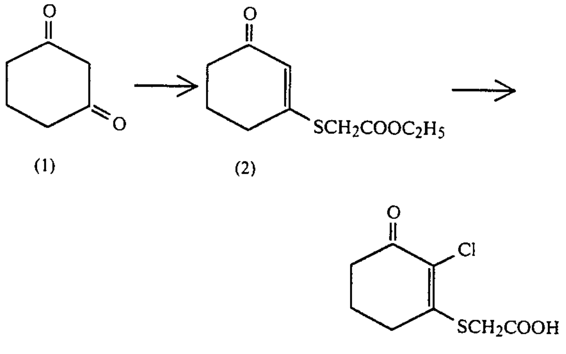

(1) (2) (3)

(i) A mixture of cyclohexane-1,3-dione (1) (3.42 g), ethyl thioglycolate (2.4 g) and p-toluenesulfonic acid mono hydrate (40 mg) is heated under reflux in toluene (20 ml) for 2.5 hours. The reaction mixture is worked up in a conventional manner to give ethyl 3-oxo-1-cyclohexenylthioacetate (2). Yield: 2.8 g.

NMR($CDCl_3$): 1.27 (t,3H,J=8 Hz), 1.95-2.18 (m,2H), 2.33-2.57 (m,4H), 3.63 (s,2H), 4.23 (q,2H,J=8 Hz), 5.88 (bs,1H).

(ii) The obtained acetate (2) (214 mg) is combined with propylene oxide (200 μl) and chlorine (1.2 mol. equivalent with respect to the acetate) in dichloromethane (5 ml) at −70° C. The reaction mixture is vacuum evaporated and the residue is purified by chromatography over silica gel to give the ethyl ester of chlorocarboxylic acid compound (3).

Yield: 120 mg, m.p. 96° C.

The ethyl ester dissolved in ethanol is hydrolyzed at room temperature for 15 minutes with addition of a 1N NaOH solution (1 ml) to give 3-oxo-2-chloro-1-cyclohexene-1-yl-thioacetic acid (3). Yield: 70 mg, m.p. 190° C.

PREPARATION 19

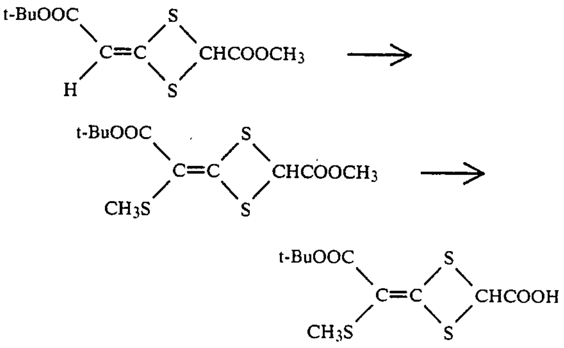

(i) A mixture of methyl 2-(t-butoxycarbonylmethylene)-1,3-dithiethane-4-carboxylate(614 mg), pyridine (300 μl) and methanesulfenyl chloride (equivalent amount of the carboxylate) is allowed to react in dichloromethane until no starting carboxylate is detected. The reaction mixture is washed with a 5% sodium thiosulfate solution and 10% HCl, and subsequently extracted with ethyl acetate. The extract is washed with water, dried, and vacuum evaporated to give methyl 2-(1-t-butoxycarbonyl-1-methylthiomethylene)-1,3-dithietane-4-carboxylate. Yield: 653 mg (91%).

IR($CHCl_3$): 1745, 1700, 1660, 1525 $cm^{-1}$.

NMR($CDCl_3$): 1.50 (s,9H), 2.21 (s,3H), 3.86(s,3H), 4.74 (s,1H).

(ii) The carboxylate thus obtained (495 mg) dissolved in acetone (6 ml) is reacted with a 1N NaOH solution (1.9 ml) for 15 minutes while ice-cooling. The reaction mixture is extracted with ethyl acetate after addition of 1N HCl (2 ml). The extract is washed with water, dried, and evaporated under reduced pressure to give 2-(1-t-butoxycarbonyl-1-methylthiomethylene)-1,3-dithietane-4-carboxylic acid. Yield: 538 mg.

IR($CHCl_3$): 1725, 1700, 1660, 1545 $cm^{-1}$.

NMR($CDCl_3$): 1.51 (s,9H), 2.21 (s,3H), 4.77 (s,1H), 8.7 (broad,1H).

PREPARATION 20

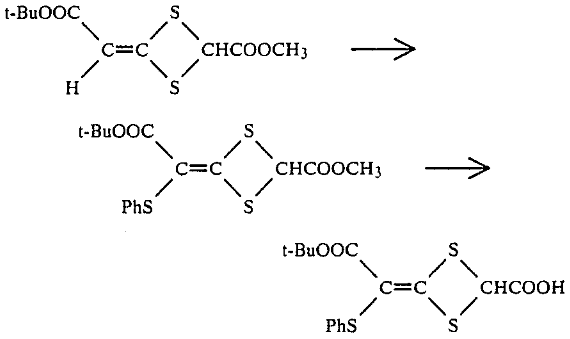

(i) A mixture of methyl 2-(t-butoxycarbonylmethylene)-1,3-dithietane-4-carboxylate (689 mg), pyridine (430 μl) and benzenesulfenyl chloride is allowed to react in methylene chloride at 0° C. until no starting carboxylate is detected. The reaction mixture is washed with water, dried, and vacuum evaporated to give methyl 2-(1-t-butoxycarbonyl-1-phenylthiomethylene)-1,3-dithietane-4-carboxylate. Yield: 713 mg (73%).

IR($CHCl_3$): 1740, 1705, 1660, 1535 $cm^{-1}$.

NMR($CDCl_3$): 1.38 (s,9H), 3.58 (s,3H), 4.76 (s,1H), 7.26 (s,5H).

(ii) The methyl ester thus obtained (635 mg) dissolved in acetone is reacted with a 1N NaOH solution (2 ml) at 0° C. for 37 minutes. The reaction mixture is extracted with ethyl acetate after addition of 1N HCl (2.2 ml). The extract is washed with water, dried, and vacuum evaporated to give 2-(1-t-butoxycarbonyl-1-phenylthiomethylene)-1,3-dithietane-4-carboxylic acid. Yield: 649 mg.

IR($CHCl_3$): 3400, 1730, 1710, 1660, 1530 $cm^{-1}$.

NMR($CDCl_3$): 1.40 (s,9H), 4.78 (s,1H), 7.25 (s,5H).

PREPARATION 21

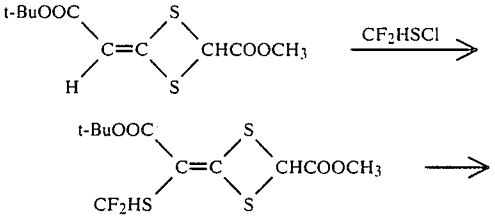

-continued

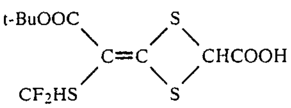

(i) Methyl 2-(t-butoxycarbonylmethylene)-1,3-dithietane-4-carboxylate (1.05 g) is reacted with difluoromethylsulphenyl chloride, which was synthesized from difluoromethyl benzyl thioether (1.74 g) and chlorine, in dichloromethane (5 ml) at room temperature in the presence of pyridine (0.65 ml) until no starting carboxylate is detected in the reaction mixture. The mixture is then washed with a 5% sodium thiosulfate solution and 10% HCl, dried, and concentrated in vacuo to give methyl 2-(1-t-butoxycarbonyl-1-difluoromethylthiomethylene)-1,3-dithietane-4-carboxylate.

Yield: 1.08 g (78%).

IR($CHCl_3$): 1745, 1710, 1665, 1535 $cm^{-1}$.

NMR($CDCl_3$): 1.51 (s,9H), 3.87 (s,3H), 4.79 (s,1H), 6.68 (t,1H,J=59 Hz).

(ii) The product thus obtained (511 mg) dissolved in acetone (2 ml) is reacted with a 1N NaOH solution (1.6 ml) at 0° C. for 10 minutes. The reaction mixture is acidified with 1N HCl and extracted with ethyl acetate. The extract is washed with water and dried to give 2-(1-t-butoxycarbonyl-1-difluoromethylthiomethylene)-1,3-dithietane-4-carboxylic acid. Yield: 503 mg.

NMR($CDCl_3$): 1.51 (s,9H), 4.83 (s,1H), 6.68 (t,1H,J=58 Hz).

PREPARATION 22

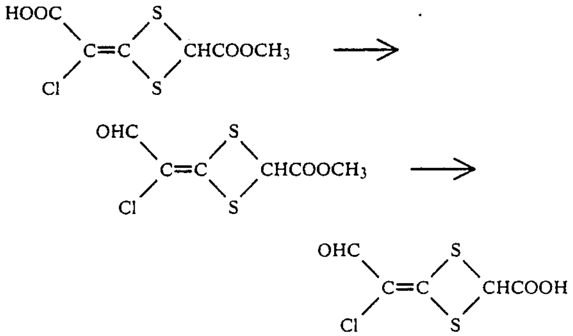

(i) Methyl 2-(1-carboxy-1-chloromethylene)-1,3-dithietane-4-carboxylate (1.29 g) and oxalyl chloride (700 μl) are reacted together in ethyl ether in the presence of N,N-dimethylformamide (50 μl), and the reaction mixture is concentrated under reduced pressure. The resulting residue comprising methyl 2-(1-chlorocarbonyl-1-chloromethylene)-1,3-dithietane-4-carboxylate is dissolved in THF (70 ml) and reacted with lithium tri-t-butoxyalminum hydride (1.36 g) at −78° C. for 30 minutes. The reaction mixture is diluted with a mixture of ethyl acetate and dil. HCl, and the organic layer is separated after vigorous stirring. The separated organic layer is dried, vacuum concentrated, and purified by chromatography over silica gel to give methyl 2-(1-chloro-1-formylmethylene)-1,3-dithietane-4-carboxylate. Yield: 328 mg (27%).

IR($CHCl_3$): 1740 $cm^{-1}$.

NMR($CDCl_3$): 3.88 (s,3H), 5.20 (s,1H), 9.27 (s,1H).

(ii) The carboxylate (262 mg) obtained above is dissolved in acetone and hydrolyzed with addition of a 1N NaOH solution (0.8 ml) to give 2-(1-chloro-1-formylmethylene)-1,3-dithietane-4-carboxylic acid. Yield: 252 mg.

MNR($CDCl_3$): 5.35 (s,1H), 8.98 (s,1H), 9.20 (s,1H).

PREPARATION 23

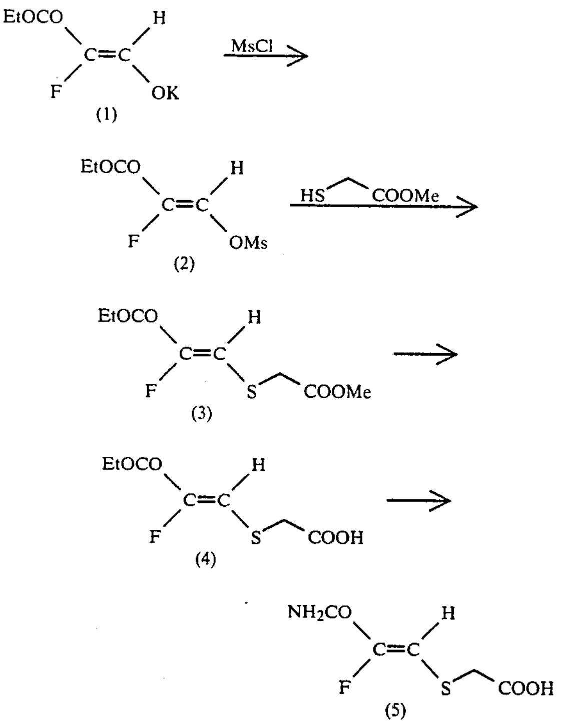

(i) To the potassium salt (1) (3.50 g) dissolved in DMF (30 ml), methanesulfonyl chloride (1.55 ml) is added at room temperature and stirred for 20 minutes. After completion of the reaction, the mixture is poured into water and extracted with ethyl acetate. The extract is washed with water and evaporated to remove the solvent. The residue is purified by chromatography over silica gel to give the oily compound (2). Yield: 2.21 g.

IR($CHCl_3$): 1730, 1680 $cm^{-1}$.

NMR($CDCl_3$): 1.33 (t,3H, J=7 Hz), 3.23 (s,3H), 4.32 (q,2H,J=7 Hz), 7.40 (d,1H,J=16 Hz).

(ii) The compound (2) (2.0 g) obtained above is dissolved in DMF (10 ml), and pyridine (1.5 ml) and methyl mercaptoacetate (1.3 ml) are added thereto. After the mixture is stirred overnight at room temperature, it is poured into ice-water and extracted with ethyl acetate. The extract is purified by chromatography over silica gel to give the compound (3). Yield: 1.38 g.

MNR($CDCl_3$): 1.32 (t,3H,J=7 Hz), 3.52 (s,2H), 3.77 (s,3H), 4.27 (q,2H,J=7 Hz), 6.93 (1H,J=32 Hz).

(iii) To a solution of the above product (3) (1.38 g) dissolved in acetone (7 ml), a 1N NaOH solution (6 ml) is added and stirred at −15° to −5° C. for 40 minutes. The reaction mixture is poured into water and washed with ethyl acetate to remove neutral materials. The aqueous layer is acidified with HCl and extracted twice with ethyl acetate. The extract is washed with water and evaporated to dryness giving the compound (4).

NMR($CDCl_3$): 1.33 (t,3H,J=7 Hz), 3.62 (s,2H), 4.30 (q,2H,J=7 Hz), 6.98 (d,1H,J=32 Hz), 10.45 (brs,1H).

(iv) The compound (4) can also be obtained by the reaction between the compound (2) (1 mol.) and thioglycolic acid (1 mol.) in DMF (5 parts by weight of the compound (2)) in the presence of triethylamine (2 mol.) at 0° to 5° C. for 1 hour. The compound (4) can be recovered from the reaction mixture according to the usual work up procedure. Yield: 80%.

(v) The compound (4) (0.5 g) thus obtained is dissolved in a 28% $NH_4OH$ solution (2 ml), and the solution is allowed to stand overnight at room temperature. The solution is concentrated in vacuo to 1 ml, acidified with conc. HCl, and precipitated crystals of the compound (5) is collected by filtration. Yield: 0.44 g, m.p. 204°-6° C.

IR(Nujol): 3430, 3210, 1710, 1660, 1640, 1610, 1580 $cm^{-1}$.

NMR(DMSO-d6): 3.72 (s,2H), 6.90 (d,1H,J=36 Hz), 7.40-8.10 (m,2H).

PREPARATION 24

(i) 2-Aminoethanol (7 g) is dissolved in methylene chloride (35 ml) under $N_2$ atmosphere, and pyridine (7.5 ml) and dimethylaminopyridine (283 mg) is added thereto at 10° C. Benzyl chloroformate (11.2 ml) is then added to the resultant mixture while stirring. The mixture is stirred at room temperature for 30 minutes, poured into ice-dil.HCl, and extracted with dichloromethane. The extract is washed with a $NaHCO_3$ solution and water, dried, and concentrated under reduced pressure.

The resulting residue is crystallized from a mixture of dichloromethane and ethyl ether to give methyl N-(2-benzyloxycarbonyloxyethyl)xanthate. Yield: 10 g (76%), m.p. 54°-56° C.

UV($\lambda_{max}^{EtOH}$): 252 nm ($\epsilon$=10,500), 271 nm ($\epsilon$=10,800).

IR($CHCl_3$): 3385, 1747 $cm^{-1}$.

NMR($CDCl_3$): 2.62 (s,3H), 4.05 (t,2H,J=5.0 Hz), 4.38 (t,2H,J=5.0 Hz), 5.17 (s,2H), 7.33 (s,6H).

(ii) The xanthate thus obtained (2.85 g) and sodium azide (650 mg) is heated under reflux in acetonitrile (20 ml) for 110 minutes. The reaction mixture is concentrated to about 10 ml, poured into a $NaHCO_3$ solution, and washed with ethyl acetate. The aqueous layer is adjusted to pH 2 with HCl and extracted with ethyl acetate. The extract is washed with water, dried, and evaporated in vacuo. The residue is purified by chromatography over silica gel to give 1-(benzyloxycarbonyloxyethyl)-1H-tetrazole-5-thiol.

UV($\lambda_{max}^{EtOH}$): 247 nm ($\epsilon$=8,500).

IR($CHCl_3$): 3683, 3423, 1748, 1600 $cm^{-1}$.

NMR($CD_3COCD_3$): 4.63 (s,4H), 5.13 (s,2H), 7.38 (s,5H).

EXAMPLE 1

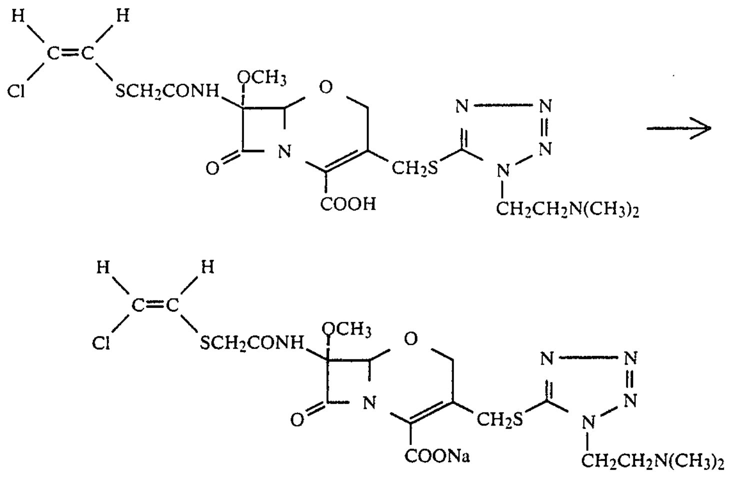

A mixture of 7β-chlorovinylthioacetamido-7α-methoxy-3-(1-dimethylaminoethyl-5-tetrazolyl)thiomethyl-1-dethia-1-oxa-3-cephem-4-carboxylic acid (1 mol.) and a 1.8M solution of sodium 2-ethyl hexanoate in methanol (2.6 mol.) is allowed to react in methanol (7 parts by weight of the starting acid) at room temperature for 10 minutes. Ethyl acetate is added to the reaction mixture, and the resulting precipitates are filtered and washed to give the corresponding sodium salt. Yield: 90–98%.

EXAMPLE 2

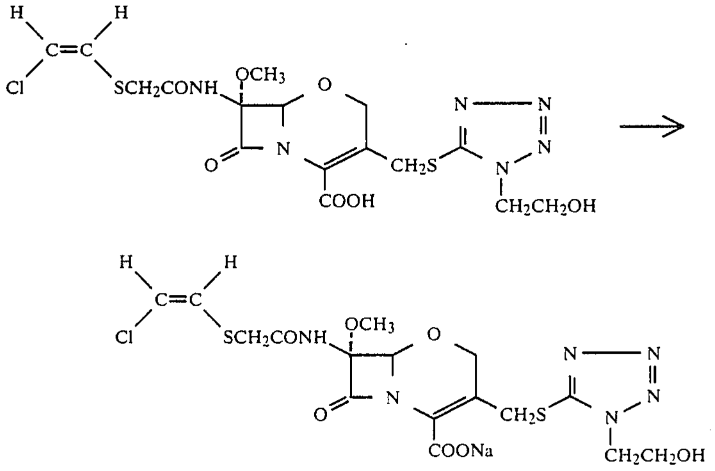

7β-Chlorovinylthioacetamido-7α-methoxy-3-(1-hydroxyethyl-5-tetrazolyl)thiomethyl-1-dethia-1-oxa-3-cephem-4-carboxylic acid (4 g) is dissolved in a $NaHCO_3$ aqueous solution (24 g). The solution is adjusted to pH 6.5 and passed through a column filled with a styrene-divinylbenzene copolymer for the purpose of desalting. The eluate is distributed to four vials and lyophylized in a conventional manner. The corresponding sodium salt is thus obtained.

EXAMPLE 3

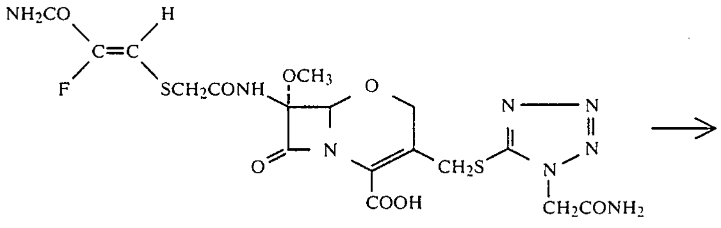

-continued

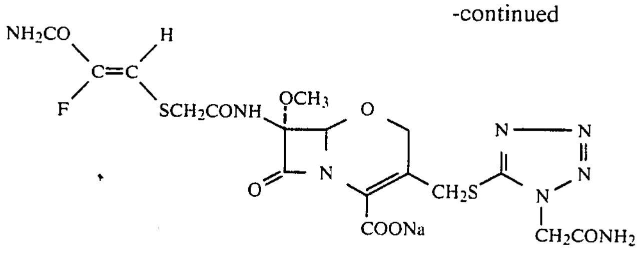

7β-(2-Carbamoyl-2-fluoro)vinylthioacetamido-7α-methoxy-3-(1-carbamoylmethyl-5-tetrazolyl)thiomethyl-1-dethia-1-oxa-3-cephem-4-carboxylic acid (1 g) is dissolved in a 0.5% $NaHCO_3$ aqueous solution (5 ml). The aqueous solution is adjusted to pH 7 with HCl, washed with ethyl acetate, desalted, charged into a 10 ml vial, and lyophilized in a conventional manner. The corresponding sodium salt is thus obtained.

In the same manner as in Example 1, 2 or 3, various light metal salts of the compounds (I) are obtained, which are listed in Table II.

Sodium 7β-(2-carbamoyl-2-fluoro)vinylthioacetamido-7α-methoxy-3-(1-carbamoylmethyl-5-tetrazolyl)thiomethyl-1-dethia-1-oxa-3-cephem-4-carboxylate obtained in Example 2 is dissolved in distilled water for injection (4 g) under sterile conditions. The solution can be intravenously administered twice a day to treat the patients infected with *Staphylococcus aureus.*

Minimum inhibitory concentration values of the salt on *Streptococcus pyogenes* C-203 and *Esherichia coli* JC-2 are less than 0.1 μg/ml and less than 0.1 μg/ml respectively, when measured according to the standard procedure of Nippon Kagaku Ryoho Gakkai (Japan Society of Chemotherapy).

EXAMPLE 4

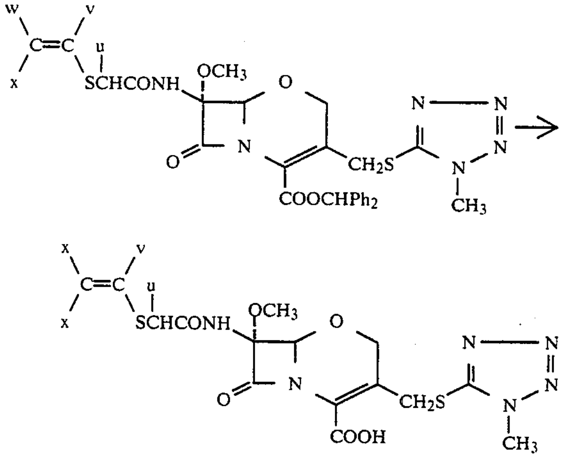

Diphenylmethyl 7β-vinylthioacetamido-7α-methoxy-3-(1-methyl-5-tetrazolyl)thiomethyl-1-dethia-1-oxa-3-cephem-4-carboxylate (1 part), anisole (1 part) and trifluoroacetic acid (0.5 part) are dissolved in dichloromethane (5 parts), and the mixture is stirred while ice-cooling for 30 to 120 minutes. The reaction mixture is concentrated under reduced pressure. The residue is mixed with ethyl ether and stirred to precipitate the corresponding carboxylic acid.

Alternatively, the reaction mixture is poured into a $NaHCO_3$ solution, washed with ethyl acetate, acidified, and extracted with ethyl acetate. The extract is vacuum evaporated, and the resulting residue is agitated in ether to precipitate the carboxylic acid. Yield: 80–98%.

According to the general procedure just mentioned above, the free acids (I) listed in Table II are obtained.

EXAMPLE 5

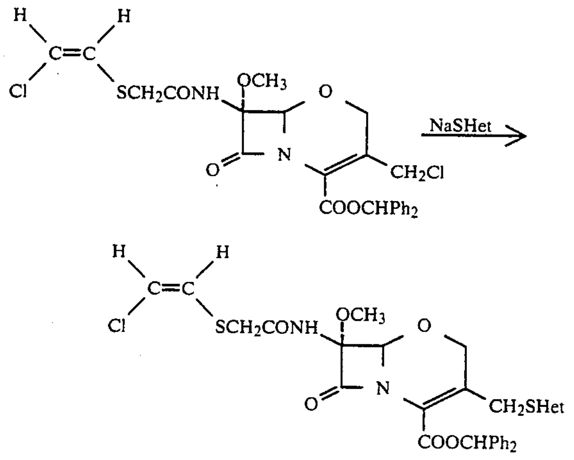

A mixture of diphenylmethyl 7β-chlorovinylthioacetamido-7α-methoxy-3-chloromethyl-1-dethia-1-oxa-3-cephem-4-carboxylate (1 part), a sodium salt of a heterocycic thiol (1.2 mol. equivalent) and DMF (3 to 5 parts) is stirred for 30 minutes. The reaction mixture is poured into water and extracted with ethyl acetate. The extract is washed with water and vacuum evaporated. The resulting residue is purified by chromatography over silica gel to give the corresponding diphenylmethyl 7β-chlorovinylthioacetamido-7α-methoxy-3-heterocyclethiomethyl-1-dethia-1-oxa-3-cephem-4-carboxylate. Yield: 80 to 90%.

EXAMPLE 6

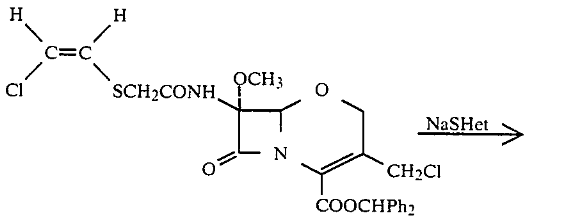

-continued

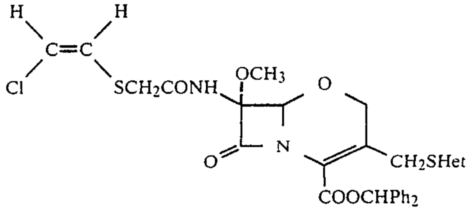

A mixture of diphenylmethyl 7β-chlorovinylthioacetamido-7α-methoxy-3-chloromethyl-1-dethia-1-oxa-3-cephem-4-carboxylate (1 part), a sodium salt of a heterocycle thiol (1.2 mol. equivalent) and dichloromethane (10 to 20 parts) is stirred in the presence of a catalytic amount of tetrabutylammonium bromide at room temperature for 30 minutes to 2 hours. The organic layer is washed with water, dried, and concentrated under reduced pressure. The residue is chromatographed over silica gel to give the desired diphenylmethyl 7β-chlorovinylthioacetamido-7α-methoxy-3-heterocyclethiomethyl-1-dethia-1-oxa-3-cephem-4-carboxylate. Yield: 80 to 90%.

The compounds (I) of the invention prepared by the processes described in the above Examples 5 and 6 are listed in Table III.

EXAMPLE 7

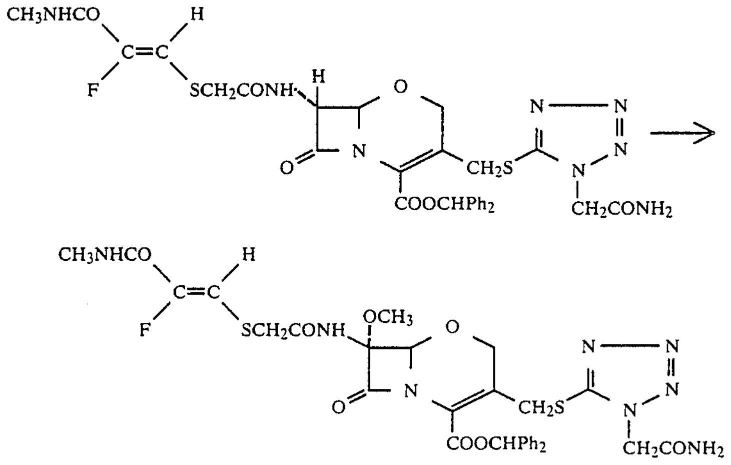

Diphenylmethyl 7α-(2-methylcarbamoyl-2-fluoro)-vinylthioacetamido-3-(1-carbamoylmethyl-5-tetrazolyl)thiomethyl-1-dethia-1-oxa-3-cephem-4-carboxylate (1 part) is dissolved in dichloromethane (10 parts). After addition of t-butylhypochlorite (1.1 mol. equivalent), the mixture is allowed to stand at −20° C. for 3 hours. Lithium methoxide (1.2 mol. equivalent) dissolved in methanol is added thereto, and the mixture is allowed to react for 30 minutes. The reaction mixture is acidified with acetic acid and diluted with dichloromethane. The diluted mixture is washed, dried, and concentrated in vacuo to give the corresponding diphenylmethyl 7β-(2-methylcarbamoyl-2-fluoro)vinylthioacetamido-7α-methoxy-3-(1-carbamoylmethyl-5-tetrazolyl)thiomethyl-1-dethia-1-oxa-3-cephem-4-carboxylate. Yield: 40 to 85%.

According to the above procedure, the compounds (I) listed in Table III are obtained.

EXAMPLE 8

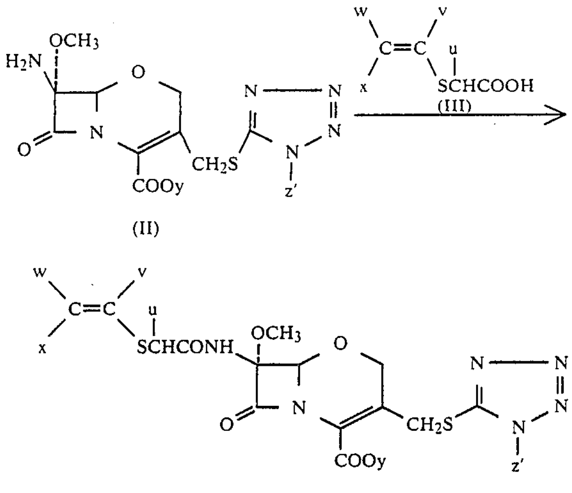

(II)

(I)

($y=CHPh_2$, $z'=CH_3$):

Diphenylmethyl 7β-amino-7α-methoxy-3-(1-methyl-5-tetrazolyl)thiomethyl-1-dethia-1-oxa-3-cephem-4-carboxylate (II) (1 part), pyridine (2 mol. equivalent), phosphorus oxychloride (1.1 mol. equivalent) and a carboxylic acid of the formula (III) (1.1 mol. equivalent) are dissolved in dichloromethane (10 to 15 parts) and allowed to react for 30 minutes while ice-cooling. The reaction mixture is washed with water, dried over $Na_2SO_4$, and concentrated under reduced pressure. The residue is chromatographed over silica gel to give the corresponding diphenylmethyl 7β-acetamido-7α-methoxy-3-(1-methyl-5-tetrazolyl)thiomethyl-1-dethia-1-oxa-3-cephem-4-carboxylate(I). Yield: 70 to 95%.

The compounds (I) of the invention can also be prepared by reacting the amine of the formula (II) with the carboxylic acid of the formula (III) or its reactive derivative according to the general procedures described below. In the following items (1) to (27), part(s) are by volume with respect to the weight of the starting amine (II).

(1) The amine (II) wherein y is H(1 mol.) is dissolved in water (10 parts) containing $NaHCO_3$ (2.5 mol.). An acid chloride derivative of the compound (III) (1.1 mol.) is dropwise added thereto, and the mixture is allowed to react at a temperature between $-5°$ C. and room temperature for 30 minutes to 2 hours.

(2) The amine (II) wherein y is H (1 mol.) is reacted with trimethylsilyl chloride (1.2 mol.) in the presence of triethylamine (1.2 mol.). The silyl ester of the compound (II) thus obtained is combined with an acid chloride of the compound (III) (1.1 mol.) and pyridine (4 mol.) at $-30°$ C., and the mixture is allowed to react for 30 minutes to 2 hours. The silyl ester is then hydrolyzed with an acid.

(3) The amine (II) (1 mol.) and an acid chloride of the compound (III) (1.2 mol.) is stirred in dichloromethane (20 parts) at $-30°$ to 0° C. for 30 minutes to 2 hours in the presence of picoline (4 mol.).

(4) A mixture of the amine (II) (1 mol.), an acid chloride of the compound (III) (1.1 mol.), ethyl acetate (10 parts) and triethylamine (1.1 mol.) is stirred at 0° to $-20°$ C. for 30 minutes to 3 hours.

(5) A mixture of the amine (II) (1 mol.), a mixed anhydride of the compound (III) formed with isobutoxyformic acid (1 mol.), chloroform (10 parts), dimethoxyethane (10 parts) and pyridine (1.5 mol.) is stirred at $-5°$ to 10° C. for 30 minutes to 6 hours.

(6) A mixture of the amine (II) (1 mol.), a bisanhydride of the compound (III) (1.1 mol.), ethyl acetate (10 parts), 1,2-dichloroethane (10 parts) and N-methylmorpholine (1.5 mol.) is heated under reflux for 10 minutes to 2 hours.

(7) A mixture of the amine (II) (1 mol.), a mixed anhydride of the compound (III) formed with methanesulfonic acid (1.1 mol.) and pyridine (1.5 mol.) is stirred at temperature increasing from 0° C. to room temperature for 1 to 3 hours.

(8) The amine (II) (1 mol.) in DMF (5 parts) is reacted with a Vilsmeier reagent consisting of the carboxylic acid (III) and DMF in the presence of dimethylaniline (1.3 mol.) at room temperature for 1 to 5 hours.

(9) The amine (II) (1 mol.) is reacted in ethyl acetate (10 parts) with a mixed anhydride of the compound (III) formed with diethyl phosphate (1.5 mol.) in the presence of pyridine (1.5 mol.) at 0° to 10° C. for 1 to 5 hours.

(10) The amine (II) (1 mol.) is reacted with a mixed anhydride of the compound (III) formed with phosphorus dichloride (1.1 mol.) in the presence of ethyl acetate (7 parts), dichloromethane (10 parts) and pyridine (1 mol.) at 0° C. to room temperature for 1 to 3 hours.

(11) A mixture of the amine (II) (1 mol.), lutidine (1.5 mol.), dichloromethane (10 ml) and a mixed anhydride of the compound (III) formed with monochloro phosphorusdimethylamide (1.1 to 1.2 mol.) is stirred at 0° to 30° C. for 1 to 4 hours.

(12) A mixture of the amine (II) (1 mol.), carbonyldiimidazole (1.1 mol.), THF (10 parts), dimethylacetamide (5 parts) and the carboxylic acid (III) (1.1 mol.) is stirred at 0° C. to room temperature for 1 to 5 hours.

(13) A mixture of the amine (II) (1 mol.), dichloromethane (10 parts), DMF (5 parts), N,N'-dicyclohexylcarbodiimide (1.1 mol.), picoline (1.2 mol.) and the carboxylic acid (III) (1.1 mol.) is heated for 2 to 24 hours.

(14) A mixture of the amine (II) (1 mol.), dichloromethane (10 parts), 2-ethoxy-1-ethoxycarbonyl-1,2-dihydroquinoline (1.1 mol.), N,N'-dicyclohexylcarbodiimide (1.1 mol.), pyridine (1.5 mol.) and the carboxylic acid (1.1 mol.) is stirred at 0° C. to room temperature for 1 to 6 hours.

(15) A mixture of the amine (II) (1 mol.), dichloromethane (30 parts), cyanuric chloride (1.1 mol.), pyridine (4 mol.) and the carboxylic acid (1.1 mol.) is stirred at $-30°$ to 10° C. for 30 minutes to 2 hours.

(16) A mixture of the amine (II) (1 mol.), dichloromethane (3 parts), phosphorus oxychloride (1.1 mol), pyridine (1.5 mol.) and the carboxylic acid (1.1 mol.) is stirred at $-10°$ to 10° C. for 20 minutes to 2 hours.

(17) The amine (II) (1 mol.) is reacted with trimethylsilyl chloride to form the corresponding N-trimethylsilyl amine. The N-sillylated compound (1 mol.) is treated with a mixture of phosphorus oxychloride (1.5 mol.), the carboxylic acid (III) (1.2 mol.), pyridine (4 mol.) and dichloromethane (5 parts) at 0° C. to room temperature for 30 minutes to 2 hours.

(18) A mixture of the amine (II) (1 mol.), dichloromethane (8 parts), thionyl chloride (1.5 mol.), pyridine (2.5 mol.) and the carboxylic acid (1.1 mol.) is stirred at $-30°$ to 0° C. for 1 to 5 hours.

(19) A mixture of the amine (II) (1 mol.), dichloromethane (20 parts), 1-hydroxybenztriazole (2.1 mol.), N,N'-dicyclohexylcarbodiimide (2.5 mol.) and the carboxylic acid (III) (2 mol.) is stirred at room temperature for 1 to 15 hours.

(20) A mixture of the amine (II) (1 mol.), dichloromethane (5 parts), trifluoroacetic anhydride (1.5 mol.), pyridine (3 mol.) and the carboxylic acid (1.5 mol.) is stirred at 0° C. to room temperature for 1 to 5 hours.

(21) A mixture of the amine (II) (1 mol.), di(2-pyridyl)sulfide (1.1 mol.), triphenylphosphine (1.1 mol.) and the carboxylic acid (III) (1.1 mol.) is stirred at 10° to 50° C. for 2 to 6 hours.

(22) A mixture of the amine (II) (1 mol.), dichloromethane (3 parts), 1,3,5-tripyridiniumtriazine trichloride (4 mol.) and the carboxylic acid (III) (1.1 mol.) is stirred at $-10°$ to 10° C. for 1 to 5 hours.

(23) A mixture of the amine (II) (1 mol.), $CCl_4$ (30 parts), N-methylmorpholine (1.5 mol.), trisdiethylaminophosphine (1.1 mol.) and the carboxylic acid (III) (1.1 mol.) is allowed to stand at $-20°$ to 10° C. for 1 to 5 hours.

(24) A mixture of the amine (II) (1 mol.), dioxane (10 parts), N,N'-dicyclohexylcarbodiimide (2 mol.) and a phthalimide of the carboxylic acid (III) (2 mol.) is stirred at 10° to 50° C. for 2 to 8 hours.

(25) A mixture of the amine (II) (1 mol.), methyl isobutyl ketone (10 parts), N,N'-dicyclohexylcarbodiimide (1.5 mol.) and a succinimide of the compound (III) (1.5 mol.) is stirred at 0° to 40° C. for 2 to 9 hours.

(26) A mixture of the amine (II) (1 mol.), dichloromethane(20 parts), pyridine (3 mol.), N,N'-dicyclohexylcarbodiimide (3 mol.) and a 1-oxybenztriazole ester of the carboxylic acid (III) (3 mol.) is stirred at 10° to 50° C. for 5 to 30 hours.

(27) A mixture of the amine (II) (1 mol.), chloroform (3 parts), toluene (1 part), picoline (2 mol.), oxalyl chloride (1 mol.) and the carboxylic acid (1.1 mol.) is stirred at $-50°$ to 10° C. for 10 minutes to 2 hours.

The compound (I) prepared according to the above procedures are listed in Tables II and III.

EXAMPLE 9

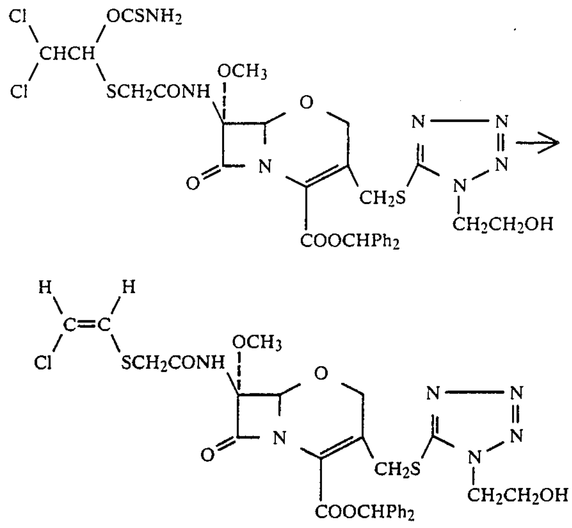

Diphenylmethyl 7β-(2,2-dichloro-1-thiocarbamoyloxyethyl)thioacetamido-7α-methoxy-3-[1-(hydroxyethyl)-5-tetrazolyl]thiomethyl-1-dethia-1-oxa-3-cephem-4-carboxylate (1.5 g) is combined with zinc powder (0.75 g), dioxane (5 ml) and acetic acid (1 ml), and the mixture is stirred at room temperature for 20 minutes. The reaction mixture is filtered. The filtrate is diluted with dichloromethane, washed with water, and concentrated in vacuo to give diphenylmethyl 7β-chlorovinylthioacetamido-7α-methoxy-3-[1-(hydroxyethyl)-5-tetrazolyl]thiomethyl-1-dethia-1-oxa-3-cephem-4-carboxylate. Yield: 40%.

EXAMPLE 10

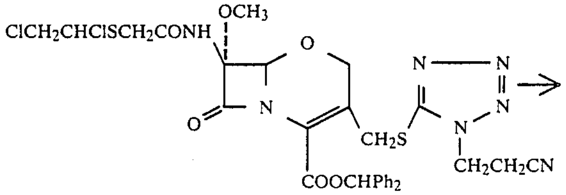

-continued

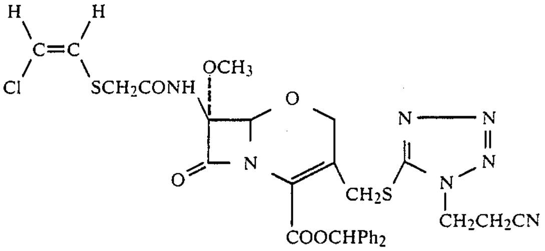

A mixture of diphenylmethyl 7β-(1,2-dichloroethyl)thioacetamido-7α-methoxy-3-(1-cyanoethyl-5-tetrazolyl)thiomethyl-1-dethia-1-oxa-3-cephem-4-carboxylate (4.2 g), lithium chloride (3 g) and DMF (20 ml) is heated at 70° to 75° C. for 3 hours. The reaction mixture is diluted with ice-water and extracted with ethyl acetate. The extract is washed with water, dried, evaporated under reduced pressure to give diphenylmethyl 7β-chlorovinylthioacetamido-7α-methoxy-3-(1-cyanoethyl-5-tetrazolyl)thiomethyl-1-dethia-1-oxa-3-cephem-4-carboxylate. Yield: 2.5 g.

EXAMPLE 11

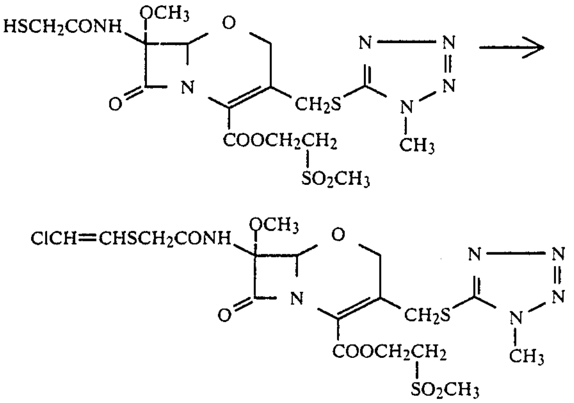

Methanesulfonylethyl 7β-mercaptoacetamido-7α-methoxy-3-(1-methyl-5-tetrazolyl)thiomethyl-1-dethia-1-oxa-3-cephem-4-carboxylate is dissolved in dichloromethane. The solution is combined with an ether solution containing an excess amount of chloroacetylene at −70° C. The temperature of the reaction mixture is allowed to rise to room temperature over 3 hours, washed with water, and evaporated in vacuo to give methanesulfonylethyl 7β-chlorovinylthioacetamido-7α-methoxy-3-(1-methyl-5-tetrazolyl)thiomethyl-1-dethia-1-oxa-3-cephem-4-carboxylate. Yield: 63%.

EXAMPLE 12

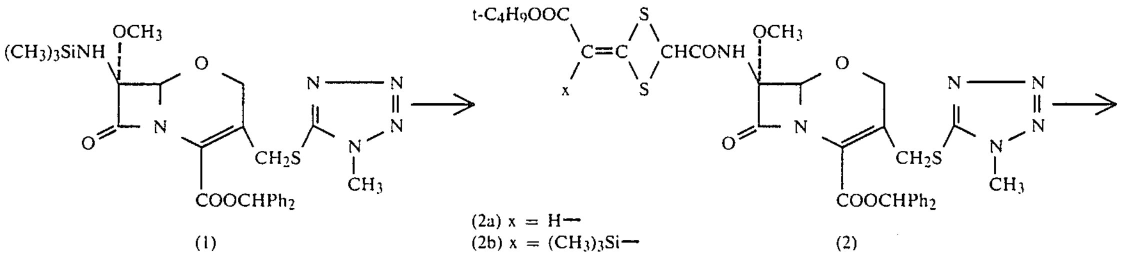

(1)

(2a) x = H—
(2b) x = $(CH_3)_3Si$—

(2)

-continued

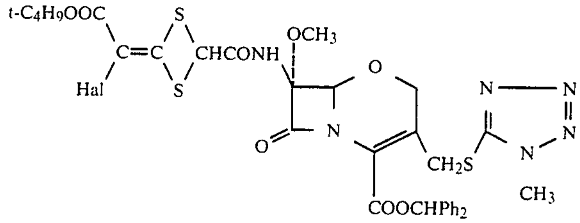

(3)

A. [x=H—]

(i) A mixture of diphenylmethyl 7β-trimethylsilylamino-7α-methoxy-3-(1-methyl-5-tetrazolyl)thiomethyl-1-dethia-1-oxa-3-cephem-4-carboxylate (1) (1 part), phosphorus oxychloride (1.5 mol.), t-butoxycarbonylmethylene-1,3-diethanecarboxylic acid (1.2 mol.) and γ-picoline (1.5 mol.) is stirred in dichloromethane (5 parts) at 0° C. for 30 minutes. The reaction mixture is washed with water, dried, evaporated in vacuo to give diphenylmethyl 7β-t-butoxycarbonylmethlenedithiethanecarbonylamino-7α-methoxy-3-(1-methyl-5-tetrazolyl)thiomethyl-1-dethia-1-oxa-3-cephem-4-carboxylate (2). Yield: 60.7%.

(ii) The product obtained above (1 part) is dissolved in dichloromethane (20 parts). To the dichloromethane solution cooled to −50° C. are added a 1.2M chlorine solution in $CCl_4$ (2.5 mol.) and pyridine (2 mol.). After stirring for 30 minutes, the reaction mixture is warmed to room temperature, washed with a sodium thiosulfate aqueous solution, and concentrated under reduced pressure. The residue is purified by chromatography over silica gel to give diphenylmethyl 7β-t-butoxycarbonylchloromethylene-1,3-dithiethanecarbonylamino-7α-methoxy-3-(1-methyl-5-tetrazolylthiomethyl-1-dethia-1-oxa-3-cephem-4-carboxylate ((3), Hal=Cl). Yield: 57%.

(iii) When bromine is used instead of chlorine in the above reaction, the corresponding 7β-t-butoxy-carbonylbromomethylene compound ((3), Hal=Br) is obtained. Yield: 87%.

(iv) The product obtained in the above item (i) (1 part) is admixed with pyridine (2 mol), hexamethylphosphorotriamide (2 mol.) and N-iodosuccinimide (3 mol.). The mixture is stirred at room temperature, washed with water, and concentrated in vacuo. The residue is purified by chromatography over silica gel to give diphenylmethyl 7β-t-butoxycarbonyliodomethylenedithiethanecarboxyamino-7α-methoxy-3-(1-methyl-5-tetrazolyl)thiomethyl-1-dethia-1-oxa-3-cephem-4-carboxylate ((3), Hal=I). Yield: 80%.

(v) In the same manner as described above, bromomethylene ((3), Hal=Br) or chloromethylene compound ((3), Hal=Cl) is obtained by using respectively N-bromosuccinimide or N-chlorosuccinimide instead of N-iodosuccinimide. Yield: 70%(Br), 75%(Cl).

B. [x=$(CH_3)_3Si$—]

The halomethylene compounds (3) can also be prepared from trimethylsilylmethylene compound (2b) under the same conditions as stated in A.(i) to A.(v).

The compounds (I) prepared by the methods described in Examples 9 to 12 are listed in Tables II and III.

EXAMPLE 13

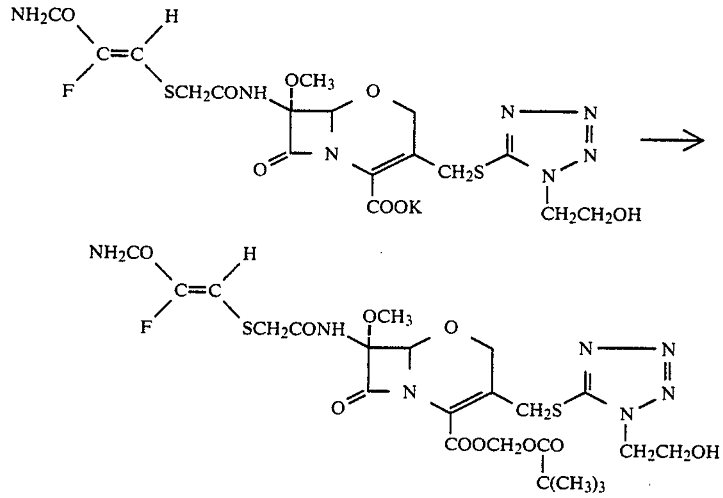

(i) Potassium 7β-(2-carbamoyl-2-fluoro)vinylthioacetamido-7α-methoxy-3-(1-hydroxyethyl-5-tetrazolyl)thiomethyl-1-dethia-1-oxa-3-cephem-4-carboxylate (1 mmol.) is dissolved in DMF (2 to 5 parts). To the solution is added iodomethyl pivalate (1 to 2 mmol.) while ice-cooling, and the mixture is stirred for 15 minutes to 2 hours. The reaction mixture is diluted with ethyl acetate, washed with ice-water and a $NaHCO_3$ solution, dried, and evaporated under reduced pressure. By crystallizing the resultant residue from ethyl acetate, pivaloyloxymethyl 7β-(2-carbamoyl-2-fluoro)vinylthioacetamido-7α-methoxy-3-(1-hydroxyethyl-5-tetrazolyl)thiomethyl-1-dethia-1-oxa-3-cephem-4-carboxylate is obtained.

(ii) The pivaloyloxymethyl ester obtained above can also be produced by using a sodium salt instead of the potassium salt in the same conditions as above.

(iii) The pivaloyloxymethyl ester (250 g), corn starch (150 g) and magnesium stearate (5 g) are uniformly admixed, granulated, and filled in gelatin capsules in a conventional manner so that one capsule may contain 250 mg of the pivaloyloxymethyl ester.

The capsule can be orally administered to patients for the treatment of *Streptococcus pyogenes* infections. Daily posology is 3 to 9 capsules which may be usually divided into three times.

EXAMPLE 14

Sodium salt of 7β-chlorovinylthioacetamido-7α-methoxy-3-(1-dimethylaminoethyl-5-tetrazolyl)thiomethyl-1-dethia-1-oxa-3-cephem-4-carboxylic acid (100 mg) in a 5 ml vial is dissolved in sterillized water for injection (1 ml) before use, and given to an adult patient suffering from pyelitis by way of intravenus injection.

EXAMPLE 15

Lyophilizate from a solution of 7β-(2-carbamoyl-2-fluoro)vinylthioacetamido-7α-methoxy-3-(1-hydroxyethyl-5-tetrazolyl)thiomethyl-1-dethia-1-oxa-3-cephem-4-carboxylic acid (1 g) neutralized to pH 7.0 with sodium hydrogen carbonate is placed in a 150 ml vial. The lyophilizate is dissolved in sterilized water for injection (100 ml) and dripped intravenously to an adult patient immediately after or during a surgical operation of cancer for preventing and treating post operative bacterial infection.

EXAMPLE 16

Microcrystalline 7β-(2-carbamoyl-2-fluoro)vinylthioacetamido-7α-methoxy-3-(1-carbamoylmethyl-5-tetrazolyl)thiomethyl-1-dethia-1-oxa-3-cephem-4-carboxylic acid (200 mg) in a 5 ml vial is suspended in sterilized water for injection containing 2 mg of procaine (2 ml), and given intramuscularly to a patient suffering from suppurative inflammation caused by *Staphylococcus aureus.*

EXAMPLE 17

Crystalline pivaloyloxymethyl 7β-(2-carbamoyl-2-fluoro)vinylthioacetamido-7α-methoxy-3-(1-hydroxyethyl-5-tetrazolyl)thiomethyl-1-dethia-1-oxa-3-cephem-4-carboxylate (200 mg) is dissolved in sesame oil (0.25 ml) and filled in a hard gelatin capsule. Each one capsule is given orally at 4 hour intervals to a patient suffering from upper respiratory tract infection caused by *Streptococcus pyogenes.*

EXAMPLE 18

Powdered 7β-chlorovinylthioacetamido-7α-methoxy-3-(1-hydroxyethyl-5-tetrazolyl)thiomethyl-1-dethia-1-oxa-3-cephem-4-carboxylic acid (100 mg) is mixed well with corn starch (150 mg) and talc (10 mg), powdered, and encapsulated in a hard gelatin capsule (250 mg volume). Each one capsule is administered orally at 3 hour intervals to an adult patient suffering from urinary tract infection caused by *Escherichia coli.*

EXAMPLE 19

Mixed powder of pivaloyloxymethyl 7β-(2-carbamoyl-2-fluoro)vinylthioacetamido-7α-methoxy-3-(1-hydroxyethyl-5-tetrazolyl)thiomethyl-1-dethia-1-oxa-3-cephem-4-carboxylate (10 g), lactose (50 g), corn starch (2 g), magnesium stearate (0.3 g), sucrose (10 g), and necessary amount of acacia and talc is granulated. The granule is mixed with water before use to obtain a suspension, and one teaspoonful amount of the suspension is given orally to an infant suffering from pneumonia caused by *Klebsiella pneumoniae.*

TABLE I

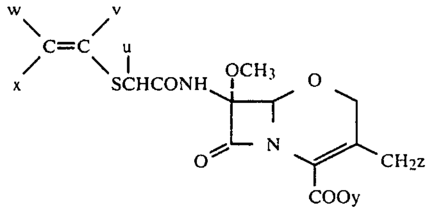

| No. | u | v | w | x | y | z | IR | NMR |
|---|---|---|---|---|---|---|---|---|
| 1-1 | H | H | $NH_2CO$ | F | $CHPh_2$ | Cl | $CHCl_3$: 3390,1780,1715, 1690,1630 mp: 160° C. | $CD_3SOCD_3$: 3.45(s,3H),3.63(s,2H),4.55(bs,4H), 5.23(s,1H),6.93(s,1H),6.97(d,1H, J=32),7.20-7.77(m,13H) |
| 1-2 | H | H | MeNHCO | F | $CHPh_2$ | Cl | $CHCl_3$: 3440,3360,1785, 1720,1690,1635 mp: 178-180° C. | $CD_3SOCD_3$: 2.68(d,3H,J=5),3.47(s,3H),3.65 (s,2H),4.55(bs,4H),5.23(s,1H), 6.93(s,1H),6.67-8.50(m,12H),9.30 (bs,1H) |
| 1-3 | H | H | H | F | $CHPh_2$ | Cl | Nujol: 3250,1776,1720 1680,1654 | DMSO-d6: 3.47(s,5H),4.53(bs,4H),5.05(s,1H) 5.75(dd,1H,J=4.40),6.88(s,1H)6.25 (m,12H) |

TABLE II

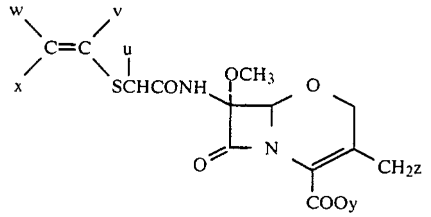

| No. | u | v | w | x | y | z | IR | NMR |
|---|---|---|---|---|---|---|---|---|
| 2-1 | H | H | H | $CF_3$ | Na | STet$CH_3$ | Nujol (y=H): 3200, 1775, 1700, 1670, 1610 | $D_2O$: 3.93(s,3H),4.05(s,2H),4.43(s,3H),4.57 (s,2H),4.95(bs,2H),5.58(s,1H),5.77-6.60 (m,1H),7.25-7.60(m,1H) |
| 2-2 | H | H | H | Cl | H | $OCONH_2$ | | Acetone-d6: 6.67(d,1H,J=7),6.18(d,1H,J=7),5.03(s,1H), 4.98(s,2H),4.48(s,2H),3.56(s,3H) |
| 2-3 | H | H | H | Cl | H | S—2-Indolyl | | Acetone-d6: 8.03(s,1H),7.7-6.6(m,5H),6.15(d,1H,J=7), 5.02(s,1H),6.13(s,2H),4.13+3.83(ABq,2H, J=13),3.75(s,2H),3.56(s,2H),3.45(s,3) |
| 2-4 | H | H | H | Cl | H | 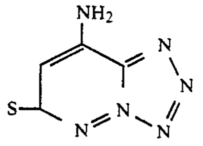 | Nujol: 3300, 1680, 1630 | Acetone-d6: 3.47(s,3H),3.57(s,2H),4.18(d,1H,J=14), 4.67(s,2H),5.10(s,1H),4.83-5.63(m,2H), 6.18(d,1H,J=6),7.03-7.43(m,2H) |
| 2-5 | H | H | H | Cl | H | 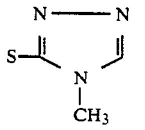 | | Acetone-d6: 3.48(s,3H),3.58(s,2H),3.78(s,3H),4.10(d, 1H,J=13),4.35(d,1H,J=13),4.63(s,2H),5.07 s,1H),6.23(d,1H,J=6.5),6.73(d,1H,J=6.5), 6.92(bs,2H),8.68(s,1H) |
| 2-6 | H | H | H | Cl | H | 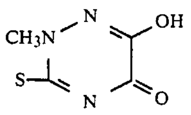 | | Acetone-d6: 3.48(s,3),3.56(s,2H),3.70(s,3H),4.18(d, 1H,J=13),4.45(d,1H,J=13),4.63(s,2H),5.10 (s,1H),4.93-5.67(m,2H),6.23(d,1H,J=7), 6.73(d,1H,J=7),7.93-8.33(m,1H) |
| 2-7 | H | H | H | Cl | H | STet$CH_3$ | Nujol: 3220, 1775, 1705 | Acetone-d6: 3.48(s,3H),3.58(s,2H),4.00(s,3H),4.33(s, 2H),4.67(s,2H),5.10(s,1H),6.23(d,1H,J=6) 6.75(d,1H,J=6),7.22(bs,1H) |
| 2-8 | H | H | H | Cl | Na | STet$CH_3$ | Nujol: 3250, 1760, 1675, 1630, 1600 | $D_2O$: 4.00(s,3H),4.07(s,2H),4.50(s,3H),4.62(bs, 2H),5.02(bs,2H),5.65(s,1H),6.75(d,1H, J=6.5),7.07(d,1H,J=6.5) |
| 2-9 | H | H | H | Cl | H | STet$CH_2CH_2CN$ | | Acetone-d6: 6.75(d,1H,J=7),6.23(d,1H,J=7),5.10(s,1H), 4.73(t,2H,J=7),4.68(s,2H),4.37(s,2H),3.60 (s,2H),3.50(s,3H),3.25(t,2H,J=7) |
| 2-10 | H | H | H | Cl | H | STet$CH_2CH_2$ $CONH_2$ | | DMSO-d6+$CD_3OD$: 3.38(s,3H),3.52(s,2H),3.67-4.65(m,8H), 5.08(s,1H),6.33(d,1H,J=6.5),6.75(d,1H, J=6.5) |
| 2-11 | H | H | H | Cl | H | STet$CH_2CH_2NH_2$ .$CF_3COOH$ | | $D_2O$: 3.88-4.33(m,9H),4.53-4.77(m,2H),5.08-5.22 (m,2H),5.69(s,1H),6.72(d,1H,J=6),7.03(d, 1H,J=6) |
| 2-12 | H | H | H | Cl | H | STet$CH_2CH_2NH$ NH=CH .$CF_3COOH$ | | TLC(Ethyl Acetate:$H_2O$:AcOH=8:1:1): Rf=0.38 |
| 2-13 | H | H | H | Cl | H | STet$CH_2CH_2N$ $(CH_3)_2$ | | $CDCl_3$+$CD_3OD$: 2.87(s,6H),3.50(s,2H),3.52(s,3H),3.63(t, 2H,J=6),4.02+4.18(ABq,2,J=13),4.53(s,2H), 4.77(t,2H,J=6),5.03(s,1H),6.17(d,1H,J=7), 6.62(d,1H,J=7) |

TABLE II-continued

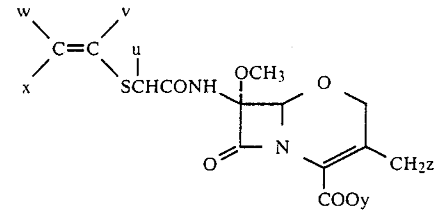

| No. | u | v | w | x | y | z | IR | NMR |
| --- | --- | --- | --- | --- | --- | --- | --- | --- |
| 2-14 | H | H | H | Cl | H | $STetCH_2CH_2$<br>$N(CH_3)_2$<br>$.CF_3COOH$ | KBr: 3420, 1782, 1675 | DMSO-d6: 2.77(s,6H),3.38(s,6H),3.52(s,2H),3.53(t, 2,J=6),4.23(bs,2H),4.55(bs,2H),4.67(t,2H, J=6),5.07(s,1H),6.33(d,1H,J=6),6.75(d,1H, J=6) |
| 2-15 | H | H | H | Cl | Na | $STetCH_2CH_2$<br>$N(CH_3)_2$ | KBr: 3420, 1765, 1685 | $D_2O$: 2.31(s,6H),3.00(t,2H,J=6),3.52(s,3H),3.60 (s,2H),4.20(s,2H),4.54(t,2H,J=6),4.67(bs, 2H),5.16(s,1H),6.28(d,1H,J=6),6.57(d,1H, J=6) |
| 2-16 | H | H | H | Cl | H | $STetCH_2CH_2NH$<br>$HO_3S$ | KBr: 3400, 1780, 1225, 1040 | |
| 2-17 | H | H | H | Cl | H | $STetCH_2CH_2OH$ | Nujol: 3380, 3250, 1770, 1700, 1650, 1630 mp: 99° C. | DMSO-d6: 3.40(s,3H),3.53(s,2H),4.43(t,2H,J=5),4.03-4.93(m,8H),5.08(s,1H),6.35(d,1H,J=6), 6.77(d,1H,J=6),9.73(m,1H) |
| 2-18 | H | H | H | Cl | H | $STetCH_2CH_2OCH_3$ | | TLC(Ethyl Acetate:$H_2O$:AcOH=8:1:1): Rf=0.54 |
| 2-19 | H | H | H | Cl | H | $STetCH_2CH_2O$<br>$ClH_2CCO$ | KBr: 3400, 3270, 1780, 1753, 1721, 1655 | Acetone-d6: 3.49(s,3H),3.57(s,2H),4.21(s,2H),4.34(s, 2H),4.66(s,6H),5.09(s,1H),6.23(d,1H,J=7), 6.72(d,1H,J=7) |
| 2-20 | H | H | H | Cl | H | $STetCH_2CHOH$<br>$CH_2OH$ | Nujol: 3270, 1770, 1700, 1640 | Acetone-d6: 3.48(s,3H),3.58(s,2H),4.33(bs,2H),4.63 (bs,2H),3.50-4.67(m,8H),5.08(s,1H),6.23 (d,1H,J=6),6.75(d,1H,J=6),8.03-8.32(m,1H) |
| 2-21 | H | H | H | Cl | H | $STetCH_2CONH_2$ | Nujol: 3326, 3200, 2723, 1780, 1688, 1635 | Acetone-d6-$CD_3OD$(=1:1): 3.50(s,3H),3.60(s,2H),4.30(s,2H),4.62(s, 2H),5.12(s,1H),5.18(s,2H),6.27(d,1H,J=6), 6.73(d,1H,J=6) |
| 2-22 | H | H | H | Cl | H | 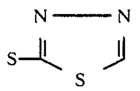 | | TLC(Ethyl Acetate:$H_2O$:AcOH=16:1:1) Rf=0.38 |
| 2-23 | H | H | H | $SCH_3$ | H | $STetCH_3$ | Nujol: 1780, 1710, 1680 | Acetone-d6: 2.30(s,3H),3.48(s,5H),3.98(s,3H),4.32(s, 2H),4.65(s,2H),5.08(s,1H),5.73-6.33(m, 2H),6.20(s,2H) |
| 2-24 | H | H | CN | Cl | H | $STetCH_3$ | | Acetone-d6: 3.50(s,3H),3.92(s,2H),3.98(s,3H),4.37(s, 2H),4.70(s,2H),5.15(s,1H),8.03(s,1H) |

TABLE II-continued

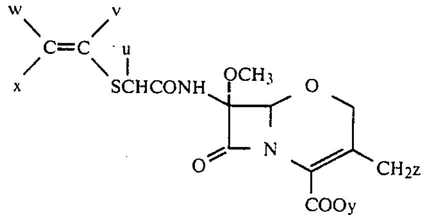

| No. | u | v | w | x | y | z | IR | NMR |
|---|---|---|---|---|---|---|---|---|
| 2-25 | H | H | $CH_2$<br>OH | Cl | H | $STetCH_3$ | Nujol:<br>3250,<br>1770,<br>1670,<br>1620 | $D_2O$:<br>3.97(s,3H),4.07(s,2H),4.50(s,3H),<br>4.63(bs,5H),5.00(s,2H),5.62(s,1H),<br>7.05(s,1H) |
| 2-26 | H | H | CO<br>$NH_2$ | Cl | H | $STetCH_3$ | Nujol:<br>3150,<br>1770,<br>1655 | Acetone-d6:<br>3.50(s,3H),3.83(s,2H),4.00(s,3H),<br>4.36(s,2H),4.67(s,2H),5.10(s,1H),<br>6.96(bs,2H),7.98(s,1H),8.37(bs,1H) |
| 2-27 | H | H | COOH | Cl | H | $STetCH_3$ | KBr:<br>3420,<br>1780,<br>1705 | Acetone-d6:<br>3.50(s,3H),3.80(s,2H),4.02(s,3H),<br>4.35(s,2H),4.68(s,2H),5.13(s,1H),<br>8.15(s,1H) |
| 2-28 | H | H | Cl | Cl | H | $STetCH_3$ | Nujol:<br>3200,<br>1770,<br>1710,<br>1665,<br>1625 | Acetone-d6:<br>3.50(s,3H),3.65(s,2H),4.00(s,3H),<br>4.35(s,2H),4.68(s,2H),5.12(s,1H),<br>6.85(s,1H),6.58-7.08(m,1H) |
| 2-29 | H | $-(CH_2)_3CO-$ | | Cl | H | $STetCH_3$ | Nujol:<br>1782,<br>1710,<br>1678 | DMSO-d6:<br>1.85-2.83(m,6H),3.40(s,3H),3.91(s,<br>3H),4.21(s,2H),4.55(s,2H),5.10(s,<br>1H),7.10(br,1H) |
| 2-30 | H | CN | CN | $SCH_3$ | H | $STetCH_3$ | KBr:<br>3460,<br>3380,<br>3300,<br>2310,<br>1785,<br>1705,<br>1623,<br>1597 | Acetone-d6:<br>6.60(s,2H),5.13(s,1H),4.70(s,2H),<br>4.37(s,2H),4.18(s,2H),4.00(s,3H),<br>3.55(s,3H),2.77(s,3H) |
| 2-31 | H | Cl | H | Cl | H | $STetCH_3$ | Nujol:<br>1765,<br>1705,<br>1670,<br>1625 | Acetone-d6:<br>3.48(s,3H),3.85(s,2H),3.98(s,3H),<br>4.33(s,2H),4.50(s,2H),5.08(s,1H),<br>6.73(s,1H),7.78-8.33(m.2H) |
| 2-32 | Ph | H | H | Cl | H | $STetCH_3$ | KBr:<br>1775,<br>1680 | Acetone-d6:<br>3.32+3.47(each s,all 3H),3.95+3.98<br>(each s, all 3H),4.30(bs,2H),4.58<br>(s,1H),4.67(s,1H),5.08(s,1H),5.20<br>(s,1H),6.20(d,1H,J=7),6.67(d,1H,<br>J=7),7.20-7.70(m,5H),8.30(br,1H) |
| 2-33 | $CONH_2$ | H | H | Cl | H | $STetCH_3$ | | Acetone-d6+$D_2O$:<br>3.50(s,3H),4.00(s,3H),4.35(s,2H),<br>4.67(s,2H),5.12(s,1H),6.32(d,1H,<br>J=6.5),6.83(d,1H,J=6.5) |
| 2-34 | COONa | H | H | Cl | Na | $STetCH_3$ | | TLC(n-BuOH:$H_2O$=7:3):<br>Rf=0.6 |
| 2-35 | 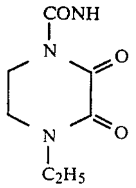 | H | H | Cl | H | $STetCH_3$ | Nujol:<br>3200,<br>1780,<br>1700,<br>1670 | Acetone-d6:<br>1.18(t,3H,J=8),3.52(s,3H),4.00(s,3H)<br>3.5-4.2(m,6H),4.33(s,2H),4.67(s,2H),<br>3.45+3.46(each s,all 1H),5.95(d,1H,<br>J=7),6.22+6.40(d,1H,J=6),6.80(d,1H,<br>J=6),10.06(d,1H,J=7) |
| 2-36 | $N_3$ | H | H | Cl | H | $STetCH_3$ | Nujol:<br>3170,<br>2100,<br>1780,<br>1700 | Acetone-d6:<br>3.52(s,3H),3.98(s,4H),4.33(s,2H),<br>4.68(s,2H),5.12(s,1H),5.07+5.10(each<br>d,all 1H,J=7),6.87(d,1H,J=7) |
| 2-37 | —S— | | $CH_2OH$ | Cl | H | $STetCH_3$ | | Acetone-d6+$CD_3OD$=4:1:<br>3.52(s,3H),4.00(s,2H),4.33(s,2H),<br>4.67(s,2H),5.08(s,1H),5.13(s,1H) |

TABLE II-continued

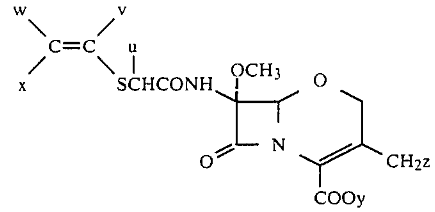

| No. | u | v | w | x | y | z | IR | NMR |
|---|---|---|---|---|---|---|---|---|
| 2-38 | | —S— | CHO | Cl | H | STetCH$_3$ | | Acetone-d6: 3.52(s,3H),3.98(s,3H),4.35(s,2H), 4.68(s,2H),5.17(s,1H),5.63(s,1H), 9.23(s,1H) |
| 2-39 | | —S— | CONH$_2$ | Cl | H | STetCH$_3$ | KBr: 3430, 3330, 3210, 1785, 1700, 1655 | CD$_3$OD−Acetone-d6=1:4: 3.52(s,3H),4.00(s,3H),4.32(s,2H), 4.67(s,2H),5.13(s,1H),5.18(s,1H) |
| 2-40 | | —S— | COOH | F | H | STetCH$_3$ | KBr: 3430, 1785, 1615 | |
| 2-41 | | —S— | COOH | SCH$_3$ | H | STetCH$_3$ | KBr: 1780, 1690, 1520 | CDCl$_3$+CD$_3$OD: 2.23(s,3H),3.58(s,3H),3.95(s,3H), 4.32(s,2H),4.63(s,2H),4.77(s,1H), 5.10(s,1H) |
| 2-42 | | —S— | COOH | SPh | H | STetCH$_3$ | KBr: 1782, 1690 | CDCl$_3$+CD$_3$OD: 3.56(s,3H),3.94(s,3H),4.30(s,2H), 4.60(s,2H),4.79(s,1H),5.09(s,1H), 7.27(s,5H) |
| 2-43 | | —S— | COOH | SCHF$_2$ | H | STetCH$_3$ | KBr: 3440, 1772, 1685 | CDCl$_3$+CD$_3$OD+DMSO-d6: 3.53(s,3H),3.96(s,3H),4.35(s,2H), 4.57(s,2H),5.00(s,1H),5.05(s,1H), 6.89(t,1H,J=59) |
| 2-44 | | —S— | COOH | Cl | H | STetCH$_3$ | KBr: 3430, 1780 | Acetone-d6: 5.25(s,1H),5.12(s,1H),4.67(s,2H), 4.33(s,2H),3.98(s,2H),3,50(s,3H) |
| 2-45 | | —S— | COOH | Cl | H | STetCH$_2$CH$_2$OCO(Cl$_2$CH) | KBr: 3200–3400, 1780, 1700 | Acetone-d6: 3.52(s,3H),4.21(s,2H),4.37(s,2H), 4.66(s,4H),5.14(s,1H),5.27(s,1H), 8.50(s,1H) |
| 2-46 | | —S— | COONa | Cl | Na | 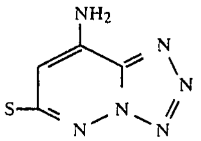 | KBr: 3340, 3190, 1766, 1680, 1635, 1600 | CD$_3$OD: 3.52(s,3H),4.22+4.52(ABq,2H,J=12), 4.53(s,2H),5.03(s,1H),4.87(s,1H), 6.37(s,1H) |
| 2-47 | | —S— | COONa | Cl | Na | STetCH$_3$ | KBr: 1770, 1600 | D$_2$O: 5.60(s,1H),5.45(s,1H),4.98(s,2H), 4.75+4.38(ABq,2H,J=13),4.43(s,3H), 3.95(s,3H) |
| 2-48 | | —S— | COONa | Cl | Na | STetCH$_2$CH$_2$CN | KBr: 3426, 2262, 1764, 1680, 1596 | CD$_3$OD−D$_2$O(4:1): 3.37(t,2H,J=6),3,53(s,3H),4.35(s, 2H),4.55(s,2H),4.93(s,1H),5.08(s,1H) |
| 2-49 | | —S— | ClINa | Cl | Na | STetCH$_2$CH$_2$N(CH$_3$)$_2$ | KBr: 3435, 1768, 1688, 1602 | CD$_3$OD: 2.33(s,6H),2.93(t,2H,J=6),3.53(s, 3H),4.25(s,2H),4.47(t,2H,J=6),4.50 (s,2H),4.87(s,1H),5.02(s,1H) |
| 2-50 | | —S— | COONa | Cl | Na | STetCH$_2$CH$_2$OH | KBr: 3410, 1766, 1680, 1599, 1510 | CD$_3$OD: 3.53(s,3H),3.92(t,2H,J=5),4.31(s, 2H),4.41(t,2H,J=5),4.51(s,2H),4.88 (s,1H),5.03(s,1H), |
| 2-51 | | —S— | COONa | Cl | Na | STetCH$_2$CONH$_2$ | KBr: | CD$_3$OD: |

TABLE II-continued

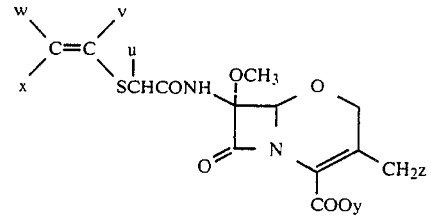

| No. | u | v | w | x | y | z | IR | NMR |
|---|---|---|---|---|---|---|---|---|
| | | | | | | | 3408, 3200, 1768, 1692, 1602 | 3.52(s,3H),4.30(s,2H),4.48(s,2H), 4.88(s,1H),5.03(s,1H),5.12(s,2H) |
| 2-52 | | —S— | COOH | Br | H | $STetCH_3$ | KBr: 3400, 1780 | Acetone-d6: 5.13(s,1H),5.23(s,1H),4.67(s,2H), 4.30(s,2H),3,98(s,3H),3.50(s,3H), |
| 2-53 | | —S— | COOH | I | H | $STetCH_3$ | KBr: 3400, 1780, 1530 | Acetone-d6+$CD_3OD$: 5.16(s,1H),5.13(s,1H),4.67(s,2H), 4.33(s,2H),4.02(s,3H),3.55(s,3H) |
| 2-54 | H | Ph | H | Cl | H | $STetCH_3$ | KBr: 3430, 1780, 1690 | $CD_3OD$: 3.49(s,3H),3.95(s,3H),4.21,4.32 (ABq,2H,J=13),4.61(s,2H),5.05(s,1H), 6.63(s,1H),7.25-7.56(m) |
| 2-55 | H | H | $NH_2CO$ | F | Na | $STetCH_2CH_2OH$ | KBr: 3400, 1770, 1680, 1605 | $D_2O$: 3.97(s,3H),4.17(s,2H),4.33-5.10(m, 8H),5.58(s,1H),7.30(d,1H,J=34) |
| 2-56 | H | H | $NH_2CO$ | F | Na | $STetCH_2CONH_2$ | KBr: 3375, 1765, 1685, 1607 | $D_2O$: 3.97(s,3H),4.15(s,2H),4,50,4.77(ABq, 2H,J=13),4.92(bs,2H),5.57(s,1H),5.70 s,2H),7.27(d,1H,J=34) |
| 2-57 | H | H | $CONHCH_3$ | F | H | $STetCH_2CH{=}CH_2$ | | Acetone-d6: 2.76(d,3H,J=4),3.46(s,3H),3.68(s, 2H),4.37(s,2H),4.67(s,2H),4.9-6.5 (m,6H),6.92(d,1H,J=35),7.5(brs,1H), 8.2(brs,1H) |
| 2-58 | H | H | $CONH_2$ | F | H | $STetCH_2CH{=}CH_2$ | | Acetone-d6: 3.49(s,3H),3.70(s,2H),4.37(s,2H), 4.66(s,2H),4.9-6.2(m,6H),7.0(d,1H, J=36),8.29(s,1H) |
| 2-59 | H | H | H | F | H | $STetCH_2CH{=}CH_2$ | | Acetone-d6: 3.50(s,5H),4.36(s,2H),4117(s,2H), 4.9-6.2(m,5H),5.76(dd,1H,J—42.6), 6.84(dd,1H,J=83.6),8.16(s,1H) |
| 2-60 | H | H | H | F | Na | $STetCH_2CONH$ \| $H_2NCOCH_2$ | | $D_2O$(External Std. $Me_4Si$): 4.00(s,5H),4.46(s,2H),4.67(d,2H, J=6),4.96(s,2H),5.63(s,1H),5.84(s, 2H),6.07(dd,1H,J=39.5),7.35(dd,1H, J=83.5) |
| 2-61 | H | H | H | F | H | $STetCH_2CONH$ \| $H_2NCOCH_2$ | | Acetone-d6: 3.50(s,3H),3.78(s,2H),3.99(d,2H, J=6),4.30(s,2H),4.63(s,2H),5.13(s, 1H),5.30(s,2H),5.77(dd,1H,J=40.4), 6.4-8.3(m,4H) |
| 2-62 | H | H | H | F | Na | $STetCH_2CONH$ \| $H_2NCO$ | | $D_2O$(External Std. $Me_4Si$): 4.00(s,5H),4.66(d,2H,J=3),4.97(s, 2H),5.63(s,1H),5.94(s,2H),6.08(dd, 1H,J=40.4),7.35(dd.1H.J=81.4) |
| 2-63 | H | H | H | F | H | $STetCH_2CONH$ \| $H_2NCO$ | | Acetone-d6: 3.52(s,3H),3.77(s,2H),4.30(s,2H), 4.66(s,2H),5.12(s,1H),5.46(s,2H), 5.76(dd.1H,J=40.5),6.3-8.3(m,5H) |
| 2-64 | H | H | H | F | Na | 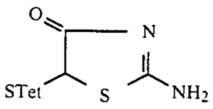 | | $D_2O$(External Std. $Me_4Si$): 4.00(s,5H),4.61+4.79(ABq,2H,J=15), 4.99(s,2H),5.16(s,1H),6.10(dd,1H, J=40.5),7.37(dd,1H,J=84.5),7.73,7.78 (s,total 1H) |

TABLE II-continued

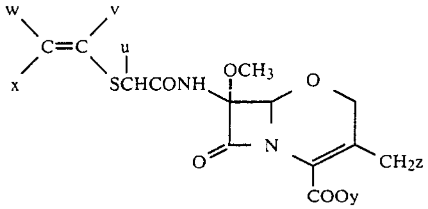

| No. | u | v | w | x | y | z | IR | NMR |
|---|---|---|---|---|---|---|---|---|
| 2-65 | H | H | H | F | H | 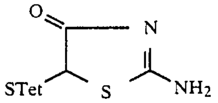 | | Acetone-d6: 3.53(s,3H),3.89(s,2H),4.27+4.45(ABq, 2H,J=12),4.61(s,2H),5.15(s,1H),5.76 (dd,1H,J=86.5),6.3-8.5(m,5H) |
| 2-66 | H | H | $CONHCH_3$ | F | Na | $STetCH_2CH{=}CH_2$ | KBr: 3400, 1767, 1665, 1610 | $D_2O$(External Std. $Me_4Si$): 3.26(s,3H),4.00(s,3H),4.54+4.73(ABq, 2H),J=12),4.8-6.8(m,8H),7.28(d,1H, J=34) |
| 2-67 | H | H | $CONH_2$ | F | Na | $STetCH_2CH{=}CH_2$ | KBr: 3400, 1765, 1685, 1610 | $D_2O$(External Std. $Me_4Si$): 4.00(s,3H),4.17(s,2H),4.55+4.74(ABq, 2H,J=12),4.88+5.02(ABq,2H,J=10),5.4-6.8(m,6H),7.37(d,1H,J=33) |
| 2-68 | H | H | H | F | Na | $STetCH_2CH{=}CH_2$ | KBr: 3420, 1770, 1685, 1610 | $D_2O$(External Std. $Me_4Si$): 3.98(s,3H),4.65(s,2H),4.98(s,2H),5.4-6.7(m,7H),7.39(dd,1H,J=83.5) |
| 2-69 | H | H | $CONH_2$ | F | Na | $STetCH_2CONH$ (with $CH_3$ on N) | KBr: 3400, 1770, 1680, 1610 | $D_2O$(External Std. $Me_4Si$): 3.25(s,3H),3.97(s,H),4.15(s,2H),4.57-4.73(m,2H),4.75(bs,2H),5.60(s,1H), 5.67(s,2H),7.73(d,1H,J=34) |
| 2-70 | H | H | $CONHCH_3$ | F | Na | $STetCH_2CH_2OH$ | KBr: 3400, 1768, 1665, 1610 | $D_2O$(External Std. $Me_4Si$): 3.25(s,3H),3.97(s,3H),4.13(s,2H), 4.33-4.73(m,4H),4.87-5.03(m,4H),5.58 (s,1H),7.25(d,1H,J=34) |
| 2-71 | H | H | H | F | Na | $STetCH_2CONH$ (with $CH_3$ on N) | KBr: 3340, 1767, 1678, 1610 | $D_2O$(External Std. $Me_4Si$): 3.28(s,3H),4.00(s,5H),4.68(bs,2H), 5.00(bs,2H),5.65(s,1H),5.70(s,2H), 6.08(dd,1H,J=4.40),7.36(dd,1H, J=4.82) |
| 2-72 | H | H | H | F | Na | $STetCH_2CH_2OH$ | KBr: 3420, 1770, 1685, 1610 | $D_2O$(External Std. $Me_4Si$): 3.95(s,5H),4.22-5.07(m,8H),5.60(s, 1H),6.08(dd,1H,J=4.40),7.28(dd,1H, J=4.82) |
| 2-73 | H | H | H | F | Na | $STetCH_2CONH_2$ | KBr: 3400, 1766, 1688, 1630 (sh), 1606 | $D_2O$(External Std. $Me_4Si$): 3.63(s,5H),4.47-4.70(m,2H),4.95(bs, 2H),5.25(s,1H),5.38(s,2H),6.03(dd, 1H,J=4.40),7.28(dd,1H,J=4.81) |
| 2-74 | H | H | H | F | Na | $STetCH_2CONH$ (with $HOCH_2CH_2$ on N) | KBr: 3380, 1767, 1678, 1630 (sh), 1605 | $D_2O$(External Std. $Me_4Si$): 3.95(s,5H),3.68-4.25(m,4H),4.53-4.70 (m,2H),4.93(bs,2H),5.58(s,1H),5.70 (s,2H),6.03(dd,1H,J=4.40),7.28(dd, 1H,J=4.82) |
| 2-75 | H | H | H | F | Na | $STetCH_2NHCO$ (with $HOCH_2CH_2NH$ on CO) | KBr: 3380, 1767, 1675, 1630 (sh), 1610 | $D_2O$(External Std. $Me_4Si$): 3.97(s,5H),3.70-4.27(m,4H),4.65(bs, 2H),4.95(bs,2H),5.60(s,1H),5.70(s, 2H),6.03(dd,1H,J=4.40),7.30(dd,1H, J=4.82) |

TABLE II-continued

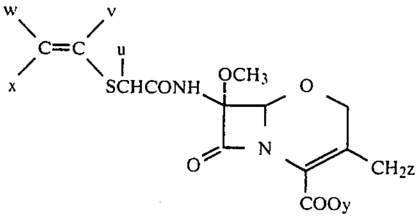

| No. | u | v | w | x | y | z | IR | NMR |
|---|---|---|---|---|---|---|---|---|
| 2-76 | H | H | CO<br>NHCH$_3$ | F | Na | STetCH$_2$CONH$_2$ | KBr: 3400, 1770, 1688, 1614 | D$_2$O(External Std. Me$_4$Si): 3.23(s,3H),4.12(s,2H),4.50–4.70(m,2H), 4.90(bs,2H),5.57(s,1H),5.70(s,2H),7.21 (d,1H,J=34) |
| 2-77 | H | H | CO<br>NHCH$_3$ | F | Na | STetCH$_2$CONH<br>CH$_3$ | Nujol: 3250, 1765, 1670, 1610 | D$_2$O(External Std. Me$_4$Si): 3.23(s,6H),3.95(s,3H),4.13(s,2H),4.53–4.72(m,2H),4.90(bs,2H),5.55(s,1H),5.63 (s,2H),7.20(d,1H,J=34) |
| 2-78 | H | H | H | F | Na | 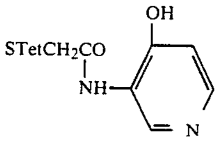 | KBr: 3400, 3250, 1768, 1687, 1632, 1610 | |
| 2-79 | H | H | NH$_2$CO | F | H | STetCH$_2$CH$_2$OH | | CD$_3$COCD$_3$: 3.53(s,3H),3.75(s,2H),3.88–4.77(m,8H), 5.10(s,1H),6.90–7.20(m,2H),7.05(d,1H, J=34),8.10–8.47(m,1H) |
| 2-80 | H | H | NH$_2$CO | F | H | STetCH$_2$CH$_2$OCO<br>OCH$_2$Ph | Nujol: 3300, 1777, 1740, 1680, 1620 | CO$_3$COCD$_3$: 3.50(s,H),3.70(s,2H),4.33(s,2H),4.68(bs, 6H),5.10(s,1H),5.13(s,2H),7.03(d,1H), J=34),6.87–7.17(m,2H),7.37(s,5H),8.20–8.43(m,1H) |

TABLE III

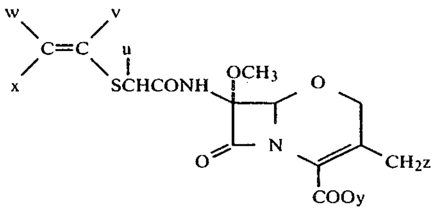

| No. | u | v | w | x | y | z | IR | NMR |
|---|---|---|---|---|---|---|---|---|
| 3-1 | H | H | H | $CF_3$ | CH–$Ph_2$ | STetCH$_3$ | $CHCl_3$: 3350,1785, 1700, | $CDCl_3$: 3.47(bs, 2H), 3.52(s, 3H), 3.70(s, 3H), 4.07-4.33(m, 2H), 4.43-4.77(m, 2H), 5.07(s, 1H), 5.17-5.95(m, 1H), 6.73-6.98(m, 1H), 6.90(s, 1H), 7.07-7.87(m, 11H) |
| 3-2 | H | H | H | Cl | CH–$Ph_2$ | $OCONH_2$ | $CHCl_3$: 3430,1790, 1735,1700 | $CDCl_3$ + Acetone-d$_6$: 7.7-7.0(m, 10H), 6.85(s, 1H), 6.53(d, 1H, J = 7), 6.12(d, 1H, J = 7), 5.18(s, 1H), 5.05(s, 2H), 4.50(s, 2H), 3.55(s, 3H), 3.52(s, 2H) |
| 3-3 | H | H | H | Cl | CH–$Ph_2$ | 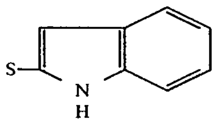 | | $CDCl_3$: 8.42(s, 1H), 7.7-6.9(m, 14H), 6.43(d, 1H, J = 2), 6.37(s, 1H), 6.10(d, 1H, J = 7), 5.96(d, 1H, J = 7), 5.93(s, 2H), 4.93(s, 1H), 3.71 + 3.52(ABq, 2H, J = 12), 3.48(s, 3H), 3.35(s, 2H) |
| 2-4 | H | H | H | Cl | CH–$Ph_2$ | 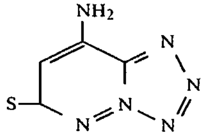 | Nujol: 3320,3180, 1783,1715, 1665,1630 | DMSO—d$_6$: 3.40(s, 3H), 3.48(s, 2H), 3.98 + 4.35(ABq, 2H, J = 14), 4.57(bs, 2H), 5.13(s, 1H), 6.20(s, 1H), 6.25(d, 1H, J = 6), 6.68(d, 1H, J = 6), 6.88(s, 1H), 1H), 7.05-7.70(m, 10H), 7.85(bs, 2H) |
| 3-5 | H | H | H | Cl | CH–$Ph_2$ | 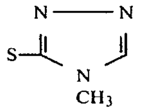 | $CHCl_3$: 3350,1785, 1710,1695 | $CDCl_3$: 3.42(s, 3H), 3.50(s, 2H), 3.53(s, 3H), 3.90-4.27(m, 2H), 4.57(bs, 2H), 5.02(s, 1H), 6.07(d, 1H, J = 6), 6.45(d, 1H, J = 6), 6.77(s, 1H), 7.13-7.60(m, 10H), 7.88(bs, 2H) |
| 3-6 | H | H | H | Cl | CH–$Ph_2$ | 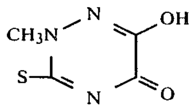 | $CHCl_3$: 3375,1790, 1720,1695, 1650 | |

TABLE III-continued

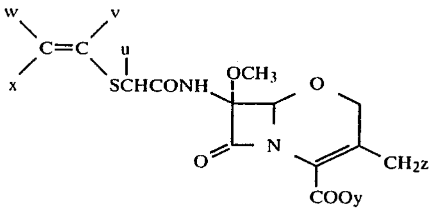

| No. | u | v | w | x | y | z | IR | NMR |
|---|---|---|---|---|---|---|---|---|
| 3-7 | H | H | H | Cl | CH<br>Ph$_2$ | STetCH$_3$ | CHCl$_3$:<br>3360,1790,<br>1700 | CDCl$_3$:<br>3.43(bs, 2H), 3.53(s, 3H), 3.72(s, 3H), 4.20 (bs, 2H), 4.62(bs, 2H), 5.05(s, 1H), 6.05(d, 1H, J = 6.5), 6.45(d, 1H, J = 6.5), 6.90(s, 1H), 7.10-7.73(m, 11H), |
| 3-8 | H | H | H | Cl | CH<br>Ph$_2$ | STetCH$_2$CH$_2$CN | CHCl$_3$:<br>3350,2250,<br>1790,1710 | CDCl$_3$:<br>7.7-7.1(m, 10H), 6.80(s, 1H), 6.45 + 6.08(ABq, 2H, J = 7), 5.05(s, 1H), 4.57(s, 2H), 4.27(t, 2H, J = 7), 4.17(s, 2H), 3.50(s, 3H), 3.42(s, 2H), 2.81(t, 2H, J = 7) |
| 3-9 | H | H | H | Cl | CH<br>Ph$_2$ | STetCH$_2$CH$_2$<br>CONH$_2$ | CHCl$_3$:<br>3380,3350,<br>1780,1720,<br>1690 | |
| 3-10 | H | H | H | Cl | CH<br>Ph$_2$ | STetCH$_2$CH$_2$<br>NH=CH—NH | CHCl$_3$:<br>3350,1785,<br>1710,1695 | CDCl$_3$:<br>3.35-3.82(m, 4H), 3.55(s, 3H), 4.05-4.48(m, 4H), 4.48-4.75(m, 2H), 5.08(s, 1H), 6.13(d, 1H, J = 7), 6.48 (d, 1H, J = 7), 6.47-6.97(m, 2H), 6.88(s, 1H), 7.20-7.87(m, 11H), 8.03(bs, 1H) |
| 3-11 | H | H | H | Cl | CH<br>Ph$_2$ | STetCH$_2$CH$_2$NH<br>tBuOCO | CHCl$_3$:<br>3440,3350,<br>1785,1705 | CDCl$_3$:<br>1.35(s, 9H), 3.27-3.67(m, 4H), 3.52(s, 3H), 4.07-4.40(m, 4H), 4.50-4.77(m, 2H), 5.07(s, 1H), 5.03-5.37(m, 1H), 6.07(d, 1H, J = 7), 6.47(d, 1H, J = 7), 6.85 s, 1H), 7.13-7.77(m, 11H) |
| 3-12 | H | H | H | Cl | CH<br>Ph$_2$ | STetCH$_2$CH$_2$<br>N(CH$_3$)$_2$ | CHCl$_3$:<br>3370,1795,<br>1700 | CDCl$_3$:<br>2.18(s, 6H), 2.68(t, 2H, J = 6), 3.45(s, 2H), 3.53(s, 3H), 4.18(t, 2H, J = 6), 4.23(bs, 2H), 4.62(bs, 2H), 5.03(s, 1H), 6.87(s, 1H), 7.15-7.6(m, 11H) |
| 3-13 | H | H | H | Cl | CH<br>Ph$_2$ | STetCH$_2$CH$_2$OH | CHCl$_3$:<br>3350,1780,<br>1705 | CDCl$_3$:<br>3.45(bs, 2H), 3.55(s, 3H), 3.80-4.37(m, 6H), 4.58 (bs, 2H), 5.03(s, 1H), 6.12(d, 1H, J = 7), 6.38(d, 1H, J = 7), 6.87(s, 1H), 7.10-7.63(m, 11H) |

TABLE III-continued

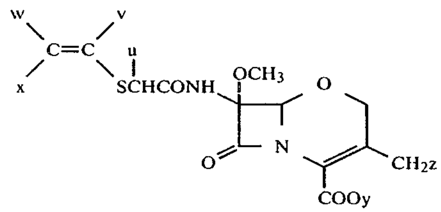

| No. | u | v | w | x | y | z | IR | NMR |
|---|---|---|---|---|---|---|---|---|
| 3-14 | H | H | H | Cl | $CH$—$Ph_2$ | $STetCH_2CH_2$—$OCH_3$ | $CHCl_3$: 3350,1780, 1710,1700 | $CDCl_3$: 3.27(s, 3H), 3.47(bs, 2H), 3.55(s, 3H), 3.70(t, 2H, J = 5), 4.62(s, 2H), 5.05(s, 1H), 6.12(d, 1H, J = 7), 6.37 (d, 1H, J = 7), 6.88(s, 1H), 7.10-7.67(m, 11H) |
| 3-15 | H | H | H | Cl | $CH$—$Ph_2$ | $STetCH_2CH_2OCO$—$ClCH_2$ | | Acetone-$d_6$: 3.53(s, 3H), 3.57(s, 2H), 4.13(s, 2H), 4.31(s, 2H), 4.58(s, 4H), 4.68(s, 2H), 5.10(s, 1H), 6.21(d, 1H, J = 7), 6.73(d, 1H, J = 7), 6.92(s, 1H), 7.2-8.25(m, 10H), 8.16(s, 1H) |
| 3-16 | H | H | H | Cl | $CH$—$Ph_2$ | $STetCH_2CH_2OCO$—$Cl_2CH$ | $CHCl_3$: 3690,3370, 1790,1702, 1631 mp: 172° C. | $CDCl_3$: 3.45(s, 2H), 3.57(s, 3H), 4.27(s, 2H), 4.47(t, 2H, J = 5), 4.53(t, 2H, J = 5), 4.63(s, 2H), 5.05(s, 1H), 5.87 (s, 1H), 6.13(d, 1H, J = 6), 6.37(d, 1H, J = 6), 6.90(s, 1H), 7.20-7.60(m, 11H) |
| 3-17 | H | H | H | Cl | $CH$—$Ph_2$ | $STetCH_2CH_2O$—$PhCH_2OCO$ | $CHCl_3$: 3370,1791, 1751,1702, 1631,1602, mp: 80-87° C. | $CDCl_3$: 7.2-7.7(m, 10H), 6.86(s, 1H), 6,37(d, 1H, J = 6), 6.12 (d, 1H, J = 6), 5.07(s, 2H), 5.03(s, 1H), 4.57(s, 2H), 4.41(s, 4H), 4.2(s, 2H), 3.53(s, 3H), 3.42(s, 2H), |
| 3-18 | H | H | H | Cl | $CH$—$Ph_2$ | $STetCH_2CHOH$—$CH_2OH$ | $CHCl_3$: 3440,1780, 1700 | $CDCl_3$ + $CD_3OD$: 3.10-3.67(m, 4H), 3.53(s, 3H), 3.80-4.40(m, 8H), 4.55(bs, 2H), 5.05(s, 1H), 6.10(d, 1H, J = 7), 6.50(d, 1H, J = 7), 7.10-7.63(m, 10H) |
| 3-19 | H | H | H | Cl | $CH$—$Ph_2$ | $STetCH_2CONH_2$ | $CHCl_3$: 3350,1788, 1700,1600 | $CDCl_3$: 3.43(s, 2H), 3.52(s, 3H), 4.18(s, 2H), 4.53(s, 2H), 4.87(s, 2H), 5.05(s, 1H), 6.10(d, 1H, J = 6), 6.42(d, 1H, J = 6), 6.6(br, 3H), 6.90(s, 1H), 7.2-7.7(m, 10H) |
| 3-20 | H | H | H | Cl | $CH$—$Ph_2$ | 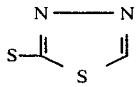 | $CHCl_3$: 3350,1785, 1720,1695 | $CDCl_3$: 3.42(s, 2H), 3.53(s, 3H), 4.20 + 4.47(ABq, 2H, J = 13), 4.58(bs, 2H), 5.03(s, 1H), 6.05(d, 1H, J = 7), 6.42(d, 1H, J = 7), 6.90(s, 1H), 7.08-7.60(m, 10H), 8.92(s, 1H) |

TABLE III-continued

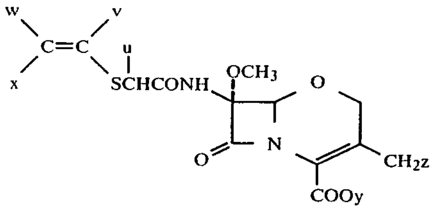

| No. | u | v | w | x | y | z | IR | NMR |
|---|---|---|---|---|---|---|---|---|
| 3-21 | H | H | H | $SCH_3$ | CH<br>$Ph_2$ | $STetCH_3$ | $CHCl_3$:<br>3340,1780,<br>1710,1690 | $CDCl_3$:<br>2.30(s, 3H), 3.43(bs, 2H), 3.58(s, 3H), 3.85(s, 3H), 4.27(s, 2H), 4.65(s, 2H), 5.07(s, 1H), 6.00(d, 1H, J = 8), 6.30(d, 1H, J = 8), 6.92(s, 1H), 7.20-7.68(m, 11H) |
| 3-22 | H | H | CN | Cl | CH<br>$Ph_2$ | $STetCH_3$ | $CHCl_3$:<br>3370,2210,<br>1793,1703 | $CDCl_3$:<br>3.52(s, 5H), 3.75(s, 3H), 4.23(s, 2H), 4.65(s, 2H), 5.07(s, 1H), 6.92(s, 1H), 7.2-7.5(m, 10H), 7.60(s, 1H) |
| 3-23 | H | H | $CH_2$<br>OH | Cl | CH<br>$Ph_2$ | $STetCH_3$ | $CHCl_3$:<br>3350,1780,<br>1717,1698 | $CDCl_3$:<br>3.42(bs, 2H), 3.50(s, 3H), 3.77(s, 3H), 3.90-4.33(m, 5H), 4.47-4.73(m, 2H), 5.03(s, 1H), 6.43(bs, 1H), 6.87(s, 1H), 7.2-7.6(m, 12H), 7.87(s, 1H), 9.25(s, 1H) |
| 3-24 | H | H | CO<br>$NH_2$ | Cl | CH<br>$Ph_2$ | $STetCH_3$ | Nujol:<br>3260,1775,<br>1700,1635 | DMSO—$d_6$:<br>3.45(s, 3H), 3.70(s, 3H), 3.72(s, 2H), 4.22(s, 2H), 4.40(s, 2H), 5.15(s, 1H), 6.87(s, 1H), 7.2-7.6(m, 12H), 7.87(s, 1H), 9.25(s, 1H) |
| 3-25 | H | H | CO<br>$OCHPh_2$ | Cl | CH<br>$Ph_2$ | $STetCH_3$ | Nujol:<br>3160,1780,<br>1705,1650 | DMSO—$d_6$:<br>3.35(s, 3H), 3.43(s, 2H), 3.83(s, 3H), 4.18(bs, 2H), 4.55 (bs, 2H), 5.20(s, 1H), 6.92(s, 1H), 6.95(s, 1H), 7.3-7.8(m, 20H), 8.48(s, 1H), 9.57(s, 1H) |
| 3-26 | H | H | Cl | Cl | CH<br>$Ph_2$ | $STetCH_3$ | $CHCl_3$:<br>3350,1785,<br>1700 | $CDCl_3$:<br>3.45(s, 2H), 3.57(s, 3H), 3.82(s, 3H), 4.27(s, 2H), 4.60(s, 2H), 5.08(s, 1H), 6.40(s, 1H), 6.88(s, 1H), 7.22-7.67(m, 11H) |
| 3-27 | H | $-(CH_2)_3CO-$ | | Cl | CH<br>$Ph_2$ | $STetCH_3$ | $CHCl_3$:<br>3360,1786,<br>1718,1678<br>mp: 110° C. | $CDCl_3$:<br>1.80-2.78(m, 6H), 3.56(s, 3H), 3.66(s, 2H), 3.83(s, 3H), 4.23(s, 2H), 4.67(s, 2H), 5.07(s, 1H), 6.92(s, 1H), 7.26-7.61(m, 11H) |
| 3-28 | H | CN | CN | $SCH_3$ | CH<br>$Ph_2$ | $STetCH_3$ | $CHCl_3$:<br>3530,3360,<br>2200,1785,<br>1715,1630 | $CDCl_3$:<br>7.2-7.6(m, 10H), 6.83(s, 1H), 5.00(s, 3H), 4.58(s, 2H), 4.20(s, 2H), 3.83(s, 2H), 3.75(s, 3H), 3.52(s, 3H), 2.57(s, 3H) |
| 3-29 | H | Cl | H | Cl | CH<br>$Ph_2$ | $STetCH_3$ | $CHCl_3$:<br>3350,1785,<br>1700 | $CDCl_3$:<br>3.55(s, 3H), 3.70(s, 2H), 3.77(s, 3H), 4.23(s, 2H), 4.62(s, 2H), 5.05(s, 1H), 6.47(s, 1H), 6.90(s, 1H), 7.10-7.67(m, 11H) |

TABLE III-continued

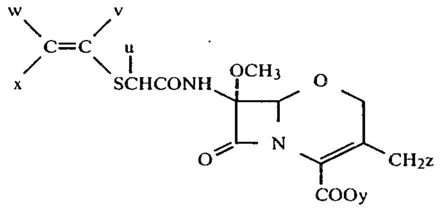

| No. | u | v | w | x | y | z | IR | NMR |
|---|---|---|---|---|---|---|---|---|
| 3-30 | Ph | H | H | Cl | $CH-Ph_2$ | $STetCH_3$ | | $CDCl_3$: 3.50(s, 3H), 3.83(s, 3H), 4.28(s, 2H), 4.61(s, 2H), 4.90(s, 1H), 5.08(s, 1H), 6.13(d, 1H, J = 7), 6.47(d, 1H, J = 7), 6.95(s, 1H), 7.17-7.70(m, 15H) |
| 3-31 | $CO-NH_2$ | H | H | Cl | $CH-Ph_2$ | $STetCH_3$ | $CHCl_3$: 1790,1710, 1695 | $CDCl_3$: 3.55(s, 3H), 3.80(s, 3H), 4.28(bs, 2H), 4.47(s, 1H), 4.63(d, 1H, J = 6.5), 6.92(s, 1H), 7.07-7.67(m, 12H), 8.53(bs, 1H) |
| 3-32 | CO-OtBu | H | H | Cl | $CH-Ph_2$ | $STetCH_3$ | | $CDCl_3$: 1.50(s, 9H), 3.58(s, 3H), 3.85(s, 3H), 4.20(s, 1H), 4.27(s, 2H), 4.63(s, 2H), 5.07(s, 1H), 6.16(d, 1H, J = 7), 6.58(d, 1H, J = 7), 6.92(s, 1H), 7.26-7.66(m, 10H) |
| 3-33 | 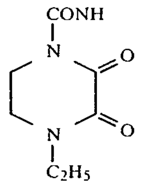 | H | H | Cl | $CH-Ph_2$ | $STetCH_3$ | Nujol: 3150,1780, 1705,1670 | $CDCl_3$: 1.13(bt, 3H, J = 6), 3.57(s, 3H), 3.80(s, 3H), 3.2-4.3 (m, 6H), 4.23(bs, 2H), 4.62(bs, 2H), 5.12(s, 1H), 5.93 (d, 1H, J = 7), 6.02 + 6.27 (each d, all 1H, J = 6), 6.63 (d, 1H, J = 6), 6.90(s, 1H), 7.2-8.0(m, 11H) |
| 3-34 | $NH-CO-OC_2H_5$ | H | H | Cl | $CH-Ph_2$ | $STetCH_3$ | | $CDCl_3$: 1.20 + 1.25 (each t, all 3H, J = 7.5), 3.55 + 3.56(each s, all 3H), 3.78(s, 3H), 4.0-4.4(m, 2H), 4.27(s, 2H), 4.62(s, 2H), 5.10(s, 1H), 5.80(d, 1H, J = 8), 6.10 + 6.28(each d, all 1H, J = 6), 6.60(d, 1H, J = 6), 6.90(s, 1H), 7.3-7.8(m, 11H) |
| 3-35 | $N_3$ | H | H | Cl | $CH-Ph_2$ | $STetCH_3$ | Nujol: 3380,2110, 1790,1710 | $CDCl_3$: 3.57(s, 3H), 3.75(s, 4H), 4.23(s, 2H), 4.65(s, 2H), 5.10(s, 1H), 6.13 + 6.23(each d, all 1H, J = 7), 6.62(d, 1H, J = 7), 6.90(s, 1H), 7.2-7.7(m, 11H) |
| 3-36 | —S— | | $CH_2-OH$ | Cl | $CH-Ph_2$ | $STetCH_3$ | $CHCl_3$: 3600,3375, 1795,1728, 1702,1640 | $CDCl_3$: 3.60(s, 3H), 3.78(s, 3H), 4.18(s, 2H), 4.25(s, 2H), 4.65(s, 2H), 4.80(s, 1H), 5.10(s, 1H), 6.87(s, 1H), 7.2-7.6(m, 10H), 7.93(s, 1H) |

TABLE III-continued

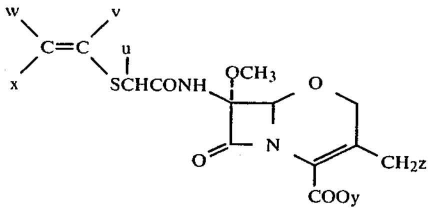

| No. | u | v | w | x | y | z | IR | NMR |
|---|---|---|---|---|---|---|---|---|
| 3-37 | | —S— | CHO | Cl | CH—Ph2 | STetCH3 | CHCl3: 1785,1720, 1700 | CDCl3: 3.58(s, 3H), 3.80(s, 3H), 4.23(s, 2H), 4.63(s, 2H), 5.08(s, 2H), 6.9(s, 1H), 7.7-7.1(m, 10H), 9.25(s, 1H) |
| 3-38 | | —S— | CO—NH2 | Cl | CH—Ph2 | STetCH3 | KBr: 3450,3350, 1785,1720 | CDCl3: 7.1-7.7(m, 10H), 6.87(s, 1H), 5.93(br, s, 2H), 5.10(s, 1H), 4.87(s, 1H), 4.65(s, 2H), 4.28(s, 2H), 3.82(s, 3H), 3.58(s, 3H) |
| 3-39 | | —S— | CO—OtBu | F | CH—Ph2 | STetCH3 | | CDCl3: 7.90-7.1(m, 10H), 6.87(s, 1H), 5.07(s, 1H), 34.83(s, 1H), 4.66(s, 2H), 4.20(s, 2H), 3.73(s, 3H), 3.56(s, 3H), 1.47(s, 9H) |
| 3-40 | | —S— | COO—tBu | SCH3 | CH—Ph3 | STetCH3 | CHCl3: 3380,1790, 1700,1660 | CDCl3: 1.51(s, 9H), 2.22(s, 3H), 3.62(s, 3H), 3.80(s, 3H), 4.28(s, 2H), 4.64(s, 3H), 5.11(s, 1H), 6.93(s, 1H), 7.2-7.7(m, 10H) |
| 3-41 | | —S— | COO—tBu | SPh | CH—Ph2 | STetCH3 | CHCl3: 3380,1790, 1705,1660 | CDCl3: 1.37(s, 9H), 3.57(s, 3H), 3.72(s, 3H), 4.22(s, 2H), 4.59(s, 2H), 4.74(s, 1H), 5.07(s, 1H), 6.92(s, 1H), 7.1-7.7(m, 10H) |
| 3-42 | | —S— | COO—tBu | SCF2—H | CH—Ph2 | STetCH3 | CHCl3: 3380,1795, 1705,1660 | CDCl3: 1.50(s, 9H), 3.61(s, 3H), 3.82(s, 3H), 4.28(s, 2H), 4.65(s, 2H), 4.73(s, 1H), 5.10(s, 1H), 6.68(t, 1H, J = 59), 6.94(s, 1H), 7.2-7.7(m, 10H) |
| 3-43 | | —S— | COO—tBu | Cl | CH—Ph2 | 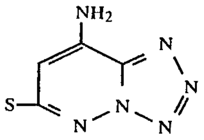 | CHCl3: 3470,3390, 3190,3000, 1785,1710, 1700,1625 | CD3OD + CDCl3: 7.1-7.7(m, 10H), 6.88(s, 1H), 6.80(s, 2H), 6.23(s, 1H), 5.13(s, 1H), 4.88(s, 2H), 4.45 + 4.10(ABq, J = 12), 3.60(s, 3H), 1.48(s, 9H) |
| 3-44 | | —S— | COO—tBu | Cl | CH—Ph2 | STetCH3 | CHCl3: 3360,1790, 1710 | CDCl3: 7.70-7.1(m, 10H), 6.90(s, 1H), 5.08(s, 1H), 4.75(s, 1H), 4.65(s, 2H), 4.27(s, 2H), 3.80(s, 3H), 3.60(s, 3H), 1.50(s, 9H) |

TABLE III-continued

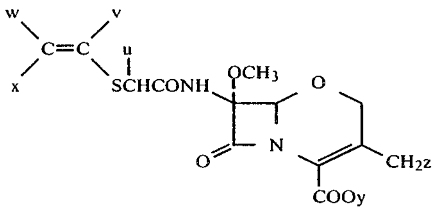

| No. | u | v | w | x | y | z | IR | NMR |
|---|---|---|---|---|---|---|---|---|
| 3-45 | —S— | | COO<br>tBu | Cl | CH<br>Ph2 | STetCH2CH2CN | CHCl3:<br>3360,3275,<br>2250,1782,<br>1709,1665,<br>1576 | CDCl3:<br>1.48(s, 9H), 2.92(t, 2H, J = 6), 3.62(s, 3H), 4.27(s, 2H), 4.38(t, 2H, J = 6), 4.63(s, 2H), 4.78(s, 1H), 5.12 (s, 1H), 6.92(s, 1H), 7.2-7.7(m, 11H) |
| 3-46 | —S— | | COO<br>tBu | Cl | CH<br>Ph2 | STetCH2CH2<br>(CH3)2N | CHCl3:<br>3375,1792,<br>1710,1670,<br>1580 | CDCl3:<br>1.48(s, 9H), 2.17(s, 6H), 2.67(t, 2H, J = 6), 3.42(s, 3H), 4.18(t, 2H, J = 6), 4.22(s, 2H), 4.62(s, 2H), 4.80 (s, 1H), 5.08(s, 1H), 6.90(s, 1H), 7.2-7.8(m, 11H) |
| 3-47 | —S— | | COO<br>tBu | Cl | CH<br>Ph2 | STetCH2CH2OH | CHCl3:<br>3500,3370,<br>1785,1720,<br>1700,1660 | CDCl3:<br>1.48(s, 9H), 3.58(s, 3H), 4.00(bs, 2H), 4.22(s, 4H), 4.60(s, 2H), 4.80(s, 1H), 5.10(s, 1H), 6.88(s, 1H), 7.3-7.9(m, 11H) |
| 3-48 | —S— | | COO<br>tBu | Cl | CH<br>Ph2 | STetCH2CH2O<br>CO<br>O<br>p-CH3C6H4CH2 | CHCl3:<br>3380,1790,<br>1748,1714,<br>1668,1580, | CDCl3:<br>1.48(s, 9H), 2.30(s, 3H), 3.60(s, 3H), 4.12 + 4.30 (ABq, 2H, J = 12), 4.41(s, 4H), 4.60(s, 2H), 4.78(s, 1H), 5.04(s, 2H), 5.09(s, 1H), 6.91(s, 1H), 7.1-7.6(m, 14H), 7.74(s, 1H) |
| 3-49 | —S— | | COO<br>tBu | Cl | CH<br>Ph2 | STetCH2<br>H2NCO | CHCl3:<br>3392,3375,<br>1792,1710,<br>1580 | CDCl3:<br>1.48(s, 9H), 3.57(s, 3H), 4.17(s, 2H), 4.53(s, 2H), 4.83(s, 3H), 5.10(s, 1H), 6.23(bs, 2H), 6.88(s, 1H), 7.2-7.7(m, 11H), 7.83(s, 1H) |
| 3-50 | —S— | | COO<br>tBu | Br | CH<br>Ph2 | STetCH3 | | CDCl3:<br>7.80-7.00(m, 10H), 6.87(s, 1H), 5.08(s, 1H), 4.75(s, 1H), 4.63(s, 2H), 4.25(s, 2H), 3.78(s, 3H), 3.60(s, 3H), 1.52(s, 9H) |
| 3-51 | —S— | | COO<br>tBu | I | CH<br>Ph2 | STetCH3 | | CDCl3:<br>7.70-7.10(m, 10H), 6.88(s, 1H), 5.07(s, 1H), 4.70(s, 1H), 4.63(s, 2H), 4.25(s, 2H), 3.78(s, 3H), 3.58(s, 2H), 1.48(s, 9H) |

TABLE III-continued

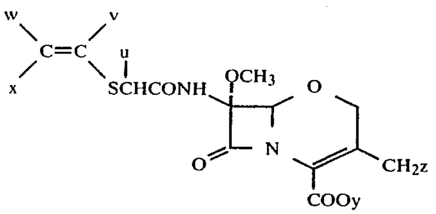

| No. | u | v | w | x | y | z | IR | NMR |
|---|---|---|---|---|---|---|---|---|
| 3-52 | H | Ph | H | Cl | CH(Ph2) | STetCH3 | CHCl3: 1785,1700 | CDCl3: 3.20(s, 2H), 3.54(s, 3H), 3.77(s, 3H), 4.27(s, 2H), 4.60, 4.71(ABq, 2H, J = 18), 5.06(s, 1H), 6.58(s, 1H), 6.92(s, 1H), 7.10(bs, 1H), 7.23-7.66(m, 10H) |
| 3-53 | H | H | NH2CO | F | CH(Ph2) | STetCH2CH2OCOO(p-CH3)PhCH2 | CHCl3: 3500,3400, 1780,1740, 1695 | CDCl3: 2.33(s, 3H), 3.52(s, 5H), 4.10-4.70(m, 8H), 5.07(s, 3H), 5.83-6.27(m, 2H), 6.90(s, 1H), 6.62-7.70(m, 16H) |
| 3-54 | H | H | H2NCO | F | CH(Ph2) | STetCH2CONH2 | KBr: 3375,1785, 1680,1660 | Acetone-d6: 3.52(s, 3H), 3.70(s, 2H), 4.20-4.40(m, 2H), 4.62(bs, 2H), 5.12(s, 3H), 6.70-7.77(m, 16H) |
| 3-55 | H | H | CO(NHCH3) | F | CH(Ph2) | STetCH2CH=CH2 | CHCl3: 3450,3360, 1785,1700, 1675 | CDCl3: 2.90(d, 3H, J = 4), 3.58(s, 5H), 3.70(s, 2H), 4.7 (s, 2H), 4.83(s, 1H), 5.0-6.2(m, 5H), 6.95(s, 1H), 6.5-7.8(m, 13H) |
| 3-56 | H | H | CO(NH2) | F | CH(Ph2) | STetCH2CH=CH2 | CHCl3: 3500,3400, 1785,1700, 1630 | CDCl3: 3.53(s, 5H), 4.26(s, 2H), 4.5-6.2(m, 9H), 6.70 (s, 1H), 6.89(d, 1H, J = 36), 7.2-7.9(m, 11H) |
| 3-57 | H | H | H | F | CH(Ph2) | STetCH2CH=CH2 | Nujol: 3200,3160, 1780,1725, 1650 | CDCl3: 3.38(s, 2H), 3.55(s, 3H), 4.6-6.1(m, 8H), 6.66 (dd, 1H, J = 81.5), 6.90(s, 1H), 7.2-7.6(m, 11H) |
| 3-58 | H | H | H | F | CH(Ph2) | STetCH2CONH(H2NCOCH2) | CHCl3: 3350,1785, 1710 | Acetone-d6: 3.55(s, 5H), 3.92(d, 2H, J = 6), 4.26(s, 2H), 4.63 (s, 2H), 5.15(s, 1H), 5.23(s, 2H), 5.77(dd, 1H, J = 40.5), 6.93(s, 1H), 6.3-8.3(m, 15H) |
| 3-59 | H | H | H | F | CH(Ph2) | STetCH2CONH(H2NCO) | CHCl3: 3500,3330, 1785,1720 | CDCl3—CD3OD: 3.40(s, 2H), 3.55(s, 3H), 4.15(s, 2H), 4.55(s, 2H), 5.07(s, 2H), 5.10(s, 1H), 5.52(dd, 1H, J = 40.5), 6.69(dd, 1H, J = 81.5), 6.88(s, 1H), 7.2-8.3(m, 14H) |

TABLE III-continued

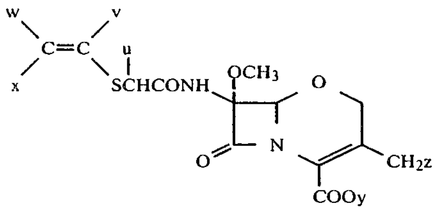

| No. | u | v | w | x | y | z | IR | NMR |
|---|---|---|---|---|---|---|---|---|
| 3-60 | H | H | H | F | CH<br>Ph$_2$ | 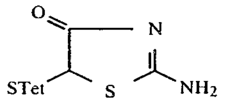 | $CHCl_3$:<br>3320,1785,<br>1720 | $CDCl_3$:<br>3.41(s, 2H), 3.58(s, 3H), 4.25(s, 2H), 4.48(s, 2H), 5.08, 5.10(each s, total 1H), 5.52(dd, 1H), J = 40.4), 6.70(s, 1H), 6.90(s, 1H), 6.4-7.7(m, 14H) |
| 3-61 | H | H | CO<br>NHCH$_3$ | F | CH<br>Ph$_2$ | STetCH$_2$CONH$_2$ | KBr:<br>3430,3340,<br>1780,1715,<br>1685,1670 | DMSO—$d_6$:<br>2.67(d, 3H, J = 5), 3.42(s, 3H), 3.65(s, 2H), 4.10-4.43(m, 2H), 4.47-4.78(m, 2H), 5.03(bs, 2H), 5.17(s, 1H), 6.88(s, 1H), 6.65-8.33(m, 14H) |
| 3-62 | H | H | CO<br>NH$_2$ | F | CH<br>Ph$_2$ | STetCH$_2$COHN<br>CH$_3$ | KBr:<br>3380,1786,<br>1720(sh),<br>1680,1630 | Acetone-$d_6$:<br>2.77(d, 3H, J = 9), 3.55(s, 3H), 3.72(s, 2H), 4.22 (bs, 2H), 4.63(bs, 2H), 5.07(s, 2H), 5.13(s, 1H), 6.90(s, 1H), 6.70-7.77(m, 15H) |
| 3-63 | H | H | CO<br>NHCH$_3$ | F | CH<br>Ph$_2$ | STetCH$_2$CH$_2$O<br>CH$_3$—PhCH$_2$OCO | $CHCl_3$:<br>3440,3350,<br>1785,1740,<br>1685,1635 | $CDCl_3$:<br>2.32(s, 3H), 2.82(d, 2H, J = 5), 3.55(s, 5H), 4.13-4.73(m, 8H), 5.07(s, 3H), 6.08-6.50(m, 1H), 6.83(d, 1H, J = 34), 6.90(s, 1H), 7.00-7.67(m, 15H) |
| 3-64 | H | H | H | F | CH<br>Ph$_2$ | STetCH$_2$CONH<br>CH$_3$ | $CHCl_3$:<br>3340,1785,<br>1672,1630 | $CDCl_3$:<br>2.70(d, 3H, J = 5), 3.40(s, 2H), 3.56(s, 3H), 4.17 (bs, 2H), 4.57(bs, 2H), 4.81(bs, 2H), 5.03(s, 1H), 5.47(dd, 1H, J = 38.4), 6.72(s, 1H), 5.97-7.67(m, 13H) |
| 3-65 | H | H | H | F | CH<br>Ph$_2$ | STetCH$_2$CONH$_2$ | $CHCl_3$:<br>3330,1780,<br>1708,1623 | $CDCl_3$:<br>3.35(bs, 2H), 3.50(s, 3H), 3.92-5.13(m, 7H), 5.43(dd, 1H, J = 4.40), 6.83(s, 1H), 5.92-7.77 (m, 14H) |
| 3-66 | H | H | H | F | CH<br>Ph$_2$ | STetCH$_2$CH$_2$O<br>p-CH$_3$C$_6$H$_4$CH$_2$OCO | $CHCl_3$:<br>3340,1787,<br>1740,1695,<br>1625 | $CDCl_3$:<br>2.30(s, 3H), 3.35(bs, 2H), 3.52(s, 3H), 4.18 (bs, 2H), 4.39(bs, 4H), 4.57(bs, 2H), 5.00(s, 3H), 5.37(dd, 1H, J = 40.4), 6.80(s, 1H), 5.90-7.57(m, 16H) |
| 3-67 | H | H | H | F | CH<br>Ph$_2$ | STetCH$_2$CONH<br>HOCH$_2$CH$_2$ | $CHCl_3$:<br>3340,1783,<br>1693,1630 | $CDCl_3$:<br>3.52(s, 3H), 3.18-5.13(m, 13H), 5.43(dd, 1H, J = 4.40), 6.88(s, 1H), 6.30-7.83(m, 13H) |

TABLE III-continued

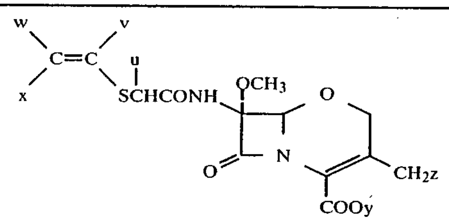

| No. | u | v | w | x | y | z | IR | NMR |
|---|---|---|---|---|---|---|---|---|
| 3-68 | H | H | H | F | CH<br>\|<br>$Ph_2$ | $STetCH_2NHCO$<br>\|<br>$HOCH_2CH_2NH$ | | $CDCl_3$:<br>3.55(s, 5H), 3.13-3.73(m, 4H), 4.07-4.27(m, 2H), 4.42-4.60(m, 2H), 4.77-4.90(m, 2H), 5.05 (s, 1H), 5.45(dd, 1H, J = 4.40), 6.82(s, 1H), 5.97 (m, 14H) |
| 3-69 | H | H | H | F | CH<br>\|<br>$Ph_2$ | $STetCH_2NHCO$<br>\|<br>$HOCH_2CH_2NH$ | | $CDCl_3$:<br>3.55(s, 5H), 3.13-3.73(m, 4H), 4.07-4.27(m, 2H), 4.42-4.60(m, 2H), 4.77-4.90(m, 2H), 5.05 (s, 1H), 5.45(dd, 1H, J = 4.40), 6.82(s, 1H), 5.97 (m, 14H) |
| 3-70 | H | H | CO<br>\|<br>$NHCH_3$ | F | CH<br>$Ph_2$ | $STetCH_2CONH$<br>\|<br>$CH_3$ | $CHCl_3$:<br>3430,3320, 1780,1710 (sh),1680, 1630 | $CDCl_3$:<br>2.70-2.90(m, 6H), 3.57(s, 5H), 4.20 (brs, 2H), 4.57(bs, 2H), 4.90(s, 2H), 5.07(s, 1H), 6.88(s, 1H), 6.82 (d, 1H, J = 34), 7.30-7.70(m, 13H) |
| 3-71 | H | H | H | F | CH<br>$Ph_2$ | $STetCH_2CO$<br>\|<br>NH 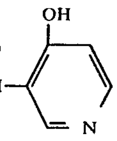 | KBr:<br>3260,1785, 1690,1665, 1630 | |
| 3-72 | H | H | $NH_2CO$ | F | $CH_3$ | $STetCH_2CH_2OH$ | Nujol:<br>3250(br), 1775,1675, 1600 | $CD_3COCD_3 + CD_3OD$:<br>3.50(s, 3H), 3.70(s, 2H), 3.83(s, 3H), 3.8-4.6(m, 6H), 4.64(s, 2H), 5.07(s, 1H), 6.98(d, 1H, J = 33) |
| 3-73 | H | H | $NH_2CO$ | F | $CH_2OC{=}O$<br>\|<br>$C(CH_3)_3$ | $STetCH_2CH_2OH$ | $CHCl_3$:<br>3470,3360, 1777,1760, 1677 | $CDCl_3 + CD_3OD$:<br>1.25(s, 9H), 3.55(s, 5H), 3.9-4.7 (m, 8H), 5.06(s, 1H), 5.87, 6.00 (ABq, 2H, J = 12), 6.87(d, 1H, J = 36) |
| 3-74 | H | H | $NH_2CO$ | F | $CHPh_2$ | $STetCH_2CH_2O$ 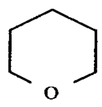 | $CHCl_3$:<br>3410,1775, 1680(br), 1630 | $CDCl_3 + CD_3OD$:<br>1.2-1.9(m, 6H), 3.55(s, 5H), 3.5-4.7(m, 10H), 5.05(s, 1H), 5.04 (brs, 1H), 6.89(s, 1H), 6.93(d, 1H, J = 36), 7.1-7.7(m, 10H) |

TABLE III-continued

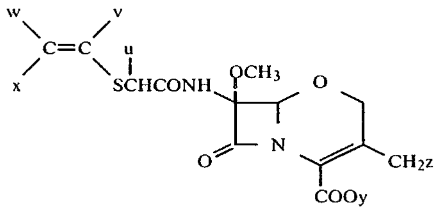

| No. | u | v | w | x | y | z | IR | NMR |
|---|---|---|---|---|---|---|---|---|
| 3-75 | H | H | $NH_2CO$ | F | $CH_2CCl_3$ | $STetCH_2CH_2OC{=}O$<br>$OCH_2Ph$ | $CHCl_3$: 3500,3390, 1785,1740, 1695,1632 | $CDCl_3$: 3.53(s, 3H), 3.57(s, 2H), 4.47-4.77(m, 8H), 4.93(s, 2H), 5.10(s, 1H), 5.15(s, 2H), 6.05-6.30(m, 2H), 6.87(d, 1H, J = 34), 7.37(s, 5H), 7.65-7.80(m, 1H) |
| 3-76 | H | H | $NH_2CO$ | F | 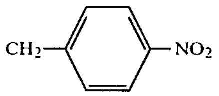 | $STetCH_2CH_2OC{=}O$<br>$OCH_2Ph$ | $CHCl_3$: 3500,3390, 1780,1740, 1690,1628 | $CDCl_3$: 3.37-3.70(m, 5H), 4.07-4.80(m, 8H), 5.03(s, 1H), 5.08(s, 2H), 5.32 (bs, 2H), 6.17-6.63(m, 2H), 6.92(d, 1H, J = 34), 7.28(s, 5H), 7.57(d, 2H, J = 8H), 7.87-8.03(m, 1H), 8.13(d, 2H, J = 8H) |
| 3-77 | H | H | $NH_2CO$ | F | 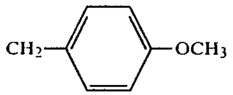 | $STetCH_2CH_2OC{=}O$<br>$OCH_2Ph$ | $CHCl_3$: 3480,3380, 1775,1740, 1687,1625, 1605 | $CDCl_3$: 3.47(bs, 5H), 3.75(s, 3H), 4.08-4.68(m, 8H), 5.00(s, 1H), 5.10(s, 2H), 5.17(s, 2H), 6.20-6.50(m, 2H), 6.62-7.47(m, 10H), 7.80-8.13(m, 1H) |
| 3-78 | H | H | $NH_2CO$ | F | $CHPh_2$ | $STetCH_2CH_2OC{=}O$<br>$OCH_2Ph$ | $CHCl_3$: 3480,3380, 1780,1740, 1685,1627 | $CDCl_3$: 3.53(bs, 5H), 4.10-4.73(m, 8H), 5.05(s, 1H), 5.08(s, 2H), 6.03-6.40(m, 2H), 6.63-7.64(m, 16H), 7.77-7.97(m, 1H) |
| 3-79 | H | H | $NH_2CO$ | F | $CHPh_2$ | 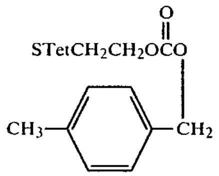 | $CHCl_3$: 3500,3400, 1780,1740, 1695 | $CDCl_3$: 2.33(s, 3H), 3.52(s, 5H), 4.10-4.7 (m, 8H), 5.07(s, 3H), 5.83-6.27(m, 2H), 6.90(s, 1H), 6.62-7.70(m, 16H) |

What we claim is:

1. A compound of the formula:

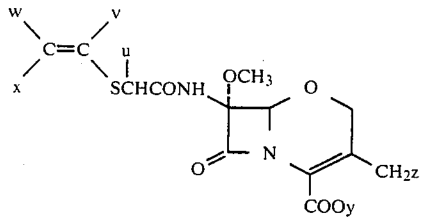

(I)

wherein u represents hydrogen, carboxamido, N-hydroxycarboxamido, carboxy, azido, an aryl, an acylamino, a protected carboxy or an N-alkoxycarboxamido, or, together with v, can represent —S— or —$CH_2S$—; v represents hydrogen, halogen, cyano or an alkylthio, or, together with u, can represent —S— or —$CH_2S$—, or, together with w, can represent —$(CH_2)_3CO$—; w represents hydrogen, carbamoyl, cyano, carboxy, an N-alkylcarbamoyl, an alkyl, an aryl, a protected carboxy or a heterocycle, or, together with v, can represent —$(CH_2)_3CO$—; x represents halogen, trifluoromethyl, an alkylthio or an arylthio; y represents hydrogen, a light metal or a carboxylic acid protecting group; and z represents an acyloxy or a heterocyclethio;

said alkyl being a straight chain or branched-chain $C_1$ to $C_5$ alkyl or $C_4$ to $C_7$ cycloalkyl;

said acyl being a straight chain or branched-chain $C_1$ to $C_7$ alkanoyl, $C_4$ to $C_7$ cycloalkylcarbonyl, a monocyclic or bicyclic $C_7$ to $C_{13}$ aroyl, $C_8$ to $C_{14}$ aralkanoyl or $C_9$ to $C_{15}$ arylalkenoyl, each optionally containing at least one hetero atom selected from nitrogen, oxygen and sulfur in the ring, $C_1$ to $C_5$ alkylsulfonyl, $C_6$ to $C_{12}$ arylsulfonyl, carbamoyl, a carbo-$C_1$ to $C_5$-alkoxy, a carbo-$C_7$ to $C_{13}$-aralkoxy or sulfo;

said aryl being a 5 or 6 membered, mono- or bicyclic $C_6$ to $C_{12}$ aryl group;

said heterocycle being a 5 or 6 membered, mono or bicyclic hetrocyclic group selected from the group consisting of furyl, thienyl, pyronyl, thiopyronyl, pyrrolyl, pyrazolyl, oxazolyl, thiazolyl, imidazolyl, oxadiazolyl, oxatriazolyl, thiadiazolyl, triazolyl, oxatriazolyl, thiatriazolyl, tetrazolyl, pyridyl, pyrimidyl, pyradinyl, pyridazinyl, triazinyl, indolyl, benzopyronyl, benzofuryl, benzothienyl, tetrazolopyridazinyl, purinyl, isoquinolyl, quinolyl and pyrimidopyridyl;

said carboxy protecting group being $C_7$ to $C_{14}$ aralkyl selected from the group consisting of benzyl, methylbenzyl, dimethylbenzyl, methoxybenzyl, ethoxybenzyl, nitrobenzyl, aminobenzyl, diphenylmethyl, phthalidyl, phenacyl, a substituted $C_1$ to $C_5$ alkyl selected from the group consisting of trichloroethyl, t-butyl and allyl, $C_6$ to $C_{12}$ aryl selected from the group consisting of pentachlorophenyl and indanyl, an ester residue formed with acetone oxime, acetophenone oxime, actaldoxime or N-hydroxyphthalimide, an acid anhydride residue formed with carbonic acid or $C_1$ to $C_{14}$ carboxylic acid, an amide selected from the group consisting of a hydroxyamide or alkoxyamide residue, an imide residue or a hydrazide residue, substituted alkyl groups selected from the group consisting of an alkanoyloxyalkyl, an alkoxyformyloxyalkyl, methoxymethyl, tetrahydropyranyl and 2-oxo-1,3-dioxolenylmethyl, substituted aralkyl groups selected from the group consisting of phenacyl and phthalidyl, substituted aryl group selected from the group consisting of phenyl, xylyl and indanyl;

said light metal being a metal belonging to the second to fourth period of the groups I to III in the periodic table, and selected from the group consisting of lithium, sodium, potassiun, magnesium, calcium and aluminum;

provided that said alkyl, acyl, aryl and carboxy protecting groups defined above can be substituted by hydroxy, halogen, cyano, carboxamido, carbamoyl, oxo, $C_1$ to $C_5$ alkyl, $C_1$ to $C_5$ alkoxy, $C_1$ to $C_{12}$ acyloxy, amino, $C_1$ to $C_{12}$ acylamino, di-$C_1$ to $C_5$-alkylamino, formylimidoylamino or protected carboxy, and that said heterocycle group defined above can be substituted by hydroxy, halogen, cyano, carboxamido, carbamoyl, oxo, $C_1$ to $C_5$ alkyl, $C_1$ to $C_5$ alkoxy, $C_1$ to $C_{12}$ acyloxy, amino, $C_1$ to $C_{12}$ acylamino, di-$C_1$ to $C_5$—alkylamino, formylimidoylamino, protected carboxy, carbamoylmethyl, alkylcarbamoylmethyl or hydroxyethyl optionally protected by aralkyl, an acylate-forming group selected from the group consisting of carbonic acyl, alkanoyl, aralkanoyl and aroyl, and an acetal forming group selected from the group consisting of methoxymethyl and tetrahydroxypyranyl.

2. The compound according to claim 1 wherein u and v, combined together, represent —S— or —$CH_2S$—.

3. The compound according to claim 1 wherein y is a light metal or a pharmacologically active ester residue.

4. A compound according to claim 1, said compound being 7β-(2-carbamoyl-2-fluorovinyl)thioacetamido-7α-methoxy-3-(1-hydroxyethyl-5-tetrazolyl)thiomethyl-1-dethia-1-oxa-3-cephem-4-carboxylic acid or an alkali metal salt thereof.

5. A bactericidal composition comprising a bactericidally effective amount of a compound according to claim 1 and a pharmaceutically acceptable carrier.

6. A composition according to claim 5 containing 0.01% to 99% of the active compound.

7. A composition according to claim 6 in dosage unit form.

8. A composition according to claim 7 suitable for injection.

9. A composition according to claim 8 in a form suitable for injection in an ampule or vial.

10. A composition according to claim 8 in the form of powder, crystals, microcrystals or lypholizate in a vial.

11. A method for treating human or veterinary bacterial infection comprising the administration to a patient of a bactericidally effective amount of a compound according to claim 1.

12. A method according to claim 11 for treating human or veterinary bacterial infection selected from the group consisting of pneumonia, bronchitis, pneumonitis, empyema, nasopharyngitis, tonsillitis, rhinitis, dermatitis, pustulosis, ulceration, absess, wound and soft tissue infection, ear infections, osteomyelitis, septicemia, gastroenteritis, enteritis, urinary tract infections, and pyelonephritis, when caused by bacteria sensitive to the active compound or for preventing post operative infection.

* * * * *